(12) United States Patent
Kawamura et al.

(10) Patent No.: US 8,829,026 B2
(45) Date of Patent: Sep. 9, 2014

(54) SULFAMOYL BENZOIC ACID HETEROBICYCLIC DERIVATIVES AS TRPM8 ANTAGONISTS

(75) Inventors: Kiyoshi Kawamura, Aichi (JP); Yuji Shishido, Aichi (JP); Masashi Ohmi, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 0 days.

(21) Appl. No.: 13/820,598

(22) PCT Filed: Oct. 3, 2011

(86) PCT No.: PCT/JP2011/005588
§ 371 (c)(1),
(2), (4) Date: Apr. 1, 2013

(87) PCT Pub. No.: WO2012/042915
PCT Pub. Date: Apr. 5, 2012

(65) Prior Publication Data
US 2013/0210858 A1    Aug. 15, 2013

Related U.S. Application Data

(60) Provisional application No. 61/388,696, filed on Oct. 1, 2010.

(51) Int. Cl.
*A61K 31/44* (2006.01)
*C07D 405/00* (2006.01)

(52) U.S. Cl.
USPC ......... 514/300; 514/337; 546/284; 546/275.7

(58) Field of Classification Search
USPC .................... 546/284, 275.7; 514/300, 337
See application file for complete search history.

(56) References Cited

U.S. PATENT DOCUMENTS

| 5,441,563 | A | 8/1995 | Sideman et al. | |
| 7,799,782 | B2 * | 9/2010 | Munson et al. | 514/234.5 |
| 2012/0094964 | A1 * | 4/2012 | Inoue et al. | 514/156 |

FOREIGN PATENT DOCUMENTS

| JP | 5-323534 | 12/1993 |
| JP | 2006-514614 | 5/2006 |
| JP | 2007-505849 | 3/2007 |
| WO | 2004/037251 | 5/2004 |
| WO | 2005/033081 | 4/2005 |
| WO | 2006/040103 | 4/2006 |
| WO | 2006/040136 | 4/2006 |
| WO | 2008/157500 | 12/2008 |
| WO | 2009/012430 | 1/2009 |
| WO | 2009/025793 | 2/2009 |
| WO | 2009/153285 | 12/2009 |
| WO | 2010/151797 | 12/2010 |
| WO | 2011/113861 | 9/2011 |

OTHER PUBLICATIONS

Makings et al. CAS: 142: 62706, 2004.*
International Search Report issued Dec. 6, 2011 in International (PCT) Application No. PCT/JP2011/005588.
Written Opinion issued Dec. 6, 2011 in International (PCT) Application No. PCT/JP2011/005588.
D. McKemy et al., "Identification of a cold receptor reveals a general role for TRP channels in thermosensation", Nature, vol. 416, pp. 52-58, 2002.
A. Peier et al., "A TRP Channel that Senses Cold Stimuli and Menthol", Cell, vol. 108, pp. 705-715, 2002.
Abe et al., "$Ca^{2+}$-dependent PKC activation mediates menthol-induced desensitization of transient receptor potential M8", Neuroscience Letters, vol. 397 (1-2), pp. 140-144, 2006.
L. Premkumar et al., "Downregulation of Transient Receptor Potential Melastatin 8 by Protein Kinase C-Mediated Dephosphorylation", The Journal of Neuroscience, vol. 25, No. 49, pp. 11322-11329, 2005.
K. Kobayashi et al., "Distinct Expression of TRPM8, TRPA1, and TRPV1 mRNAs in Rat Primary Afferent Neurons with Ab/C-Fibers and Colocalization with Trk Receptors", The Journal of Comparative Neurology, vol. 493 (4), pp. 596-606, 2005.
C. Roza et al., "Cold sensitivity in axotomized fibers of experimental neuromas in mice", Pain, vol. 120 (1-2), pp. 24-35, 2006.
H. Xing et al., "Chemical and Cold Sensitivity of Two Distinct Populations of TRPM8-Expressing Somatosensory Neurons", Journal of Neurophysiology, vol. 95 (2), pp. 1221-1230, 2006.
P. Gauchan et al., "Involvement of increased expression of transient receptor potential melastatin 8 in oxaliplatin-induced cold allodynia in mice", Neuroscience Letters, vol. 458, pp. 93-95, 2009.
K.C. Nicolaou et al., "Natural Product-like Combinatorial Libraries Based on Privileged Structures. 2. Construction of a 10 000-Membered Benzopyran Library by Directed Split-and-Pool Chemistry Using NanoKans and Optical Encoding", J. Am. Chem. Soc., vol. 122, No. 41, pp. 9954-9967, Compound 76, RN=310890-89-2, 310891-20-4, 310891-25-9, 2000.

* cited by examiner

*Primary Examiner* — Rei-tsang Shiao
(74) *Attorney, Agent, or Firm* — Wenderoth, Lind & Ponack, L.L.P.

(57) ABSTRACT

The present invention relates to sulfamoyl benzoic acid heterobicyclic derivatives of the formula (I) or a pharmaceutically acceptable salt thereof or a prodrug thereof, processes for their preparation, pharmaceutical compositions containing them and their use in the treatment of various disorders which are mediated via the TRPMb8 receptor.

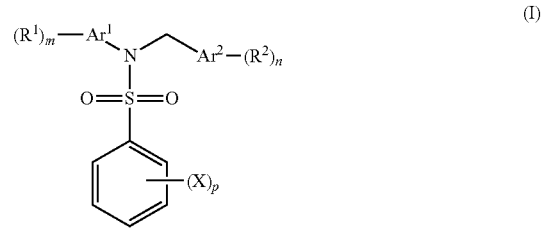

(I)

9 Claims, No Drawings

US 8,829,026 B2

SULFAMOYL BENZOIC ACID HETEROBICYCLIC DERIVATIVES AS TRPM8 ANTAGONISTS

This application claims the benefit of U.S. Provisional Application No. 61/388,696, filed Oct. 1, 2010.

TECHNICAL FIELD

This invention relates to sulfamoyl benzoic acid heterobicyclic derivatives that act as modulators of the TRPM8 receptor. The present invention also relates to processes for the preparation of novel sulfamoyl benzoic acid heterobicyclic derivatives and to their use in the treatment of a wide range of diseases, syndromes, and disorders, in particular for the treatment of inflammatory, pain and urological diseases or disorders.

BACKGROUND ART

Transient receptor potential (TRP) channels are one of the largest groups of ion channels, and they are divided into 6 sub-families (TRPV, TRPM, TRPA, TRPC, TRPP and TRPML). TRP channels are cation-selective channels that are activated by a variety of physical (e.g., temperature, osmolarity, mechanical) and chemical stimuli. TRPM8 is a member of TRP channel family. The receptor was cloned in 2002 (NPL 1; NPL 2) and it was found to be sensitive to cold temperature and menthol, and therefore named as cold menthol receptor-1 (CMR-1). TRPM8 can sense temperature changes in the range of both innocuous cold (15-28° C.) and noxious cold (<15° C.) as well as by chemical agents such as menthol and icilin.

TRPM8 is located on primary nociceptive neurons including A-delta and C-fibers and is also modulated by inflammation-mediated second messenger signals (NPL 3; NPL 4). The localization of TRPM8 on both A-delta and C-fibers may provide a basis for abnormal cold sensitivity in pathologic conditions wherein these neurons are altered, resulting in pain, often of a burning nature (NPL 5; NPL 6; NPL 7). Gauchan et al. reported that the expression of TRPM8 in the primary afferents was increased in oxaliplatin-induced cold allodynia model in mice (NPL 8). Oxaliplatin, a third-generation platinum-based chemotherapy drug, induces serious sensory neurotoxicity in patients, which is aggravated by exposure to cold.

Cold intolerance and paradoxical burning sensations induced by chemical or thermal cooling closely parallel symptoms seen in a wide range of clinical disorders and thus provide a strong rationale for the development of TRPM8 modulators as novel antihyperalgesic or antiallodynic agents. TRPM8 is also known to be expressed in the brain, lung, bladder, gastrointestinal tract, blood vessels, prostate and immune cells, thereby providing the possibility for therapeutic modulation in a wide range of maladies.

International patent application (PTL 1) purportedly describes substituted 4-benzyloxy-phenylmethylamide derivatives as cold menthol receptor-1 (CMR-1) antagonists for the treatment of urological disorders. International patent application (PTL 2) purportedly describes methods and pharmaceutical compositions for treatment and/or prophylaxis of respiratory diseases or disorders.

CITATION LIST

Patent Literature

{PTL 1} WO 2006/040136 A1
{PTL 2} WO 2006/040103 A1

Non Patent Literature

{NPL 1} McKemy, D. D., et al., Nature 416, 52-58, 2002
{NPL 2} Peier, A. D., Cell 108, 705-715, 2002
{NPL 3} Abe, J., et al Neurosci Lett 2006, 397(1-2), 140-144
{NPL 4} Premkumar, L. S., et al, J. Neurosci, 2005, 25(49), 11322-11329
{NPL 5} Kobayashi, K., et al, J Comp Neurol, 2005, 493 (4), 596-606
{NPL 6} Roza, C, et al. Pain, 2006, 120(1-2), 24-35
{NPL 7} Xing, H., et al, J Neurophysiol, 2006, 95(2), 1221-30
{NPL 8} Gauchan, P., et al. Neurosci Lett, 2009, 458, 93-95

SUMMARY OF INVENTION

Technical Problem

There is a need in the art for TRPM8 antagonists that can be used to treat a disease, syndrome, or condition in a mammal in which the disease, syndrome, or condition is affected by the modulation of TRPM8 receptors, such as chronic pain, neuropathic pain including cold allodynia and diabetic neuropathy, postoperative pain, osteoarthritis, rheumatoid arthritic pain, cancer pain, neuralgia, neuropathies, algesia, nerve injury, migraine, cluster and tension headaches, ischaemia, irritable bowel syndrome, neurodegeneration, fibromyalgia, stroke, itch, psychiatric disorders including anxiety and depression and inflammatory disorders such as asthma and chronic obstructive pulmonary, or airways, disease i.e., COPD, pulmonary hypertension, anxiety, including other stress-related disorders, urological diseases or disorders such as detrusor overactivity or overactive bladder, urinary incontinence, neurogenic detrusor overactivity or detrusor hyperflexia, idiopathic detrusor over-activity or detrusor instability, benign prostatic hyperplasia, and lower urinary tract symptoms, and combinations thereof.

TRPM8 antagonists should be well absorbed from the GI tract, be metabolically stable and possess favorable pharmacokinetic properties. They should be non-toxic. Furthermore, the ideal drug candidate will exist in a physical form that is stable, non-hygroscopic and easily formulated. In particular, it has been desired that compounds must bind potently to the TRPM8 receptor and show functional activity as antagonists. The present invention provides novel compounds which have excellent TRPM8 antagonistic activities.

Solution to Problem

The compounds of the present invention which have TRPM8 receptor antagonist activity are structurally quite different from the prior arts.

Then, WO 2009/025793 discloses sulfamoyl benzoic acid compounds. However, the compounds relate to human type 2 taste receptors for modulating taste perception, particularly bitter taste, which is quite different from TRPM8 receptor antagonist for the treatment of various disorders mediated via the TRPM8 receptor. Namely the sulfamoyl benzoic acid heterobicyclic derivatives in the present invention are neither disclosed as working examples in the patent nor TRPM8 receptor antagonist activity which are useful for the treatment of various disorders mediated via the TRPM8 receptor.

(1) The present invention provides a compound of the following formula (I) which is useful for the treatment of a condition or disorder mediated by TRPM8 receptor antagonistic activity

[Chem. 1]

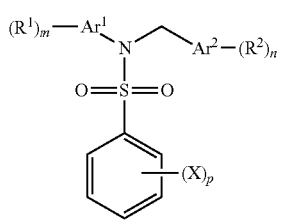

(I)

wherein
$Ar^1$ is monocyclic heteroaryl;
$Ar^2$ is bicyclic heteroaryl;
$R^1$ is hydrogen, halogen, $C_1$-$C_4$ alkyl, $C_1$-$C_4$ haloalkyl, hydroxy, $C_1$-$C_4$ alkoxy, $C_1$-$C_4$ haloalkoxy, $C_1$-$C_4$ alkylthio, nitro, amino, $C_1$-$C_4$ alkylamino, di($C_1$-$C_4$alkyl)amino, cyano, hydroxy $C_1$-$C_4$ alkyl, $C_1$-$C_4$ alkoxy $C_1$-$C_4$ alkyl, $C_1$-$C_4$ alkylsulfonyl, aminosulfonyl, $C_1$-$C_4$ alkyl C(=O)—, HO(O=)C—, $C_1$-$C_4$alkyl-O(O=)C—, $R^3N(R^4)C(=O)$—, $C_1$-$C_4$ alkylsulfonylamino, $C_3$-$C_7$ cycloalkyl, or $R^3C(=O)N(R^4)$—;

$R^2$ is hydrogen, halogen, $C_1$-$C_4$ alkyl, $C_1$-$C_4$haloalkyl, $C_1$-$C_4$ alkoxy, $C_1$-$C_4$ haloalkoxy, $C_1$-$C_4$ alkylthio, nitro, $C_1$-$C_4$ alkylsilyl, di($C_1$-$C_4$ alkyl)silyl, tri($C_1$-$C_4$ alkyl)silyl, amino, $C_1$-$C_4$ alkylamino, di($C_1$-$C_4$ alkyl)amino, cyano, hydroxy $C_1$-$C_4$ alkyl, $C_1$-$C_4$ alkoxy $C_1$-$C_4$ alkyl, $C_1$-$C_4$ alkylsulfonyl, aminosulfonyl, $C_1$-$C_4$ alkyl C(=O)—, HO(O=)C—, $C_1$-$C_4$ alkyl-O(O=)C—, $R^5N(R^6)C(=O)$—, $C_1$-$C_4$ alkylsulfonylamino, $C_3$-$C_7$ cycloalkyl, 3 to 7 membered heterocyclyl, or $R^5C(=O)N(R^6)$—;

said $C_3$-$C_7$ cycloalkyl and 3 to 7 membered heterocyclyl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl, cyano, amino, $C_1$-$C_4$ alkylamino, di($C_1$-$C_4$ alkyl)amino, $C_1$-$C_4$ alkylthio, $R^5N(R^6)C(=O)$— and nitro;

X is independently selected from HO(O=)C—$C_0$-$C_4$alkyl, hydrogen, hydroxy, halogen, $C_1$-$C_4$ alkyl, $C_1$-$C_4$ alkoxy, hydroxy $C_1$-$C_4$ alkyl, $C_1$-$C_4$ haloalkyl, $C_1$-$C_4$haloalkoxy, $C_3$-$C_7$ cycloalkyl, cyano, alkylsulfonyl, $C_1$-$C_4$ alkyl C(=O)—, $C_1$-$C_4$ alkyl-O(O=)C—, and $R^7N(R^8)C(=O)$—;

said alkyl may have independently 1 to 4 substituents independently selected from $C_1$-$C_4$ alkyl and halogen;
m is 1, 2 or 3; when m is two or more than two, R' may be same or different;
n is 1, 2 or 3; when n is two or more than two, $R^2$ may be same or different;
p is 1, 2, 3, 4 or 5; when p is two or more than two, X may be same or different;
$R^3$, $R^4$, $R^5$, $R^6$, $R^7$ and $R^8$ are independently selected from hydrogen, $C_1$-$C_4$ alkyl, hydroxy $C_1$-$C_4$ alkyl, $C_1$-$C_4$ alkoxy $C_1$-$C_4$ alkyl, amino $C_1$-$C_4$ alkyl, $C_1$-$C_4$ alkylamino $C_1$-$C_4$ alkyl, di($C_1$-$C_4$ alkyl)amino $C_1$-$C_4$ alkyl, 5 to 10 membered aryl, 5 to 10 membered aryl $C_0$-$C_4$ alkyl;

said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_8$ cycloalkyl, amino, $C_1$-$C_4$ alkylamino, di($C_1$-$C_4$ alkyl) amino, $C_1$-$C_4$ alkylthio, and nitro;
$C_3$-$C_8$ cycloalkyl, and 3 to 8 membered heterocyclyl $C_1$-$C_4$ alkyl;
said heterocyclyl and alkyl may have independently 1 to 4 substituents independently selected from $C_1$-$C_4$ alkyl and halogen;

or alternatively $R^3$ and $R^4$, $R^5$ and $R^6$ or $R^7$ and $R^8$ together with nitrogen atom to which they are attached may independently form a 4 to 8 membered ring which may contain nitrogen, oxygen or sulfur, wherein the 4 to 8 membered ring is optionally substituted with 1 to 6 substituents independently selected from the group consisting of hydroxy, $C_1$-$C_4$ alkyl, $C_1$-$C_4$ alkoxy, $C_3$-$C_7$ cycloalkyl, amino, oxo, $C_1$-$C_4$ alkylamino, and di($C_1$-$C_4$ alkyl)amino;

or a pharmaceutically acceptable salt thereof or a prodrug thereof.

(2) Preferable compounds of this invention are represented by formula (II)

[Chem. 2]

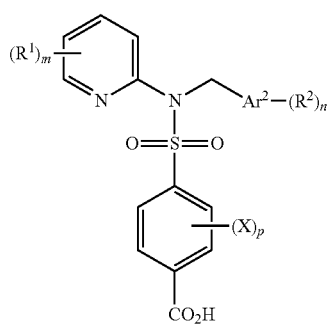

(II)

wherein $R^1$, $R^2$, $Ar^2$, X, m and n are the same as in the definition described in (1); p is 1, 2, 3 or 4; and when p is two or more than two, X may be same or different;

or a pharmaceutically acceptable salt thereof or a prodrug thereof.

(3) More preferable compounds of the invention are represented by formula (III)

[Chem. 3]

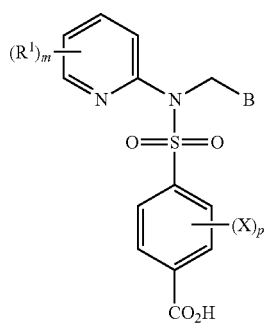

(III)

wherein
B is

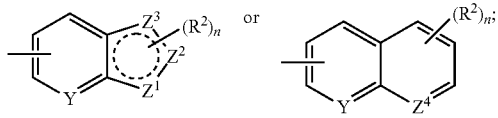

R¹, R², X, m and n are the same as in the definition described in (2);

p is 1 or 2; when p is two, X may be same or different;

Y is carbon or nitrogen;

$Z^1$, $Z^2$, $Z^3$, and $Z^4$ are independently selected from nitrogen, oxygen, and carbon;

m is 2; and n is 0 or 1;

or a pharmaceutically acceptable salt thereof or a prodrug thereof.

(4) Suitable individual compounds of the invention are:

4-(N-(Benzofuran-5-ylmethyl)-N-(3,5-dichloropyridin-2-yl)sulfamoyl)benzoic acid;

4-(N-(Benzofuran-6-ylmethyl)-N-(3,5-dichloropyridin-2-yl)sulfamoyl)benzoic acid;

4-(N-(3,5-Dichloropyridin-2-yl)-N-((1-methyl-1H-indol-5-yl)methyl)sulfamoyl)-3-methylbenzoic acid;

3-Chloro-4-(N-(3-chloro-5-(trifluoromethyl)pyridin-2-yl)-N-((1-ethyl-1H-indazol-5-yl)methyl)sulfamoyl)benzoic acid;

4-(N-(3-Chloro-5-(trifluoromethyl)pyridin-2-yl)-N-((1-ethyl-1H-indazol-5-yl)methyl)sulfamoyl)benzoic acid;

4-(N-(3,5-Dichloropyridin-2-yl)-N-((1-ethyl-1H-indazol-5-yl)methyl)sulfamoyl)benzoic acid;

4-(N-(Benzofuran-5-ylmethyl)-N-(3-chloro-5-(trifluoromethyl)pyridin-2-yl)sulfamoyl)benzoic acid;

4-(N-(Benzofuran-6-ylmethyl)-N-(3-chloro-5-(trifluoromethyl)pyridin-2-yl)sulfamoyl)benzoic acid;

4-(N-(3-Chloro-5-(trifluoromethyl)pyridin-2-yl)-N-((1-methyl-1H-indazol-5-yl)methyl)sulfamoyl)-3-methylbenzoic acid;

4-(N-(3,5-Dichloropyridin-2-yl)-N-((1-methyl-1H-indazol-5-yl)methyl)sulfamoyl)-3-methylbenzoic acid;

4-(N-(3-Chloro-5-(trifluoromethyl)pyridin-2-yl)-N-((1-cyclopropyl-1H-indazol-5-yl)methyl)sulfamoyl)benzoic acid;

4-(N-((1-Cyclopropyl-1H-indazol-5-yl)methyl)-N-(3,5-dichloropyridin-2-yl)sulfamoyl)benzoic acid;

3-Chloro-4-(N-(3-chloro-5-(trifluoromethyl)pyridin-2-yl)-N-((1-cyclopropyl-1H-indazol-5-yl)methyl)sulfamoyl)benzoic acid;

3-Chloro-4-(N-((1-cyclopropyl-1H-indazol-5-yl)methyl)-N-(3,5-dichloropyridin-2-yl)sulfamoyl)benzoic acid;

4-(N-(3-Chloro-5-(trifluoromethyl)pyridin-2-yl)-N-((1-cyclopropyl-1H-indazol-5-yl)methyl)sulfamoyl)-3-methylbenzoic acid;

4-(N-((1-Cyclopropyl-1H-indazol-5-yl)methyl)-N-(3,5-dichloropyridin-2-yl)sulfamoyl)-3-methylbenzoic acid;

4-(N-(3-Chloro-5-(trifluoromethyl)pyridin-2-yl)-N-((1-methyl-1H-indol-5-yl)methyl)sulfamoyl)benzoic acid;

3-Chloro-4-(N-(3-chloro-5-(trifluoromethyl)pyridin-2-yl)-N-((1-methyl-1H-indol-5-yl)methyl)sulfamoyl)benzoic acid; and 4-(N-(3-Chloro-5-(trifluoromethyl)pyridin-2-yl)-N-((1-methyl-1H-indol-5-yl)methyl)sulfamoyl)-3-methylbenzoic acid;

or a pharmaceutically acceptable salt thereof or a prodrug thereof.

(5) Also, the present invention provides an intermediate (IV) in a process for preparing a compound of this invention described in any one of (1) to (4):

[Chem. 4]

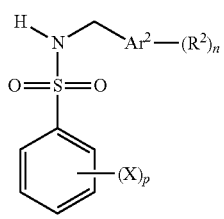

(IV)

wherein $Ar^2$ is bicyclic heteroaryl;

R² is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, nitro, $C_1$-$C_4$ alkylsilyl, di($C_1$-$C_4$ alkyl)silyl, tri($C_1$-$C_4$ alkyl)silyl, amino, $C_1$-$C_4$ alkylamino, di($C_1$-$C_4$ alkyl)amino, cyano, hydroxy $C_1$-$C_4$ alkyl, $C_1$-$C_4$ alkoxy $C_1$-$C_4$ alkyl, $C_1$-$C_4$ alkylsulfonyl, aminosulfonyl, $C_1$-$C_4$ alkyl C(=O)—, HO(O=)C—, $C_1$-$C_4$ alkyl-O(O=)C—, $R^5N(R^6)C(=O)$—, $C_1$-$C_4$ alkylsulfonylamino, $C_3$-$C_7$ cycloalkyl, 3 to 7 membered heterocyclyl, or $R^5C(=O)N(R^6)$—;

said $C_3$-$C_7$ cycloalkyl and 3 to 7 membered heterocyclyl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl, cyano, amino, $C_1$-$C_4$ alkylamino, di($C_1$-$C_4$ alkyl)amino, $C_1$-$C_4$ alkylthio, $R^5N(R^6)C(=O)$— and nitro;

X is independently selected from HO(O=)C—$C_0$-$C_4$alkyl, hydrogen, hydroxy, halogen, $C_1$-$C_4$ alkyl, $C_1$-$C_4$ alkoxy, hydroxy $C_1$-$C_4$ alkyl, $C_1$-$C_4$ haloalkyl, $C_1$-$C_4$haloalkoxy, $C_3$-$C_7$ cycloalkyl, cyano, alkylsulfonyl, $C_1$-$C_4$ alkyl C(=O)—, $C_1$-$C_4$ alkyl-O(O=)C—, and $R^7N(R^8)C(=O)$—;

said alkyl may have independently 1 to 4 substituents independently selected from $C_1$-$C_4$ alkyl and halogen;

n is 1, 2 or 3; when n is two or more than two, R² may be same or different;

p is 1, 2, 3, 4 or 5; when p is two or more than two, X may be same or different;

$R^5$, $R^6$, $R^7$ and $R^8$ are independently selected from hydrogen, $C_1$-$C_4$ alkyl, hydroxy $C_1$-$C_4$ alkyl, $C_1$-$C_4$ alkoxy $C_1$-$C_4$ alkyl, amino $C_1$-$C_4$ alkyl, $C_1$-$C_4$ alkylamino $C_1$-$C_4$ alkyl, di($C_1$-$C_4$ alkyl)amino $C_1$-$C_4$ alkyl, 5 to 10 membered aryl, 5 to 10 membered aryl $C_0$-$C_4$ alkyl;

said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_8$ cycloalkyl, amino, $C_1$-$C_4$ alkylamino, di($C_1$-$C_4$ alkyl) amino, $C_1$-$C_4$ alkylthio, and nitro; $C_3$-$C_8$ cycloalkyl, and 3 to 8 membered heterocyclyl $C_1$-$C_4$ alkyl;

said heterocyclyl and alkyl may have independently 1 to 4 substituents independently selected from $C_1$-$C_4$ alkyl and halogen;

or alternatively $R^5$ and $R^6$ or $R^7$ and $R^8$ together with nitrogen atom to which they are attached may independently form a 4 to 8 membered ring which may contain nitrogen, oxygen or sulfur, wherein the 4 to 8 membered ring is optionally substituted with 1 to 6 substituents independently selected from the group consisting of hydroxy, $C_1$-$C_4$ alkyl, $C_1$-$C_4$ alkoxy, $C_3$-$C_7$ cycloalkyl, amino, oxo, $C_1$-$C_4$ alkylamino, and di($C_1$-$C_4$ alkyl)amino;

or a pharmaceutically acceptable salt thereof or a prodrug thereof.

(6) Also, the present invention provides a use of a compound of this invention described in any one of (1) to (4) or a pharmaceutically acceptable salt thereof for the manufacture of a medicament for the treatment of a condition or disorder mediated by TRPM8 receptor antagonistic activity.

(7) Also, the present invention provides a use as described in (6), wherein the condition or disorder is one or more of inflammatory, pain and urological diseases or disorders, including chronic pain, neuropathic pain including cold allodynia and diabetic neuropathy, postoperative pain, osteoarthritis, rheumatoid arthritic pain, cancer pain, neuralgia, neuropathies, algesia, nerve injury, migraine, cluster and tension headaches, ischaemia, irritable bowel syndrome, neurodegeneration, fibromyalgia, stroke, itch, psychiatric disorders including anxiety and depression and inflammatory disorders such as asthma and chronic obstructive pulmonary, or airways, disease i.e., COPD, pulmonary hypertension, anxiety, including other stress-related disorders, urological diseases or disorders such as detrusor overactivity or overactive bladder, urinary incontinence, neurogenic detrusor overactivity or detrusor hyperflexia, idiopathic detrusor overactivity or detrusor instability, benign prostatic hyperplasia, and lower urinary tract symptoms, and combinations thereof.

(8) Also, the present invention provides a method for the treatment of a condition or disorder mediated by TRPM8 receptor antagonistic activity, in a mammalian subject, including a human, which comprises administering to a mammal in need of such treatment a therapeutically effective amount of a compound described in any one of (1) to (4) or a pharmaceutically acceptable salt thereof or a prodrug thereof or a prodrug thereof.

(9) Also, the present invention provides a method as described in (8), wherein said condition or disorder is one or more of inflammatory, pain and urological diseases or disorders, including chronic pain, neuropathic pain including cold allodynia and diabetic neuropathy, postoperative pain, osteoarthritis, rheumatoid arthritic pain, cancer pain, neuralgia, neuropathies, algesia, nerve injury, migraine, cluster and tension headaches, ischaemia, irritable bowel syndrome, neurodegeneration, fibromyalgia, stroke, itch, psychiatric disorders including anxiety and depression and inflammatory disorders such as asthma and chronic obstructive pulmonary or airways, disease i.e., COPD, pulmonary hypertension, anxiety, including other stress-related disorders, urological diseases or disorders such as detrusor overactivity or overactive bladder, urinary incontinence, neurogenic detrusor overactivity or detrusor hyperflexia, idiopathic detrusor overactivity or detrusor instability, benign prostatic hyperplasia, and lower urinary tract symptoms, and combinations thereof.

(10) Also, the present invention provides a pharmaceutical composition comprising a compound or a pharmaceutically acceptable salt thereof or a prodrug thereof, as described in any one of (1) to (4), and a pharmaceutically acceptable carrier.

(11) Also, the present invention provides a pharmaceutical composition as described in (10), further comprising another pharmacologically active agent.

(12) Also, the present invention provides a compound described in any one of (1) to (4) or a pharmaceutically acceptable salt thereof or a prodrug thereof for use in the treatment of a condition or disorder mediated by TRPM8 receptor antagonistic activity.

(13) Also, the present invention provides a process for preparing a pharmaceutical composition, wherein the process comprising mixing a compound described in any one of (1) to (4) or a pharmaceutically acceptable salt thereof or a prodrug thereof and a pharmaceutically acceptable carrier or excipient.

Examples of conditions or disorders mediated by TRPM8 receptor activity include, but are not limited to, TRPM8 related diseases.

Advantageous Effects of Invention

The compounds of the present invention show the TRPM8 receptor antagonistic activity. The compounds of the present invention may show less toxicity, good absorption, distribution, good solubility, less protein binding affinity other than TRPM8 receptor, less drug-drug interaction, and good metabolic stability.

DESCRIPTION OF EMBODIMENTS

As used herein, the term "alkyl" as a group or part of a group e.g. alkoxy or hydroxyalkyl refers to a straight or branched alkyl group in all isomeric forms. The term "$C_1$-$C_4$ alkyl" refers to an alkyl group, as defined above, containing at least 1, and at most 4 carbon atoms. Examples of such alkyl groups include methyl, ethyl, propyl, isopropyl, n-butyl, isobutyl, sec-butyl, or tert-butyl. Examples of such alkoxy groups include methoxy, ethoxy, propoxy, iso-propoxy, butoxy, iso-butoxy, sec-butoxy and tert-butoxy.

The term "cycloalkyl", as used herein, means a mono- or bicyclic ring, but not limited to, cyclopropyl, cyclobutyl, cyclopentyl, cyclohexyl, cycloheptyl, norboranyl, and adamantyl groups and the like.

The term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "haloalkyl", as used herein, means an alkyl radical which is substituted by halogen atom(s) as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups and the like.

The term "haloalkoxy", as used herein, means haloalkyl-O—, including, but not limited to, fluoromethoxy, difluoromethoxy, trifluoromethoxy, 2-fluoroethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups and the like.

The term "alkoxy", as used herein, means an O-alkyl group wherein "alkyl" is defined above.

The term "aryl", as used herein, means mono- or bi-carbocyclic or mono- or bi-heterocyclic ring which may contain 0-4 heteroatoms selected from O, N and S, but not limited to, phenyl, furyl, thienyl, oxazolyl, tetrazolyl, thiadiazolyl, pyridyl, pyrimidinyl, pyrrolyl, thiophenyl, pyrazinyl, pyridazinyl, pyrazolyl, isooxazolyl, isothiazolyl, triazolyl, furazanyl, naphthyl, tetrahydronaphthyl, indanyl, benzofuranyl, isobenzofuranyl, benzothiophenyl, indolyl, isoindolyl, benzoxazolyl, benzothiazolyl, indazolyl, benzoimidazolyl, benzotriazolyl, imidazopyridinyl, pyrazolopyrimidinyl, quinolyl, isoquinolyl, cinnolinyl, naphthyridinyl, phthalazinyl, quinazolinyl, quinoxalinyl, triazolopyrimidinyl, and the said rings which are fully or partially saturated, such as pyridin-2-onyl, piperidinyl, pyrrolidinyl, tetrehydronaphthalenyl, and the like.

Thus the term "monocyclic heteroaryl", as used herein, means mono-heterocyclic ring which is defined in the term "aryl" and N-oxides thereof and S-oxides thereof.

Thus the term "bicyclic heteroaryl", as used herein, means bi-heterocyclic ring which is defined in the term "aryl" and N-oxides thereof and S-oxides thereof.

The term "heterocyclyl", as used herein, means a saturated ring which comprises one or more heteroatoms selected from nitrogen, oxygen and sulphur. Examples of such heterocyclyl groups include azetidinyl, 1,4-dioxanyl, hexahydroazepinyl, pyrrolidinyl, piperidinyl, piperazinyl, morpholinyl, tetrahydrofuranyl, thiomorpholinyl, and tetrahydrothienyl, and N-oxides thereof and S-oxides thereof.

The term "$C_0$", as used herein, means direct bond.

The substituents on the ring may exist on the any atoms if it is chemically allowed. For example, when $Z^1$ is nitrogen and Y, $Z^2$, $Z^3$ are carbon in

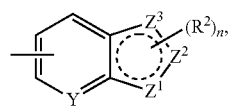

[Chem. 5]

then $(R^2)_n$ may be on the $Z^1$ and/or the other carbon atoms in the ring.

In the bi-heterocyclic ring

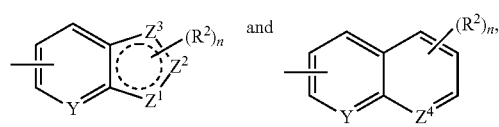

[Chem. 6]

the bond position is on the left ring including Y.

The term "protecting group", as used herein, means a hydroxy or amino protecting group which is selected from typical hydroxy or amino protecting groups described in Protective Groups in Organic Synthesis Forth Edition edited by T. W. Greene et al. (John Wiley & Sons, 2006);

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formula (I).

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci, 1977, 66, 1-19, such as acid addition salts formed with inorganic acids e.g. hydrochloric, hydrobromic, sulfuric, nitric or phosphoric acid; and organic acids e.g. succinic, maleic, formic, acetic, trifluoroacetic, propionic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H Bundgaard (Elsevier, 1985). Some examples of prodrugs in accordance with the invention include:

(i) where the compound of formula (I) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred are the moieties replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl.

(ii) where the compound of the formula (I) contains an amino group, an amide derivative prepared by reacting with a suitable acid halide or a suitable acid anhydride is exemplified as a prodrug. A particularly preferred amide derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

The compounds of formula (I), salts thereof and prodrugs thereof may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be some chiral carbon atoms. In such cases, compounds of formula (I) exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^{3}H$, $^{11}C$, $^{14}C$, $^{18}F$, $^{123}I$ and $^{125}I$. Compounds of the invention that contain the aforementioned isotopes and/or other isotopes of other atoms are within the scope of the present invention. Isotopically-labeled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances, Isotopically labeled compounds of the invention can generally be prepared by carrying out the procedures disclosed in the Schemes and/or in the Examples below, then substituting a readily available isotopically labeled reagent for a non-isotopically labeled reagent.

The potencies and efficacies of the compounds of this invention for TRPM8 can be determined by reporter assay performed on the human cloned receptor as described herein. Compounds of formula (I) have demonstrated antagonistic activity at the TRPM8 receptor, using the functional assay described herein.

Compounds of formula (I) and pharmaceutically acceptable salts thereof are therefore of use in the treatment of conditions or disorders which are mediated via the TRPM8 receptor. In particular the compounds of formula (I) and pharmaceutically acceptable salts thereof are of use in the treatment of a wide range of diseases, syndromes, and disorders, in particular for the treatment of inflammatory, pain and urological diseases or disorders, such as chronic pain, neuropathic pain including cold allodynia and diabetic neuropathy, postoperative pain, osteoarthritis, rheumatoid arthritic pain, cancer pain, neuralgia, neuropathies, algesia, nerve injury, migraine, cluster and tension headaches, ischaemia, irritable bowel syndrome, neurodegeneration, fibromyalgia, stroke, itch, psychiatric disorders including anxiety and depression and inflammatory disorders such as asthma and chronic obstructive pulmonary, or airways, disease i.e., COPD, pulmonary hypertension, anxiety, including other stress-related disorders, urological diseases or disorders such as detrusor overactivity or overactive bladder, urinary incontinence, neurogenic detrusor overactivity or detrusor hyperflexia, idiopathic detrusor overactivity or detrusor instability, benign prostatic hyperplasia, and lower urinary tract symptoms, and combinations thereof.

Activities of the compound (I) for each diseases, syndromes, and disorders described above can be confirmed in the suitable model known to skilled in the arts. For example, activities of compounds of formula (I) for neuropathic pain have been confirmed in chronic constriction injury (CCI)-induced model, such as cold allodynia and static allodynia model.

It is to be understood that "treatment" as used herein includes prophylaxis as well as alleviation of established symptoms.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrate compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or pharmaceutically acceptable salt thereof and a sterile vehicle. Formulations for injection may be presented in unit dosage form e.g. in ampoules or in multi-dose, utilising a compound of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts may also be formulated as depot preparations. Such long acting formulations may be administered by implantation (for example subcutaneously or intramuscularly) or by intramuscular injection. Thus, for example, the compounds of formula (I) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formula (I) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

A TRPM8 antagonist may be usefully combined with another pharmacologically active compound, or with two or more other pharmacologically active compounds, particularly in the treatment of inflammatory, pain and urological diseases or disorders. For example, a TRPM8 antagonist, particularly a compound of formula (I), or a pharmaceutically acceptable salt or solvate thereof, as defined above, may be administered simultaneously, sequentially or separately in combination with one or more agents selected from:

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, theamylal or thiopental;
- a benzodiazepine having a sedative action, e.g. chlordiazepoxide, clorazepate, diazepam, flurazepam, lorazepam, oxazepam, temazepam or triazolam;
- an $H_1$ antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex (registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
- an alpha-adrenergic, e.g. doxazosin, tamsulosin, clonidine, guanfacine, dexmetatomidine, modafinil, or 4-amino-6, 7-dimethoxy-2-(5-methane-sulfonamido-1,2,3,4-tetrahydroisoquinol-2-yl)-5-(2-pyridyl) quinazoline;
- a tricyclic antidepressant, e.g. desipramine, imipramine, amitriptyline or nortriptyline;
- an anticonvulsant, e.g. carbamazepine, lamotrigine, topiratmate or valproate;

a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-m orpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (registered trademark) or sarizotan;

a vanilloid receptor agonist (e.g. resinferatoxin) or antagonist (e.g. capsazepine);

a transient receptor potential cation channel subtype (V1, V2, V3, V4, M8, A1) Agonists and antagonists;

a beta-adrenergic, e.g. propranolol, or YM178 (2-(2-aminothiazol-4-yl)-N-[4-[2-[2(R)-hydroxy-2-phenylethylamino]ethyl]phenyl]acetamide);

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol (registered trademark);

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1alpha,3alpha,5alpha)(3-aminomethyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid;

a metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile, 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E$_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine;

a 5-HT3 antagonist, such as ondansetron;

a chemotherapy drug such as oxaliplatin, 5-fluorouracil, leukovolin, paclitaxel;

a calcitonin gene related peptide (CGRP) antagonist;

a bradykinin (BK1 and BK2) antagonist;

a voltage-gated sodium-dependent channel blocker (Nav1.3, Nav1.7, Nav1.8);

a voltage dependent calcium channel blocker (N-type, T-type);

a P2X (ion channel type ATP receptor) antagonist;

an acid-sensing ion channel (ASIC1a, ASIC3) antagonist;

and the pharmaceutically acceptable salts and solvates thereof.

Such combinations offer significant advantages, including synergistic activity, in therapy.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors.

A therapeutically effective amount of a compound of formula (I) or a pharmaceutical composition thereof includes a dose range from about 0.05 mg to about 3000 mg, in particular from about 1 mg to about 1000 mg or, more particularly, from about 10 mg to about 500 mg of active ingredient in a regimen of about once a day or more than once a day, for example two, three or four times a day for an average (70 kg) human; although, it is apparent to one skilled in the art that the therapeutically effective amount for active compounds of the invention will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of the inventive compound as the active ingredient.

Advantageously, a compound of formula (I) may be administered in a single daily dose, or the total daily dosage may be administered in divided doses of two, three and four times daily.

Optimal dosages of a compound of formula (I) to be administered may be readily determined and will vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level.

The above dosages are thus exemplary of the average case. There can be, of course, individual instances wherein higher or lower dosage ranges are merited, and such are within the scope of this invention.

Compounds of formula (I) may be administered in any of the foregoing compositions and dosage regimens or by means of those compositions and dosage regimens established in the art whenever use of a compound of formula (I) is required for a subject in need thereof.

As antagonists of the TRPM8 ion channel, the compounds of formula (I) are useful in methods for treating and preventing a disease, a syndrome, a condition, or a disorder in a subject, including an animal, a mammal and a human in which the disease, the syndrome, the condition, or the disorder is affected by the modulation of TRPM8 receptors. Such methods comprise, consist of, and consist essentially of administering to a subject, including an animal, a mammal, and a human in need of such treatment or prevention a therapeutically effective amount of a compound, salt, or solvate of formula (I). In particular, the compounds of formula (I) are useful for preventing or treating pain, or diseases, syndromes, conditions, or disorders causing such pain, or pulmonary or vascular dysfunction. More particularly, the compounds of formula (I) are useful for preventing or treating inflammatory pain, inflammatory hypersensitivity conditions, neuropathic pain, anxiety, depression, and cardiovascular disease aggravated by cold, including peripheral vascular disease, vascular hypertension, pulmonary hypertension, Raynaud's disease, and coronary artery disease, by administering to a subject in need thereof a therapeutically effective amount of a compound of formula (I).

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis.

One type of inflammatory pain is inflammatory hyperalgesia, which can be further distinguished as inflammatory somatic hyperalgesia or inflammatory visceral hyperalgesia. Inflammatory somatic hyperalgesia can be characterized by the presence of an inflammatory hyperalgesic state in which a hypersensitivity to thermal, mechanical and/or chemical stimuli exists. Inflammatory visceral hyperalgesia can also be characterized by the presence of an inflammatory hyperalgesic state, in which an enhanced visceral irritability exists.

Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease or ulcerative colitis.

One embodiment of the present invention is directed to a method for treating inflammatory somatic hyperalgesia in which a hypersensitivity to thermal, mechanical and/or chemical stimuli exists, comprising the step of administering to a mammal in need of such treatment a therapeutically effective amount of a compound, salt or solvate of formula (I).

A further embodiment of the present invention is directed to a method for treating inflammatory visceral hyperalgesia in which a enhanced visceral irritability exists, comprising, consisting of, and/or consisting essentially of the step of administering to a subject in need of such treatment a therapeutically effective amount of a compound, salt or solvate of formula (I).

A further embodiment of the present invention is directed to a method for treating neuropathic cold allodynia in which a hypersensitivity to a cooling stimuli exists, comprising, consisting of, and/or consisting essentially of the step of administering to a subject in need of such treatment a therapeutically effective amount of a compound, salt or solvate of formula (I).

Examples of an inflammatory hypersensitivity condition include urinary incontinence, benign prostatic hypertrophy, cough, asthma, rhinitis and nasal hypersensitivity, itch, contact dermatitis and/or dermal allergy, and chronic obstructive pulmonary disease.

Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain or neuralgia, pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

Examples of anxiety include social anxiety, post traumatic stress disorder, phobias, social phobia, special phobias, panic disorder, obsessive compulsive disorder, acute stress, disorder, separation anxiety disorder, and generalized anxiety disorder.

Examples of depression include major depression, bipolar disorder, seasonal affective disorder, post natal depression, manic depression, and bipolar depression.

General Synthesis

Throughout the instant application, the following abbreviations are used with the following meanings:

DMF: N,N-Dimethylformamide
THF: Tetrahydrofuran
DMSO: Dimethylsulfoxide
EtOAc: Ethyl acetate
MeOH: Methanol
EtOH: Ethanol
DCM: Dichloromethane
DME: 1,2-dimethoxyethane
NMP: N-Methyl-2-pyrrolidone
TFA: Trifluoroacetic acid
MeCN: Acetonitrile
IPE: Diisopropyl ether
TEA: Triethylamine
DMAP: 4-Dimethylaminopyridine
DEAD: Diethyl azodicarboxylate
EDC: 1-Ethyl-3-(3-dimethylaminopropyl)carbodiimide Hydrochloride
FMOC: 9-Fluorenylmethoxycarbonyl
HOBT: 1-Hydroxybenztriazole
HBTU: O-(Benzotriazol-1-yl)-N,N,N',N'-tetramethyluronium Hexafluorophosphate
BOP: (Benzotriazol-1-yloxy)tris(dimethylamino) phosphonium Hexafluorophosphate
HPLC: High pressure liquid chromatography
tR: Retention time
MHz: Megahertz
NMR: Nuclear Magnetic Resonance
TLC: Thin layer chromatography The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium tert-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, TEA, tripropylamine, tributylamine, diisopropylethylamine, N-methylpiperidine, pyridine, 4-pyrrolidinopyridine, picoline, 2,6-di(tert-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, TEA, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as DCM, chloroform, carbon tetra-chloride, and dichloroethane; ethers, such as diethyl ether, IPE, THF, and dioxane; aromatic hydrocarbons, such as benzene, toluene and nitrobenzene; amides, such as, DMF, N,N-dimethylacetamide, and hexamethylphosphoric triamide;

amines, such as N-methylmorpholine, TEA, tripropylamine, tributylamine, diisopropylethylamine, N-methylpiperidine, pyridine, 4-pyrrolidinopyridine, N,N-dimethylaniline, and N,N-diethylaniline; alcohols, such as MeOH, EtOH, propanol, isopropanol, and butanol; nitriles, such as MeCN and benzonitrile; sulfoxides, such as dimethyl sulfoxide (DMSO) and sulfolane; ketones, such as acetone and diethylketone. Of these solvents, including but not limited to DMF, DMSO, THF, diethylether, IPE, dimethoxyethane, MeCN, DCM, dichloroethane and chloroform are preferred.

EXAMPLES

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (TLC) and reaction times are given for illustration only; the structure and purity of all isolated compounds were assured by at least one of the following techniques: TCL (Merck silica gel 60 $F_{254}$ precoated TLC plates or Merck $NH_2$ $F_{254}$ precoated HPTLC plates), mass spectrometry or nuclear magnetic resonance (NMR). Microwave reaction was conducted by Intiator (registered trademark) Sixty (Biotage). Yields are given for illustrative purposes only. Flash column chromatography was carried out using Merck silica gel 60 (230-400 mesh ASTM), Fuji Silysia Chromatorex (registered trademark) DU3050 (Amino Type, 30-50 micrometer), Biotage silica (32-63 mm, KP-Sil), Biotage amino bounded silica (35-75 mm, KP-NH), Wakogel (registered trademark) C-300HGT, Hi-Flash (registered trademark) column (YAMAZEN, silica gel, 40 micro meters, 60 angstrom), Hi-Flash (registered trademark) column (YAMAZEN, amino, 40 micro meters, 60 angstrom). LC-MS analysis for intermediates and Examples were carried out by Waters 2695 Alliance HPLC with ZQ 2000 mass spectrometer and 2996 PDA detector. Analytical conditions (method-A, method-B, method-C, and method-D) are as follows.

Conditions for Method-A, Method-B, and Method-C:

| Column | Waters XTerra C18 2.1 × 30 mm, 3.5 microm |
|---|---|
| Column temperature | 45° C. |
| Flow rate | 0.5 mL/min |
| PDA detection | 210-400 nm scan (Exctracted wave length: 254 nm) |
| MS detection | ESI positive & negative mode |
| Mobile phases | A: MeCN (HPLC grade) |
| | B: 0.5% aqueous $HCO_2H$ |
| | C: 0.2% aqueous $NH_3$ |
| | D: $H_2O$ (Milli-Q water) |

| Time(min) | A(%) | B(%) | C(%) | D(%) |
|---|---|---|---|---|
| Method-A | | | | |
| 0 | 4 | 4.8 | 4.8 | 86.4 |
| 2 | 96 | 0.2 | 0.2 | 3.6 |
| Method-B | | | | |
| 0 | 4 | 0 | 4.8 | 91.2 |
| 2 | 96 | 0 | 0.2 | 3.8 |
| Method-C | | | | |
| 0 | 32 | 3.4 | 3.4 | 91.2 |
| 2 | 96 | 0.2 | 0.2 | 3.6 | run time 4 min

Conditions for Method-D:

| Column | Waters SunFire C18 4.6 × 50 mm, 5 microm |
|---|---|
| Column temperature: | 45° C. |
| Flow rate: | 0.8 mL/min |
| PDA detection: | 210-400 nm scan (Exctracted wave length: 215 nm) |
| MS detection: | ESI positive & negative mode |
| Mobile phases | A: MeCN (HPLC grade) |
| | B: 0.5% aqueous $HCO_2H$ |
| | C: 0.2% aqueous $NH_3$ |
| | D: $H_2O$ (Milli-Q water) |

| Time(min) | A(%) | B(%) | C(%) | D(%) |
|---|---|---|---|---|
| Method-D | | | | |
| 0 | 5 | 2.5 | 2.5 | 90 |
| 0.5 | 5 | 2.5 | 2.5 | 90 |
| 3.5 | 95 | 2.5 | 2.5 | 0 |
| 4 | 95 | 2.5 | 2.5 | 0 | run time 4.5 min

The further purification by preparative LC-MS system in usual manner for the Examples was carried out by preparative LC-MS and HPLC-QC method by using Waters Acquity Ultra Performance LC on TUV Detector and ZQ mass spectrometer. The chemical purity of the each Example was assured as greater than 90%. Details of the conditions are described in the section of the "Condition for determining HPLC-QC retention time for Example compounds" in the Examples, and the results are shown in the Table 1.

NMR data was determined at 270 MHz (JEOL JNM-LA 270 spectrometer) or 300 MHz (JEOL JNM-LA300) using deuterated chloroform (99.8% D) or dimethyl-sulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; microL (microliter(s)), microg (microgram(s)), microm (micrometer(s)), M (mol(s) per liter), microM (micromol(s) per liter), L (liter(s)), mL (milliliter(s)), g (gram(s)), mg (milligram(s)), mol (moles), mmol (millimoles).

All of the compounds of the formula (I) can be prepared by the procedures described in the general methods presented below or by the specific methods described in the Examples section and the Preparations section, or by routine modifications thereof. The present invention also encompasses any one or more of these processes for preparing the sulfamoyl benzoic acid heterobicyclic derivatives of formula (I), in addition to any novel intermediates used therein.

In the following general methods, $Ar^1$, $Ar^2$, $R^1$, $R^2$, X, m, n, and p are as previously defined for sulfamoyl benzoic acid heterobicyclic derivatives of the formula (I) unless otherwise stated.

<Scheme-A>

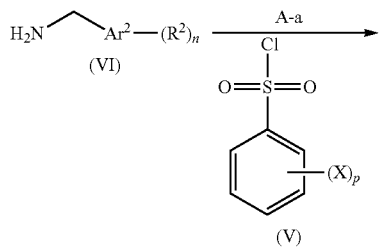

[Chem. 7]

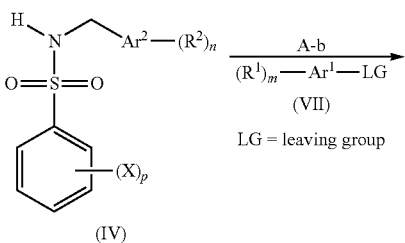

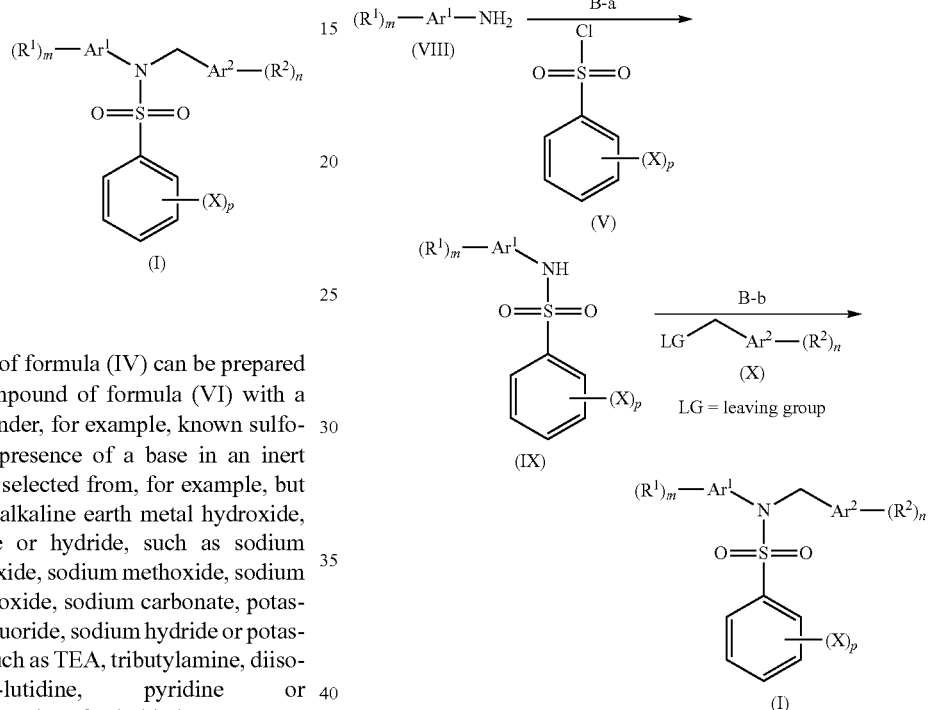

In Step A-a, a compound of formula (IV) can be prepared by sulfonylation of the compound of formula (VI) with a compound of formula (V) under, for example, known sulfonylation conditions in the presence of a base in an inert solvent. A preferred base is selected from, for example, but not limited to: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride; or an amine such as TEA, tributylamine, diisopropylethylamine, 2,6-lutidine, pyridine or dimethylaminopyridine. Examples of suitable inert aqueous or non-aqueous organic solvents include: alcohols, such as MeOH or EtOH; ethers, such as THF or 1,4-dioxane; acetone; dimethylformamide; halogenated hydrocarbons, such as DCM, 1,2-dichloroethane or chloroform; and pyridine; or mixtures thereof. The reaction can be carried out at a temperature in the range of from −10° C. to 200° C., preferably in the range of from 20° C. to 180° C. Reaction times are, in general, from 10 minutes to 4 days, preferably from 10 minutes to 24 hrs.

When LG is a suitable leaving group such as O-trifluoromethanesulfonate, O-tosylate, O-mesylate, iodide, bromide, or chloride, in Step A-b, a compound of formula (I) can be prepared by N-arylation of a compound of formula (IV) with aryl halide (VII) in the presence of a base in an inert solvent.

Examples of suitable bases include: potassium carbonate, sodium carbonate and cesium carbonate. Examples of suitable solvents include: 1,4-dioxane, THF, MeCN, NMP, DMSO, DMA, or DMF. The reaction can be carried out at a temperature of from 0° C. to 200° C., more preferably from 20° C. to 160° C. Reaction times are, in general, from 5 minutes to 96 hrs, more preferably from 30 minutes to 24 hrs. In an alternative case, the reaction can be carried out with microwave system in the presence of a same base in a same inert solvent. The reaction can be carried out at a temperature in the range of from 100° C. to 200° C., preferably in the range of from 120° C. to 160° C. Reaction times are, in general, from 10 minutes to 5 hrs, preferably from 10 minutes to 3 hr.

Carboxylic acid derivative of a compound (I) can be prepared from a compound of the corresponding ester by hydrolysis reaction using a suitable base such as aqueous sodium hydroxide and a suitable solvent such as THF, MeOH, or EtOH at a temperature of from 5° C. to 90° C. for 1-24 hrs.

In Step B-a, a compound of formula (IX) can be prepared from a compound of formula (VIII) by the method described in Step A-a above.

When LG is a halogen group such as iodide, bromide, or chloride, in Step B-b, a compound of formula (I) can be prepared by N-substitution reaction of a compound of formula (IX) with alkyl halide of (X) in the presence of a base in an inert solvent.

Examples of suitable bases include: potassium carbonate, sodium carbonate, or cesium carbonate. Examples of suitable solvents include: 1,4-dioxane, THF, MeCN, NMP, DMSO, DMA, or DMF. This reaction can be carried out in the presence of a suitable additive agent. Examples of such additive agents include: sodium iodide or potassium iodide. The reaction can be carried out at a temperature of from 20° C. to 150° C., more preferably from 20° C. to 100° C. Reaction times are, in general, from 5 minutes to 96 hours, more preferably from 30 minutes to 24 hrs.

Carboxylic acid derivative of a compound (I) can be prepared from a compound of the corresponding ester by hydrolysis reaction using a suitable base such as aqueous sodium hydroxide and a suitable solvent such as THF, MeOH, or EtOH at a temperature of from 5° C. to 90° C. for 1-24 hrs.

<Scheme-C>

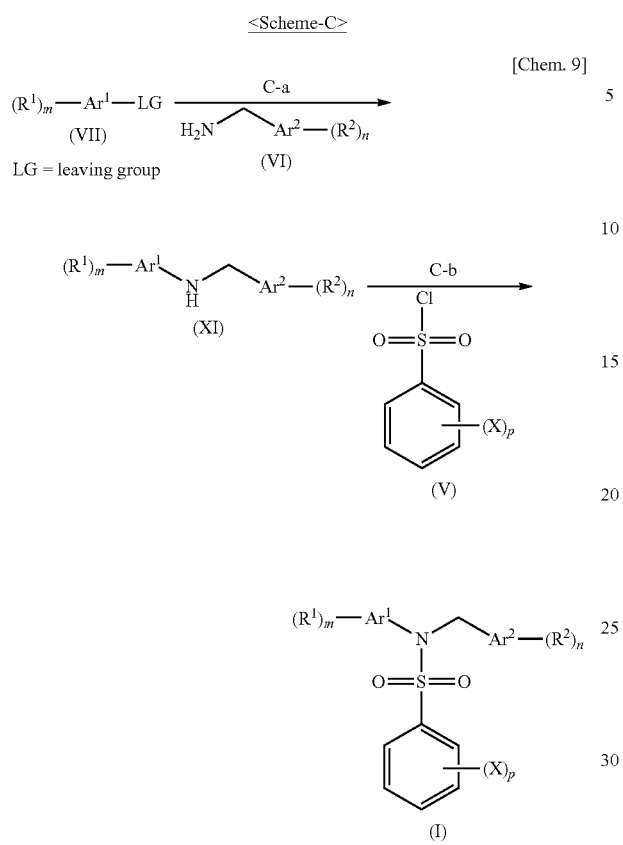

<Scheme -D>

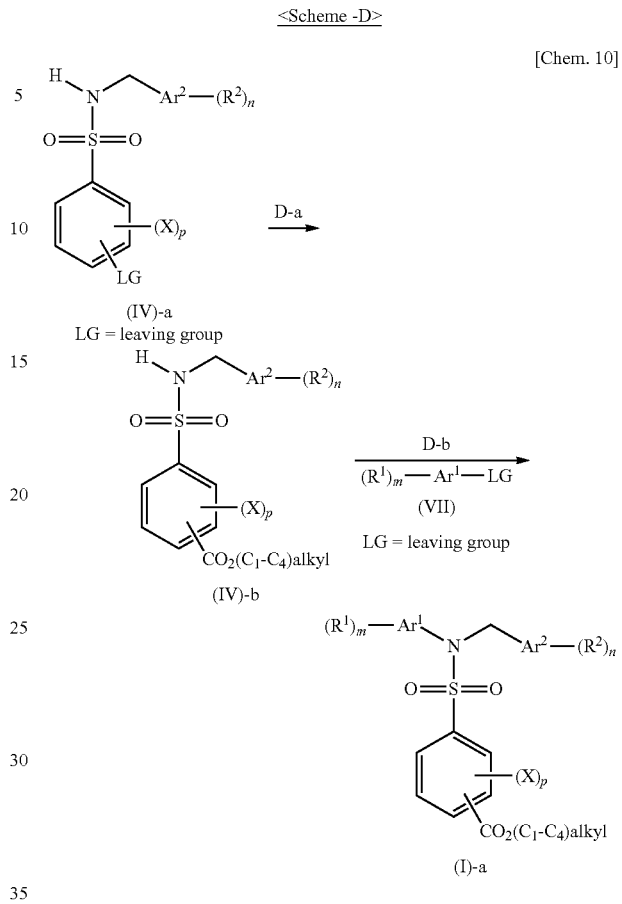

When LG is a suitable leaving group such as O-trifluoromethanesulfonate, O-tosylate, O-mesylate, iodide, bromide, or chloride, in Step C-a, a compound of formula (XI) can be prepared by N-arylation of a compound of formula (VI) with a compound of formula (VII) in the presence of a base in an inert solvent. Examples of suitable bases include: potassium carbonate, sodium carbonate, or cesium carbonate. Examples of suitable solvents include: 1,4-dioxane, THF, MeCN, NMP, DMSO, DMA, or DMF. The reaction can be carried out at a temperature of from 0° C. to 200° C., more preferably from 20° C. to 160° C. Reaction times are, in general, from 5 minutes to 96 hrs, more preferably from 30 minutes to 24 hrs. In an alternative case, the reaction can be carried out with microwave system in the presence of a same base in a same inert solvent. The reaction can be carried out at a temperature in the range of from 100° C. to 200° C., preferably in the range of from 120° C. to 160° C. Reaction times are, in general, from 10 minutes to 5 hrs, preferably from 10 minutes to 3 hr.

In Step C-b, a compound of formula (I) can be prepared from a compound of formula (XI) by the method described in Step A-a above.

Carboxylic acid derivative of a compound (I) can be prepared from a compound of the corresponding ester by hydrolysis reaction using a suitable base such as aqueous sodium hydroxide and a suitable solvent such as THF, MeOH, or EtOH at a temperature of from 5° C. to 90° C. for 1-24 hrs.

When LG is a suitable leaving group such as O-trifluoromethanesulfonate, O-tosylate, O-mesylate, iodide, bromide, or chloride, in Step D-a, the compound of formula ((IV)-b) can be prepared by reacting the compound of formula ((IV)-a) with carbon monoxide and alcohol (e.g. MeOH or EtOH) in the presence of a catalyst and/or base in an inert solvent. Examples of suitable catalysts include: palladium reagents, such as palladium(II) acetate or bis(dibenzylideneacetone)palladium(II). Examples of suitable bases include: N,N-diisopropylethylamine, N-methylmorpholine, or TEA. If desired, this reaction may be carried out in the presence or absence of an additive such as 1,1'-bis(diphenylphosphino)ferrocene, triphenylphosphine or 1,3-bis(diphenylphosphino)propane (DPPP). Examples of suitable solvents include: acetone; nitromethane; DMF; sulfolane; DMSO; NMP; 2-butanone; MeCN; halogenated hydrocarbons such as DCM, 1,2-dichloroethane or chloroform; or ethers, such as THF or 1,4-dioxane. The reaction can be carried out at a temperature of from 0° C. to 200° C., more preferably from 20° C. to 120° C. Reaction times are, in general, from 5 minutes to 96 hrs, more preferably from 30 minutes to 24 hrs.

In Step D-b, a compound of formula ((I)-a) can be prepared from a compound of formula ((IV)-b) by the method described in Step C-a above.

Carboxylic acid derivative of a compound (I) can be prepared from a compound of the corresponding ester by hydrolysis reaction using a suitable base such as aqueous sodium hydroxide and a suitable solvent such as THF, MeOH, or EtOH at a temperature of from 5° C. to 90° C. for 1-24 hrs.

<Scheme-E>

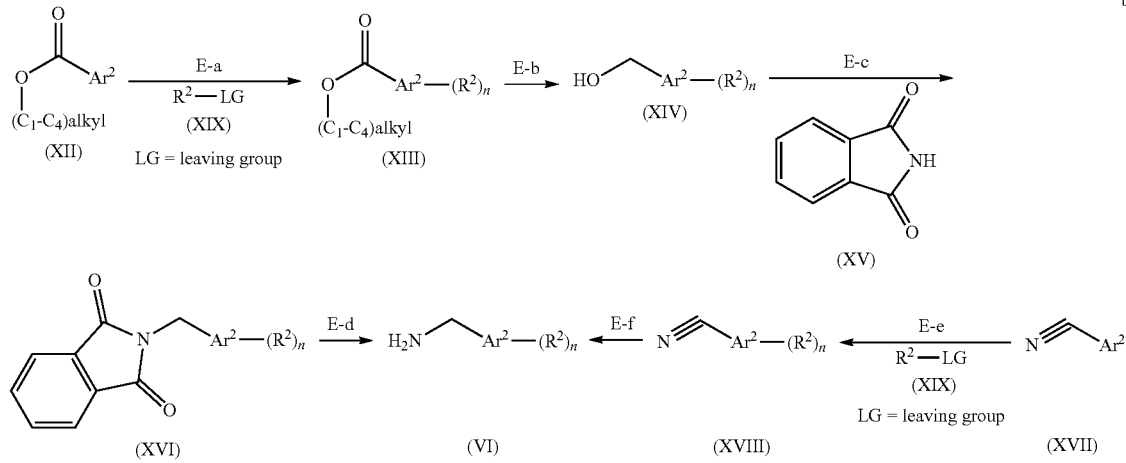

When LG is a suitable group such as O-trifluoromethanesulfonate, O-tosylate, O-mesylate, iodide, bromide, or chloride, in Step E-a and Step E-e, and when $Ar^2$ include NH group as an aromatic component, NH group can be N-alkylated with alkylating reagents of formula (XIX) in the presence of a base in an inert solvent. When LG is a metal group such as boronic acid, the reaction can be carried out in the presence of a suitable transition metal catalyst and in the presence of a base in an inert solvent. Example of suitable alkylating reagents include, but not limited to, iodomethane, iodoethan, or cyclopropylboronic acid. Examples of suitable bases include: sodium hydride, potassium carbonate, sodium carbonate, or cesium carbonate. Examples of suitable organic solvent include: THF, 1,4-dioxane, DMF, DCM, or 1,2-dichloroethane. Examples of suitable transition metal catalysts include: tetrakis(triphenylphosphine)palladium(0), bis (triphenylphosphine)palladium(ll) chloride, copper(0), copper(l) acetate, copper(l) bromide, copper(l) chloride, copper(l) iodide, copper(l) oxide, copper(ll) trifluoromethanesulfonate, copper(ll) acetate, copper(ll) bromide, copper(ll) chloride, copper(ll) iodide, copper(ll) oxide, copper(ll) trifluoromethanesulfonate, palladium(ll) acetate, palladium(ll) chloride, bis(MeCN)dichloropalladium(II), bis(dibenzylideneacetone)palladium(0), tris(dibenzylideneacetone)dipalladium(0) and [1,1'-bis(diphenylphosphino)ferrocene]palladium(ll) dichloride. Preferred catalysts are tetrakis (triphenylphosphine)palladium(0), bis(triphenylphosphine)palladium(ll) chloride, palladium(ll) acetate, palladium(ll) chloride, bis(MeCN)dichloropalladium(0), bis(dibenzylideneacetone)palladium(0), tris(dibenzylideneacetone)dipalladium(0), or [1,1-bis(diphenylphosphino)ferrocene]palladium(11) dichloride.

In Step E-b, a compound of formula (XIV) can be prepared by reduction of a compound of formula (XIII) The reduction may be carried out in the presence of a suitable reducing agent in an inert solvent or without solvent. A preferred reducing agent is selected from, for example, but not limited to, $NaBH_4$, $LiAlH_4$, $LiBH_4$, $BH_3$-complex and (iso-butyl)$_2$AlH. Reaction temperatures are generally in the range of from $-78°$ C. to $100°$ C., preferably in the range of from $-70°$ C. to $60°$ C. Reaction times are, in general, from 1 minute to a day, preferably from 3 hrs to 12 hrs. Examples of suitable solvents include: THF; 1,4-dioxane; DMF; MeCN; alcohols, such as MeOH or EtOH, and halogenated hydrocarbons, such as DCM, 1,2-dichloroethane, chloroform, or carbon tetrachloride.

In Step E-c, a compound of formula (XVI) can be prepared by the Mitsunobu reaction in the presence of triphenylphosine and ester of azodicarboxylic acid derivative in an inert solvent. Example of suitable ester of azodicarboxylic acids are azodicarboxylic acid methyl ester, azodicarboxylic acid ethyl ester, azodicarboxylic acid diidopropyl ester, and azodicarboxylic acid tert-butyl ester. Example of suitable solvents include: THF, 1,4-dioxane, DCM, or toluene. The reaction can be carried out at a temperature in the range of from $0°$ C. to $150°$ C., preferably in the range of from $20°$ C. to $100°$ C. Reaction times are, in general, from 10 minutes to 96 hrs, preferably from 30 minutes to 24 hr.

In Step E-d, a compound of formula (VI) can be prepared by de-protection with such as hydrazine in an inert solvent. Example of suitable solvents include: water, MeOH, or EtOH. The reaction can be carried out at a temperature in the range of from $0°$ C. to $150°$ C., preferably in the range of from $50°$ C. to $100°$ C. Reaction times are, in general, from 10 minutes to 96 hrs, preferably from 30 minutes to 24 hr.

In Step E-f, a compound of formula (VI) can be prepared by reduction of a compound of formula (XVIII). The reduction can be carried out in the presence of a suitable reducing agent in an inert solvent or without solvent. A preferred reducing agent is selected from, for example, but not limited to, $LiAlH_4$, $BH_3$-complex, or (iso-butyl)$_2$ AlH. Reaction temperatures are generally in the range of from $-78°$ C. to $100°$ C., preferably in the range of from $-70°$ C. to $60°$ C. Reaction times are, in general, from 1 minute to a day, preferably from 3 hrs to 12 hrs. Examples of suitable solvents include: THF; 1,4-dioxane; DMF; MeCN; alcohols, such as MeOH or EtOH, and halogenated hydrocarbons, such as DCM, 1,2-dichloroethane, chloroform, or carbon tetrachloride. In an alternative case, hydrogenation can be carried out in the presence of catalyst in an inert solvent. Examples of suitable catalyst include: Raney (registered trademark)nickel, palladium on carbon, palladium hydroxide on carbon, or platinum on carbon. Examples of suitable solvents include: $NH_3$-MeOH, MeOH, EtOH, or EtOAc. Reaction temperatures are generally in the range of from $20°$ C. to $100°$ C., preferably in the range of from $20°$ C. to $60°$ C. Reaction times are, in general, from 10 minutes to 96 hrs, preferably from 30 minutes to 24 hr. Reaction can be carried out under an applied pressure of 1 atm to 4 atm.

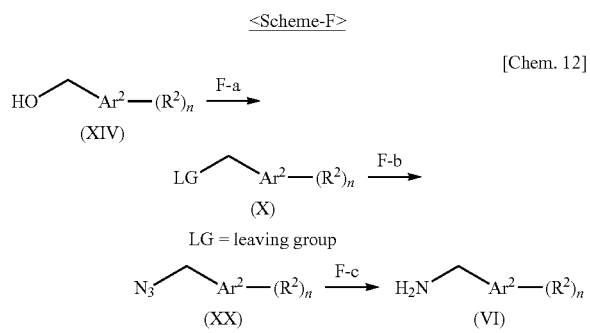

<Scheme-F>

[Chem. 12]

LG = leaving group

When LG is such as O-trifluoromethanesulfonate, O-tosylate, O-mesylate, iodide, bromide, or chloride, in Step F-a, a compound of formula (X) can be prepared by sulfonylation or substitution with halogen of a compound of formula (XIV) under, for example, known sulfonylation condition or known halogenation conditions in an inert solvent. In case of sulfonylation, the reaction can be carried out by the method described in Step A-a. In case of halogenation, example of halogen source is such as thionyl chloride, N-bromosuccinimide, N-chlorosuccinimide, iodine, bromine, phosphorous trichloride, phosphorous tribromide, carbontetrachloride, or carbontetrabromide. In the halogenation reaction, the reaction can be carried out in the presence of reducing agent such as triphenylphosphine. Examples of suitable organic solvent include: THF, 1,4-dioxane, DCM, 1,2-dichloroethane, carbontetrachloride, toluene, or DMF.

In Step F-b, a compound of formula (XX) can be prepared by substitution reaction with azide group of a compound of formula (X). The reaction can be carried out with a suitable reagent in an inert solvent. A preferred reagent is selected from, for example, lithium azide, sodium azide, potassium azide, or cesium azide. Reaction temperatures are generally in the range of from 20° C. to 150° C., preferably in the range of from 50° C. to 120° C. Reaction times are, in general, from 30 minutes to 96 hrs, preferably from 1 hrs to 24 hrs. Examples of suitable solvents include: THF, 1,4-dioxane, DMF, MeCN, or DMSO.

In Step F-c, a compound of formula (VI) can be prepared from a compound of formula of (XX) by hydrogenation reaction by the method described in Step E-f above.

All starting materials in the following general syntheses may be commercially available or obtained by conventional methods known to those skilled in the art. The key intermediate methyl 4-(chlorosulfonyl)benzoate can be prepared by the method described in Chemistry & Biology (2002) 9, 113.

Example 1

4-(N-(Benzofuran-5-ylmethyl)-N-(3-chloro-5-(trifluoromethyl)pyridin-2-yl)sulfamoyl)benzoic acid Step-1: Methyl 4-(N-(benzofuran-5-ylmethyl)sulfamoyl)benzoate To a solution of benzofuran-5-ylmethanamine (6.5 g, 28 mmol) in DCM (100 mL) was added methyl 4-(chlorosulfonyl)benzoate (4.1 g, 28 mmol) in portion wise at 0° C., and the mixture was stirred at room temperature for 3 hrs. The mixture was added 2 M aqueous HCl (80 mL) to give a white suspension. A half volume of DCM was removed by nitrogen flow, and the precipitates were collected by filtration, washed with water, and the solid was dried in vacuo at 50° C. to give 5.3 g (55% yield) of the titled compound as a off-white solid. The filtrate formed a suspension, which was collected by filtration, washed with water, and the solid was dried in vacuo at 50° C. to give 3.4 g (35% yield) of the titled compound as a pale brown white solid.

$^1$H-NMR (300 MHz, CDCl$_3$) δ 8.16 (2H, d, J=8.8 Hz), 7.93 (2H, d, J=8.8 Hz), 7.62 (1H, d, J=3.1 Hz), 7.64-7.60 (2H, m), 7.09 (1H, d, J=8.0 Hz), 6.70 (1H, s), 4.78-4.65 (1H, m), 4.26 (2H, d, J=6.6 Hz), 3.97 (3H, s).

LC-MS (method-B) m/z: M−1 obs 344.23; tR=2.92 min.

Step-2: Methyl 4-(N-(benzofuran-5-ylmethyl)-N-(3-chloro-5-(trifluoromethyl)pyridin-2-yl)sulfamoyl) benzoate Methyl 4-(N-(benzofuran-5-ylmethyl)sulfamoyl)benzoate (step-1 of Example 1, 1.0 g, 2.9 mmol), 2,3-dichloro-5-(trifluoromethyl)pyridine (750 mg, 3.5 mmol), and Cs$_2$CO$_3$ (1.1 g, 3.5 mmol) were combined in the microwave vessel. The mixture was added MeCN (22 mL), and was irradiated with microwave at 160° C. for 15 min. The reaction was conducted in three vessels, independently. All reaction mixtures were combined, and filtered through a pad of Celite (registered trademark), washed with DCM, and the filtrate was concentrated to give a clear semi-solid. The residual semi-solid was purified by column chromatography on silica gel (hexane/EtOAc=9/1 to 7/1) to give 2.5 g of yellow solid. The residual solid was triturated with IPE (50 mL), collected by filtration, washed with IPE, and dried in vacuo at 50° C. to give 2.3 g (50% yield) of the titled compound as a white powder.

$^1$H-NMR (300 MHz, CDCl$_3$) δ 8.53 (1H, s), 8.17 (2H, d, J=8.8 Hz), 7.79-7.77 (3H, m), 7.56 (1H, s), 7.40 (1H, s), 7.30 (1H, d, J=8.8 Hz), 7.16 (1H, d, J=8.8 Hz), 6.65 (1H, s), 4.78 (2H, s), 3.99 (3H, s).

LC-MS (method-D) m/z: M+1 obs 525.24; tR=4.24 min.

Step-3: 4-(N-(Benzofuran-5-ylmethyl)-N-(3-chloro-5-(trifluoromethyl)pyridin-2-yl)sulfamoyl)benzoic acid To a solution of methyl 4-(N-(benzofuran-5-ylmethyl)-N-(3-chloro-5-(trifluoromethyl)pyridin-2-yl)sulfamoyl)benzoate (step-2 of Example 1, 2.3 g, 4.3 mmol) in THF (15 mL) was added 2 M aqueous NaOH (9.0 mL) at room temperature, and the mixture was heated at 60° C. for 2 hrs. The mixture was cooled with ice bath, and acidified by the addition of 2 M aqueous HCl (10 mL). The mixture was extracted with DCM (30 mL×2), dried over Na$_2$SO$_4$, filtered and the filtrate was concentrated to give a white solid. The residual solid was triturated with IPE (50 mL), the precipitates were collected by filtration, washed with IPE, and dried in vacuo at 50° C. to give 1.6 g (74% yield) of the titled compound as a white powder.

$^1$H-NMR (300 MHz, CDCl$_3$) δ 8.58 (1H, s), 8.25 (2H, d, J=8.8 Hz), 7.95-7.90 (3H, m), 7.57 (1H, d, J=2.2 Hz), 7.43 (1H, s), 7.33 (1H, d, J=8.8 Hz), 7.18 (1H, dd, J=8.8, 1.5 Hz), 6.65 (1H, d, J=2.2 Hz), 4.83 (2H, s). Signal due to CO$_2$H was not observed.

LC-MS (method-D) m/z: M+1 obs 511.21, M−1 obs 509.26; tR=3.74 min.

The further purification was carried out by preparative LC-MS system in usual manner.

HPLC-QC method, retention time and observed MS were summarized in Table 1.

Example 2

4-(N-(Benzofuran-6-ylmethyl)-N-(3-chloro-5-(trifluoromethyl)pyridin-2-yl)sulfamoyl)benzoic acid Step-1: Methyl 4-(N-(benzofuran-6-ylmethyl)sulfamoyl)benzoate The titled compound was prepared according to the procedure described in step-1 of Example 1 from methyl 4-(chlorosulfonyl)benzoate and benzofuran-6-ylmethanamine.

$^1$H-NMR (300 MHz, CDCl$_3$) δ 8.13 (2H, d, J=8.8 Hz), 7.92 (2H, d, J=8.8 Hz), 7.60 (1H, d, J=2.2 Hz), 7.48 (1H, d, J=8.1 Hz), 7.33 (1H, s), 7.06 (1H, dd, J=8.1, 1.5 Hz), 6.72 (1H, d, J=2.2 Hz), 4.96 (1H, t, J=5.9 Hz), 4.28 (2H, d, J=5.9 Hz), 3.95 (3H, s).

LC-MS (method-B) m/z: M−1 obs 344.23; tR=2.93 min.

Step-2: Methyl 4-(N-(benzofuran-6-ylmethyl)-N-(3-chloro-5-(trifluoromethyl)pyridin-2-yl)sulfamoyl)benzoate The titled compound was prepared according to the procedure described in step-2 of Example 1 from 2,3-dichloro-5-(trifluoromethyl)pyridine and methyl 4-(N-(benzofuran-6-ylmethyl)sulfamoyl)benzoate (step-1 of Example 2).

$^1$H-NMR (300 MHz, CDCl$_3$) δ 8.53 (1H, d, J=2.2 Hz), 8.21 (2H, d, J=8.8 Hz), 7.92 (1H, d, J=2.2 Hz), 7.89 (2H, d, J=8.8 Hz), 7.56 (1H, d, J=2.2 Hz), 7.41 (1H, d, J=8.0 Hz), 7.33 (1H, s), 7.12 (1H, d, J=8.0 Hz), 6.67 (1H, d, J=2.2 Hz), 4.81 (2H, s), 3.99 (3H, s).

LC-MS (method-D) m/z: M+1 obs 525.24; tR=4.24 min.

Step-3: 4-(N-(Benzofuran-6-ylmethyl)-N-(3-chloro-5-(trifluoromethyl)pyridin-2-yl)sulfamoyl)benzoic acid The titled compound was prepared according to the procedure described in step-3 of Example 1 from methyl 4-(N-(benzofuran-6-ylmethyl)-N-(3-chloro-5-(trifluoromethyl)pyridin-2-yl)sulfamoyl)benzoate (step-2 of Example 2).

$^1$H-NMR (300 MHz, CDCl$_3$) δ 8.57 (1H, s), 8.26 (2H, d, J=8.8 Hz), 7.95 (1H, d, J=3.0 Hz), 7.93 (2H, d, J=8.8 Hz), 7.57 (1H, d, J=2.2 Hz), 7.42 (1H, d, J=8.1 Hz), 7.35 (1H, s), 7.13 (1H, dd, J=8.1, 1.5 Hz), 6.69 (1H, d, J=2.2 Hz), 4.85 (2H, s). Signal due to CO$_2$H was not observed.

LC-MS (method-D) m/z: M+1 obs 511.24, M−1 obs 509.24; tR=3.73 min.

The further purification was carried out by preparative LC-MS system in usual manner.

HPLC-QC method, retention time and observed MS were summarized in Table 1.

Example 3

4-(N-(3-Chloro-5-(trifluoromethyl)pyridin-2-yl)-N-((1-methyl-1H-indazol-5-yl)methyl)sulfamoyl)benzoic acid Step-1: Methyl 4-(N-((1-methyl-1H-indazol-5-yl)methyl)sulfamoyl)benzoate The titled compound was prepared according to the procedure described in step-1 of Example 1 from (1-methyl-1H-indazol-5-yl)methanamine.

$^1$H-NMR (300 MHz, CDCl$_3$) δ 8.14 (2H, d, J=8.8 Hz), 7.94-7.89 (3H, m), 7.51 (1H, s), 7.32-7.20 (2H, m), 4.88 (1H, t, J=5.9 Hz), 4.27 (2H, d, J=5.9 Hz), 4.05 (3H, s), 3.98 (3H, s).

LC-MS (method-A) m/z: M+1 obs 360.00, M−1 obs 358.06; tR=2.75 min.

Step-2: Methyl 4-(N-(3-chloro-5-(trifluoromethyl)pyridin-2-yl)-N-((1-methyl-1H-indazol-5-yl)methyl)sulfamoyl)benzoate The titled compound was prepared according to the procedure described in step-2 of Example 1 from 2,3-dichloro-5-(trifluoromethyl)pyridine and methyl 4-(N-((1-methyl-1H-indazol-5-yl)methyl)sulfamoyl)benzoate (step-1 of Example 3).

$^1$H-NMR (300 MHz, CDCl$_3$) δ 8.53 (1H, s), 8.22 (2H, d, J=9.5 Hz), 7.90-7.80 (4H, m), 7.40-7.35 (2H, m), 7.26-7.23 (1H, m), 4.79 (2H, s), 4.01 (3H, s), 4.00 (3H, s).

LC-MS (method-A) m/z: M+1 obs 538.92; tR=3.30 min.

Step-3: 4-(N-(3-Chloro-5-(trifluoromethyl)pyridin-2-yl)-N-((1-methyl-1H-indazol-5-yl)methyl)sulfamoyl)benzoic acid The titled compound was prepared according to the procedure described in step-3 of Example 1 from methyl 4-(N-(3-chloro-5-(trifluoromethyl)pyridin-2-yl)-N-((1-methyl-1H-indazol-5-yl)methyl)sulfamoyl)benzoate (step-2 of Example 3) without trituration.

LC-MS (method-A) m/z: M+1 obs 524.81, M−1 obs 522.79; tR=2.90 min.

The further purification was carried out by preparative LC-MS system in usual manner. HPLC-QC method, retention time and observed MS were summarized in Table 1.

Example 4

4-(N-(3-Chloro-5-(trifluoromethyl)pyridin-2-yl)-N-((1-methyl-1H-indazol-5-yl)methyl)sulfamoyl)-3-ethylbenzoic acid Step-1: 4-Bromo-2-ethyl-N-((1-methyl-1H-indazol-5-yl)methyl)benzenesulfonamide The titled compound was prepared according to the procedure described in step-1 of Example 1 from (1-methyl-1H-indazol-5-yl)methanamine and 4-bromo-2-ethylbenzene-1-sulfonyl chloride.

$^1$H-NMR (300 MHz, CDCl$_3$) δ 7.91 (1H, s), 7.81 (1H, d, J=8.8 Hz), 7.49 (2H, s), 7.39 (1H, dd, J=8.8, 1.5 Hz), 7.29 (1H, d, J=8.8 Hz), 7.19 (1H, dd, J=8.8, 1.5 Hz), 4.79 (1H, t, J=5.9 Hz), 4.24 (2H, d, J=5.9 Hz), 4.06 (3H, s), 2.99 (2H, q, J=7.6 Hz), 1.28 (3H, t, J=7.6 Hz).

LC-MS (method-A) m/z: M+1 obs 408.16; tR=3.22 min.

Step-2: Methyl 3-ethyl-4-(N-((1-methyl-1H-indazol-5-yl)methyl)sulfamoyl)benzoate A mixture of 4-bromo-2-ethyl-N-((1-methyl-1H-indazol-5-yl)methyl)benzenesulfonamide (prepared in step-1 of Example 4, 263 mg, 0.64 mmol), palladium(II) acetate (43 mg, 0.19 mmol), 1,3-bis(diphenylphosphino)propane (80 mg, 0.19 mmol) and triethylamine (130 mg, 1.29 mmol) in the mixture of DMF (7 mL)-MeOH (2.8 mL) was stirred at 100° C. for 1 day under carbon monooxide atmosphere. Then, to the mixture was added palladium(II) acetate (43 mg, 0.19 mmol), 1,3-bis(diphenylphosphino)propane (80 mg, 0.19 mmol). The mixture was stirred at 100° C. for 2 hrs under carbon monoxide atmosphere. The mixture was poured into EtOAc-hexane (2:1) and washed with 2 M aqueous HCl and H₂O. The organic layer was dried over Na₂SO₄, filtered and concentrated. The residual solid was purified by silicagel column chromatography (0-40% EtOAc in hexane) to give titled compound (160 mg, 64%) as a white solid.

$^1$H-NMR (300 MHz, CDCl₃) δ 8.00-8.05 (2H, m), 7.85-7.92 (2H, m), 7.49 (1H, s), 7.29 (1H, d, J=8.8 Hz), 7.20 (1H, dd, J=8.8, 1.8 Hz), 4.94 (1H, m), 4.25 (2H, d, J=5.9 Hz), 4.04 (3H, s), 3.96 (3H, s), 3.06 (2H, q, J=7.6 Hz), 1.31 (3H, t, J=7.6 Hz).

LC-MS (method-A) m/z: M+1 obs 388.28; tR=3.02 min.

Step-3: Methyl 4-(N-(3-chloro-5-(trifluoromethyl)pyridin-2-yl)-N-((1-methyl-1H-indazol-5-yl)methyl)sulfamoyl)-3-ethylbenzoate The titled compound was prepared according to the procedure described in step-2 of Example 1 from 2,3-dichloro-5-(trifluoromethyl)pyridine and methyl 3-ethyl-4-(N-((1-methyl-1H-indazol-5-yl)methyl)sulfamoyl)benzoate (step-2 of Example 4).

LC-MS (method-A) m/z: M+1 obs 567.20; tR=3.48 min.

Step-4: 4-(N-(3-Chloro-5-(trifluoromethyl)pyridin-2-yl)-N-((1-methyl-1H-indazol-5-yl)methyl)sulfamoyl)-3-ethylbenzoic acid The titled compound was prepared according to the procedure described in step-3 of Example 3 from methyl 4-(N-(3-chloro-5-(trifluoromethyl)pyridin-2-yl)-N-((1-methyl-1H-indazol-5-yl)methyl)sulfamoyl)-3-ethylbenzoate (step-3 of Example 4).

LC-MS (method-A) m/z: M+1 obs 553.19; tR=3.07 min.

The further purification was carried out by preparative LC-MS system in usual manner. HPLC-QC method, retention time and observed MS were summarized in Table 1.

Example 5

4-(N-(Benzofuran-5-ylmethyl)-N-(3,5-dichloropyridin-2-yl)sulfamoyl)benzoic acid

Step-1: Methyl 4-(N-(benzofuran-5-ylmethyl)-N-(3,5-dichloropyridin-2-yl)sulfamoyl)benzoate The titled compound was prepared according to the procedure described in step-2 of Example 1 from 3,5-dichloro-2-fluoropyridine and methyl 4-(N-(benzofuran-5-ylmethyl)sulfamoyl)benzoate (step-1 of Example 1).

LC-MS (method-C) m/z: M+1 obs 490.91; tR=2.77 min.

Step-2: 4-(N-(Benzofuran-5-ylmethyl)-N-(3,5-dichloropyridin-2-yl)sulfamoyl)benzoic acid The titled compound was prepared according to the procedure described in step-3 of Example 3 from methyl 4-(N-(benzofuran-5-ylmethyl)-N-(3,5-dichloropyridin-2-yl)sulfamoyl)benzoate (step-1 of Example 5).

LC-MS (method-A) m/z: M+1 obs 476.92; tR=3.07 min.

The further purification was carried out by preparative LC-MS system in usual manner. HPLC-QC method, retention time and observed MS were summarized in Table 1.

Example 6

4-(N-(3-Chloro-5-(trifluoromethyl)pyridin-2-yl)-N-((1-methyl-1H-indol-5-yl)methyl)sulfamoyl)benzoic acid

Step-1: Methyl 4-(N-((1-methyl-1H-indol-5-yl)methyl)sulfamoyl)benzoate

The titled compound was prepared according to the procedure described in step-1 of Example 1 from methyl 4-(chlorosulfonyl)benzoate and (1-methyl-1H-indol-5-yl)methanamine.

$^1$H-NMR (300 MHz, CDCl₃) δ 8.13 (2H, d, J=8.8 Hz), 7.93 (2H, d, J=8.8 Hz), 7.37 (1H, s), 7.21 (1H, d, J=8.1 Hz), 6.98-7.05 (2H, m), 6.39 (1H, d, J=3.7 Hz), 4.76 (1H, br s), 4.25 (2H, d, J=5.9 Hz), 3.97 (3H, s), 3.76 (3H, s).

LC-MS (method-A) m/z: M+1 obs 359.06; tR=2.98 min.

Step-2: Methyl 4-(N-(3-chloro-5-(trifluoromethyl)pyridin-2-yl)-N-((1-methyl-1H-indol-5-yl)methyl)sulfamoyl)benzoate The titled compound was prepared according to the procedure described in step-2 of Example 1 from 2,3-dichloro-5-(trifluoromethyl)pyridine and methyl 4-(N-((1-methyl-1H-indol-5-yl)methyl)sulfamoyl)benzoate (step-1 of Example 6).

LC-MS (method-A) m/z: M+1 obs 537.86; tR=3.52 min.

Step-3: 4-(N-(3-chloro-5-(trifluoromethyl)pyridin-2-yl)-N-((1-methyl-1H-indol-5-yl)methyl)sulfamoyl)benzoic acid The titled compound was prepared according to the procedure described in step-3 of Example 3 from methyl 4-(N-(3-chloro-5-(trifluoromethyl)pyridin-2-yl)-N-((1-methyl-1H-indol-5-yl)methyl)sulfamoyl)benzoate (step-2 of Example 6).

LC-MS (method-A) m/z: M−1 obs 521.90; tR=3.13 min.

The further purification was carried out by preparative LC-MS system in usual manner. HPLC-QC method, retention time and observed MS were summarized in Table 1.

Example 7

4-(N-(3,5-Dichloropyridin-2-yl)-N-((1-methyl-1H-indol-5-yl)methyl)sulfamoyl)benzoic acid

Step-1: Methyl 4-(N-(3,5-dichloropyridin-2-yl)-N-((1-methyl-1H-indol-5-yl)methyl)sulfamoyl)benzoate The titled compound was prepared according to the procedure described in step-2 of Example 1 from 3,5-dichloro-2-fluoropyridine and methyl 4-(N-((1-methyl-1H-indol-5-yl)methyl)sulfamoyl)benzoate (step-1 of Example 6).

LC-MS (method-C) m/z: M+1 obs 504.94; tR=2.47 min.

Step-2: 4-(N-(3,5-Dichloropyridin-2-yl)-N-((1-methyl-1H-indol-5-yl)methyl)sulfamoyl)benzoic acid The titled compound was prepared according to the procedure described in step-3 of Example 3 from methyl 4-(N-(3, 5-dichloropyridin-2-yl)-N-((1-methyl-1H-indol-5-yl)methyl)sulfamoyl)benzoate (step-1 of Example 7).

LC-MS (method-A) m/z: M+1 obs 490.91; tR=2.84 min.

The further purification was carried out by preparative LC-MS system in usual manner. HPLC-QC method, retention time and observed MS were summarized in Table 1.

Example 8

3-Chloro-4-(N-(3-chloro-5-(trifluoromethyl)pyridin-2-yl)-N-((1-methyl-1H-indol-5-yl)methyl)sulfamoyl)benzoic acid Step-1: Ethyl 3-chloro-4-(N-((1-methyl-1H-indol-5-yl)methyl)sulfamoyl)benzoate The titled compound was prepared according to the procedure described in step-1 of Example 1 from ethyl 3-chloro-4-(chlorosulfonyl)benzoate and (1-methyl-1H-indol-5-yl)methanamine.

LC-MS (method-A) m/z: M+1 obs 407.00; tR=3.18 min.

Step-2: Ethyl 3-chloro-4-(N-(3-chloro-5-(trifluoromethyl)pyridin-2-yl)-N-((1-methyl-1H-indol-5-yl)methyl)sulfamoyl)benzoate The titled compound was prepared according to the procedure described in step-2 of Example 1 from 2,3-dichloro-5-(trifluoromethyl)pyridine and ethyl 3-chloro-4-(N-((1-methyl-1H-indol-5-yl)methyl)sulfamoyl)benzoate (step-1 of Example 8).

LC-MS (method-A) m/z: M+1 obs 585.99; tR=3.75 min.

Step-3: 3-Chloro-4-(N-(3-chloro-5-(trifluoromethyl)pyridin-2-yl)-N-((1-methyl-1H-indol-5-yl)methyl)sulfamoyl)benzoic acid The titled compound was prepared according to the procedure described in step-3 of Example 3 from ethyl 3-chloro-4-(N-(3-chloro-5-(trifluoromethyl)pyridin-2-yl)-N-((1-methyl-1H-indol-5-yl)methyl)sulfamoyl)benzoate (step-2 of Example 8).

LC-MS (method-A) m/z: M+1 obs 557.97; tR=3.08 min.

The further purification was carried out by preparative LC-MS system in usual manner. HPLC-QC method, retention time and observed MS were summarized in Table 1.

Example 9

3-Chloro-4-(N-(3,5-dichloropyridin-2-yl)-N-((1-methyl-1H-indol-5-yl)methyl)sulfamoyl)benzoic acid Step-1: Ethyl 3-chloro-4-(N-(3,5-dichloropyridin-2-yl)-N-((1-methyl-1H-indol-5-yl)methyl)sulfamoyl)benzoate The titled compound was prepared according to the procedure described in step-2 of Example 1 from 3,5-dichloro-2-fluoropyridine and ethyl 3-chloro-4-(N-((1-methyl-1H-indol-5-yl)methyl)sulfamoyl)benzoate (step-1 of Example 8).

Step-2: 3-Chloro-4-(i-(3,5-dichloropyridin-2-yl)-N-((1-methyl-1H-indol-5-yl)methyl)sulfamoyl)benzoic acid The titled compound was prepared according to the procedure described in step-3 of Example 3 from ethyl 3-chloro-4-(N-(3,5-dichloropyridin-2-yl)-N-((1-methyl-1H-indol-5-yl)methyl)sulfamoyl)benzoate (step-1 of Example 9).

LC-MS (method-A) m/z: M−1 obs 521.90; tR=3.02 min.

The further purification was carried out by preparative LC-MS system in usual manner. HPLC-QC method, retention time and observed MS were summarized in Table 1.

Example 10

4-(N-(Benzofuran-6-ylmethyl)-N-(3,5-dichloropyridin-2-yl)sulfamoyl)benzoic acid

Step-1: Methyl 4-(N-(benzofuran-6-ylmethyl)-N-(3,5-dichloropyridin-2-yl)sulfamoyl)benzoate The titled compound was prepared according to the procedure described in step-2 of Example 1 from 3,5-dichloro-2-fluoropyridine and methyl 4-(N-(benzofuran-6-ylmethyl)sulfamoyl)benzoate (step-1 of Example 2). LC-MS (method-C) m/z: M+1 obs 490.91; tR=2.75 min.

Step-2: 4-(N-(Benzofuran-6-ylmethyl)-N-(3,5-dichloropyridin-2-yl)sulfamoyl)benzoic acid The titled compound was prepared according to the procedure described in step-3 of Example 3 from methyl 4-(N-(benzofuran-6-ylmethyl)-N-(3,5-dichloropyridin-2-yl)sulfamoyl)benzoate (step-1 of Example 10).

LC-MS (method-A) m/z: M+1 obs 476.89; tR=3.04 min.

The further purification was carried out by preparative LC-MS system in usual manner. HPLC-QC method, retention time and observed MS were summarized in Table 1.

Example 11

4-(N-(3-Chloro-5-(trifluoromethyl)pyridin-2-yl)-N-((1-methyl-1H-indol-5-yl)methyl)sulfamoyl)-3-methylbenzoic acid Step-1: 4-Bromo-2-methyl-N-((1-methyl-1H-indol-5-yl)methyl)benzenesulfonamide The titled compound was prepared according to the procedure described in step-1 of Example 1 from 4-bromo-2-methylbenzene-1-sulfonyl chloride and (1-methyl-1H-indol-5-yl)methanamine.

LC-MS (method-A) m/z: M+1 obs 394.96; tR=3.25 min.

Step-2: Methyl 3-methyl-4-(N-((1-methyl-1H-indol-5-yl)methyl)sulfamoyl)benzoate

The titled compound was prepared according to the procedure described in step-2 of Example 4 from 4-bromo-2-methyl-N-((1-methyl-1H-indol-5-yl)methyl)benzenesulfonamide (step-1 of Example 11).

LC-MS (method-A) m/z: M+1 obs 373.10; tR=3.08 min.

Step-3: Methyl 4-(N-(3-chloro-5-(trifluoromethyl)pyridin-2-yl)-N-((1-methyl-1H-indol-5-yl)methyl)sulfamoyl)-3-methylbenzoate The titled compound was prepared according to the procedure described in step-2 of Example 1 from 2,3-dichloro-5-(trifluoromethyl)pyridine and methyl 3-methyl-4-(N-((1-methyl-1H-indol-5-yl)methyl)sulfamoyl)benzoate (step-2 of Example 11).

LC-MS (method-A) m/z: M+1 obs 552.02; tR=3.62 min.

Step-4: 4-(N-(3-chloro-5-(trifluoromethyl)pyridin-2-yl)-N-((1-methyl-1H-indol-5-yl)methyl)sulfamoyl)-3-methylbenzoic acid The titled compound was prepared according to the procedure described in step-3 of Example 3 from methyl 4-(N-(3-chloro-5-(trifluoromethyl)pyridin-2-yl)-N-((1-methyl-1H-indol-5-yl)methyl)sulfamoyl)-3-methylbenzoate (step-3 of Example 11).

LC-MS (method-A) m/z: M−1 obs 535.91; tR=3.20 min.

The further purification was carried out by preparative LC-MS system in usual manner. HPLC-QC method, retention time and observed MS were summarized in Table 1.

Example 12

4-(N-(3,5-Dichloropyridin-2-yl)-N-((1-methyl-1H-indol-5-yl)methyl)sulfamoyl)-3-methylbenzoic acid

Step-1: Methyl 4-(N-(3,5-dichloropyridin-2-yl)-N-((1-methyl-1H-indol-5-yl)methyl)sulfamoyl)-3-methylbenzoate The titled compound was prepared according to the procedure described in step-2 of Example 1 from 3,5-dichloro-2-fluoropyridine and methyl 3-methyl-4-(N-((1-methyl-1H-indol-5-yl)methyl)sulfamoyl)benzoate (step-2 of Example 11).

LC-MS (method-A) m/z: M+1 obs 517.93; tR=3.50 min.

Step-2: 4-(N-(3,5-Dichloropyridin-2-yl)-N-((1-methyl-1H-indol-5-yl)methyl)sulfamoyl)-3-methylbenzoic acid The titled compound was prepared according to the procedure described in step-3 of Example 3 from methyl 4-(N-(3,5-dichloropyridin-2-yl)-N-((1-methyl-1H-indol-5-yl)methyl)sulfamoyl)-3-methylbenzoate (step-1 of Example 12).

LC-MS (method-A) m/z: M−1 obs 501.95; tR=3.10 min.

The further purification was carried out by preparative LC-MS system in usual manner. HPLC-QC method, retention time and observed MS were summarized in Table 1.

Example 13

4-(N-(3-Chloro-5-(trifluoromethyl)pyridin-2-yl)-N-((2-ethyl-2H-indazol-5-yl)methyl)sulfamoyl)benzoic acid

Step-1: Ethyl 2-ethyl-2H-indazole-5-carboxylate and ethyl 1-ethyl-1H-indazole-5-carboxylate To a suspension of 1H-indazole-5-carboxylic acid (500 mg, 3.08 mmol) and $Cs_2CO_3$ (2.01 g, 6.17 mmol) in DMF (10 mL) was added iodoethane (1.92 g, 12.33 mmol) at room temperature. The mixture was stirred at room temperature for 1 day. The mixture was poured into $H_2O$, extracted with EtOAc, dried over $Na_2SO_4$, filtered and concentrated. The residual oil was purified by silica gel column chromatography (0-60% EtOAc in hexane) to give ethyl 2-ethyl-2H-indazole-5-carboxylate (208 mg, 31%) as a white solid and ethyl 1-ethyl-1H-indazole-5-carboxylate (435 mg, 65%) as a white solid.

Ethyl 2-ethyl-2H-indazole-5-carboxylate $^1$H-NMR (300 MHz, $CDCl_3$) δ 8.50 (1H, s), 8.08 (1H, s), 7.92 (1H, d, J=8.8, 1.5 Hz), 7.70 (1H, d, J=8.8 Hz), 4.51 (2H, q, J=7.3 Hz), 4.40 (2H, q, J=7.1 Hz), 1.66 (3H, t, J=7.3 Hz), 1.42 (3H, t, J=7.1 Hz).

LC-MS (method-A) m/z: M+1 obs 219.23; tR=2.68 min.

Ethyl 1-ethyl-1H-indazole-5-carboxylate $^1$H-NMR (300 MHz, $CDCl_3$) δ 8.52 (1H, s), 8.10 (1H, s), 8.07 (1H, d, J=8.8, 1.5 Hz), 7.42 (1H, d, J=8.8 Hz), 4.46 (2H, q, J=7.3 Hz), 4.41 (2H, q, J=7.3 Hz), 1.54 (3H, t, J=7.3 Hz), 1.43 (3H, t, J=7.3 Hz).

LC-MS (method-A) m/z: M+1 obs 219.23; tR=2.87 min.

Step-2: (2-Ethyl-2H-indazol-5-yl)methanol

To a solution of ethyl 2-ethyl-2H-indazole-5-carboxylate (step-1 of Example 13, 150 mg, 0.69 mmol) in THF (10 mL) was added $LiAlH_4$ (26 mg, 0.69 mmol) at 0° C. The mixture was stirred at room temperature for 1 hr. The mixture was quenched with saturated aqueous $NH_4Cl$. The precipitate was filtered off. The filtrate was concentrated to give the titled compound (131 mg, quant) as an orange colored oil.

$^1$H-NMR (300 MHz, $CDCl_3$) δ 7.90 (1H, s), 7.68 (1H, d, J=8.8 Hz), 7.61 (1H, s), 7.28 (1H, d, J=8.8 Hz), 4.74 (2H, s), 4.46 (2H, q, J=7.3 Hz), 1.64 (3H, t, J=7.3 Hz). Signal due to OH was not observed.

LC-MS (method-A) m/z: M+1 obs 177.31; tR=1.72 min.

Step-3: 2-((2-Ethyl-2H-indazol-5-yl)methyl)isoindoline-1,3-dione

To a solution of (2-ethyl-2H-indazol-5-yl)methanol (step-2 of Example 13, 132 mg, 0.75 mmol) in THF (10 mL) was added triphenylphosphine (236 mg, 0.90 mmol) and phthalimide (132 mg, 0.90 mmol). The mixture was cooled to 0° C. Then, to the mixture was added 40% DEAD in toluene (0.30 mL, 0.75 mmol) and allowed to warm up to room temperature. The mixture was stirred at room temperature for 4 hrs. The reaction mixture was evaporated. The residual oil was purified by silica gel column chromatography (0-50% EtOAc in hexane) to give the titled compound as a mixture. The mixture was used next step without further purification.

Step-4: (2-Ethyl-2H-indazol-5-yl)methanamine

To a suspension of 2-((2-ethyl-2H-indazol-5-yl)methyl) isoindoline-1,3-dione (step-3 of Example 13, mixture) in MeOH (7 mL) was added hydrazine-$H_2O$ (0.5 mL), and the mixture was heated at 50° C. for 4 hrs. The mixture was concentrated, the residual white solid was added 2 M aqueous NaOH, and extracted with DCM, dried over $Na_2SO_4$, filtered and concentrated. The residual oil was diluted with MeOH and applied onto a strong cation exchange cartridge (Bond-Elute (registered trademark) SCX, 1 g/6 mL, Varian Inc.), and the solid phase matrix was rinsed with MeOH (6 mL). The crude mixture was eluted with 1 M $NH_3$ in MeOH (6 mL) and concentrated to give 68 mg (52% yield in 2 steps) of the titled compound as a colorless oil.

LC-MS (method-A) m/z: M+1 obs 176.3; tR=0.82 min.

Step-5: Methyl 4-(N-((2-ethyl-2H-indazol-5-yl)methyl)sulfamoyl)benzoate

The titled compound was prepared according to the procedure described in step-1 of Example 1 from methyl 4-(chlorosulfonyl)benzoate and (2-ethyl-2H-indazol-5-yl)methanamine (step-4 of Example 13).

$^1$H-NMR (300 MHz, CDCl$_3$) δ 8.14 (2H, d, J=8.8 Hz), 7.93 (2H, d, J=8.8 Hz), 7.86 (1H, s), 7.61 (1H, d, J=8.8 Hz), 7.46 (1H, s), 7.05 (1H, dd, J=8.8, 1.5 Hz), 4.81 (1H, t, J=5.9 Hz), 4.46 (2H, q, J=7.3 Hz), 4.24 (2H, d, J=5.9 Hz), 3.97 (3H, s), 1.63 (3H, t, J=7.3 Hz).

LC-MS (method-A) m/z: M+1 obs 374.09; tR=2.70 min.

Step-6: Methyl 4-(N-(3-chloro-5-(trifluoromethyl)pyridin-2-yl)-N-((2-ethyl-2H-indazol-5-yl)methyl)sulfamoyl)benzoate The titled compound was prepared according to the procedure described in step-2 of Example 1 from 2,3-dichloro-5-(trifluoromethyl)pyridine and methyl 4-(N-((2-ethyl-2H-indazol-5-yl)methyl)sulfamoyl)benzoate (step-5 of Example 13).

LC-MS (method-A) m/z: M+1 obs 552.97; tR=3.39 min.

Step-7: 4-(N-(3-Chloro-5-(trifluoromethyl)pyridin-2-yl)-N-((2-ethyl-2H-indazol-5-yl)methyl)sulfamoyl)benzoic acid The titled compound was prepared according to the procedure described in step-3 of Example 3 from methyl 4-(N-(3-chloro-5-(trifluoromethyl)pyridin-2-yl)-N-((2-ethyl-2H-indazol-5-yl)methyl)sulfamoyl)benzoate (step-6 of Example 13).

LC-MS (method-A) m/z: M+1 obs 538.93; tR=2.97 min.

The further purification was carried out by preparative LC-MS system in usual manner. HPLC-QC method, retention time and observed MS were summarized in Table 1.

Example 14

3-Chloro-4-(N-(3-chloro-5-(trifluoromethyl)pyridin-2-yl)-N-((1-ethyl-1H-indazol-5-yl)methyl)sulfamoyl)benzoic acid

Step-1: (1-Ethyl-1H-indazol-5-yl)methanol

The titled compound was prepared according to the procedure described in step-2 of Example 13 from ethyl 1-ethyl-1H-indazole-5-carboxylate (step-1 of Example 13).

$^1$H-NMR (300 MHz, CDCl$_3$) δ 7.96 (1H, s), 7.70 (1H, s), 7.41 (2H, s), 4.78 (2H, s), 4.43 (2H, q, J=7.3 Hz), 1.51 (3H, t, J=7.3 Hz). Signal due to OH was not observed.

LC-MS (method-A) m/z: M+1 obs 177.31; tR=2.15 min.

Step-2: 2-((1-Ethyl-1H-indazol-5-yl)methyl)isoindoline-1,3-dione

The titled compound was prepared according to the procedure described in step-3 of Example 13 from (1-ethyl-1H-indazol-5-yl)methanol (step-1 of Example 14).

LC-MS (method-A) m/z: M+1 obs 306.31; tR=2.93 min.

Step-3: (1-Ethyl-1H-indazol-5-yl)methanamine

The titled compound was prepared according to the procedure described in step-4 of Example 13 from 2-((1-ethyl-1H-indazol-5-yl)methyl)isoindoline-1,3-dione (step-2 of Example 14).

LC-MS (method-A) m/z: M+1 obs 176.29; tR=0.67 min.

Step-4: Ethyl 3-chloro-4-(N-((1-ethyl-1H-indazol-5-yl)methyl)sulfamoyl)benzoate The titled compound was prepared according to the procedure described in step-1 of Example 1 from ethyl 3-chloro-4-(chlorosulfonyl)benzoate and (1-ethyl-1H-indazol-5-yl)methanamine (step-3 of Example 14).

LC-MS (method-A) m/z: M+1 obs 422.07; tR=3.00 min.

Step-5: Ethyl 3-chloro-4-(N-(3-chloro-5-(trifluoromethyl)pyridin-2-yl)-N-((1-ethyl-1H-indazol-5-yl)methyl)sulfamoyl)benzoate The titled compound was prepared according to the procedure described in step-2 of Example 1 from 2,3-dichloro-5-(trifluoromethyl)pyridine and ethyl 3-chloro-4-(N-((1-ethyl-1H-indazol-5-yl)methyl)sulfamoyl)benzoate (step-4 of Example 14).

LC-MS (method-A) m/z: M+1 obs 600.93; tR=3.75 min.

Step-6: 3-Chloro-4-(N-(3-chloro-5-(trifluoromethyl)pyridin-2-yl)-N-((1-ethyl-1H-indazol-5-yl)methyl)sulfamoyl)benzoic acid The titled compound was prepared according to the procedure described in step-3 of Example 3 from ethyl 3-chloro-4-(N-(3-chloro-5-(trifluoromethyl)pyridin-2-yl)-N-((1-ethyl-1H-indazol-5-yl)methyl)sulfamoyl)benzoate (step-5 of Example 14).

LC-MS (method-A) m/z: M+1 obs 572.87; tR=3.07 min.

The further purification was carried out by preparative LC-MS system in usual manner. HPLC-QC method, retention time and observed MS were summarized in Table 1.

Example 15

4-(N-(3-Chloro-5-(trifluoromethyl)pyridin-2-yl)-N-((1-ethyl-1H-indazol-5-yl)methyl)sulfamoyl)benzoic acid

Step-1: Methyl 4-(N-((1-ethyl-1H-indazol-5-yl)methyl)sulfamoyl)benzoate

The titled compound was prepared according to the procedure described in step-1 of Example 1 from methyl 4-(chlorosulfonyl)benzoate and (1-ethyl-1H-indazol-5-yl)methanamine (step-3 of Example 14).

$^1$H-NMR (300 MHz, CDCl$_3$) δ 8.13 (2H, d, J=8.8 Hz), 7.91 (2H, d, J=8.8 Hz), 7.89 (1H, s), 7.51 (1H, s), 7.32 (1H, d, J=8.8 Hz), 7.21 (1H, d, J=8.8 Hz), 4.91 (1H, t, J=5.9 Hz), 4.40 (2H, q, J=7.1 Hz), 4.27 (2H, d, J=5.9 Hz), 3.97 (3H, s), 1.48 (3H, t, J=7.1 Hz).

LC-MS (method-A) m/z: M+1 obs 374.09; tR=2.82 min.

Step-2: Methyl 4-(N-(3-chloro-5-(trifluoromethyl)pyridin-2-yl)-N-((1-ethyl-1H-indazol-5-yl)methyl)sulfamoyl)benzoate The titled compound was prepared according to the procedure described in step-2 of Example 1 from 2,3-dichloro-5-

(trifluoromethyl)pyridine and methyl 4-(N-((1-ethyl-1H-indazol-5-yl)methyl)sulfamoyl)benzoate (step-1 of Example 15).

LC-MS (method-A) m/z: M+1 obs 552.97; tR=3.52 min.

Step-3: 4-(N-(3-Chloro-5-(trifluoromethyl)pyridin-2-yl)-N-((1-ethyl-1H-indazol-5-yl)methyl)sulfamoyl) benzoic acid The titled compound was prepared according to the procedure described in step-3 of Example 3 from ethyl 3-chloro-4-(N-(3-chloro-5-(trifluoromethyl)pyridin-2-yl)-N-((1-ethyl-1H-indazol-5-yl)methyl)sulfamoyl)benzoate (step-2 of Example 15).

LC-MS (method-A) m/z: M+1 obs 538.84; tR=3.00 min.

The further purification was carried out by preparative LC-MS system in usual manner. HPLC-QC method, retention time and observed MS were summarized in Table 1.

Example 16

4-(N-(3-Chloro-5-(trifluoromethyl)pyridin-2-yl)-N-((2-methyl-2H-indazol-5-yl)methyl)sulfamoyl)benzoic acid Step-1: Methyl 4-(N-((2-methyl-2H-indazol-5-yl)methyl)sulfamoyl)benzoate The titled compound was prepared according to the procedure described in step-1 of Example 1 from methyl 4-(chlorosulfonyl)benzoate and (2-methyl-2H-indazol-5-yl)methanamine.

$^1$H-NMR (300 MHz, CDCl$_3$) δ 8.14 (2H, d, J=8.8 Hz), 7.93 (2H, d, J=8.8 Hz), 7.83 (1H, s), 7.59 (1H, d, J=8.8 Hz), 7.45 (1H, s), 7.05 (1H, d, J=8.8 Hz), 4.84 (1H, t, J=5.9 Hz), 4.23 (2H, d, J=5.9 Hz), 4.21 (3H, s), 3.97 (3H, s).

LC-MS (method-A) m/z: M+1 obs 360.07; tR=2.59 min.

Step-2: Methyl 4-(N-(3-chloro-5-(trifluoromethyl) pyridin-2-yl)-N-((2-methyl-2H-indazol-5-yl)methyl) sulfamoyl)benzoate The titled compound was prepared according to the procedure described in step-2 of Example 1 from 2,3-dichloro-5-(trifluoromethyl)pyridine and methyl 4-(N-((2-methyl-2H-indazol-5-yl)methyl)sulfamoyl)benzoate (step-1 of Example 16).

LC-MS (method-A) m/z: M+1 obs 538.94; tR=3.32 min.

Step-3: 4-(N-(3-Chloro-5-(trifluoromethyl)pyridin-2-yl)-N-((2-methyl-2H-indazol-5-yl)methyl)sulfamoyl) benzoic acid The titled compound was prepared according to the procedure described in step-3 of Example 3 from methyl 4-(N-(3-chloro-5-(trifluoromethyl)pyridin-2-yl)-N-((2-methyl-2H-indazol-5-yl)methyl)sulfamoyl)benzoate (step-2 of Example 16).

LC-MS (method-A) m/z: M+1 obs 524.87; tR=2.82 min.

The further purification was carried out by preparative LC-MS system in usual manner. HPLC-QC method, retention time and observed MS were summarized in Table 1.

Example 17

4-(N-(3-Chloro-5-(trifluoromethyl)pyridin-2-yl)-N-((1-methyl-1H-indazol-6-yl)methyl)sulfamoyl)benzoic acid Step-1: Methyl 4-(N-((1-methyl-1H-indazol-6-yl) methyl)sulfamoyl)benzoate The titled compound was prepared according to the procedure described in step-1 of Example 1 from methyl 4-(chlorosulfonyl)benzoate and (1-methyl-1H-indazol-6-yl)methanamine.

LC-MS (method-A) m/z: M+1 obs 360.16; tR=2.73 min.

Step-2: Methyl 4-(N-(3-chloro-5-(trifluoromethyl) pyridin-2-yl)-N-((1-methyl-1H-indazol-6-yl)methyl) sulfamoyl)benzoate The titled compound was prepared according to the procedure described in step-2 of Example 1 from 2,3-dichloro-5-(trifluoromethyl)pyridine and methyl 4-(N-((1-methyl-1H-indazol-6-yl)methyl)sulfamoyl)benzoate (step-1 of Example 17).

LC-MS (method-A) m/z: M+1 obs 539.2; tR=3.34 min.

Step-3: 4-(N-(3-Chloro-5-(trifluoromethyl)pyridin-2-yl)-N-((1-methyl-1H-indazol-6-yl)methyl)sulfamoyl) benzoic acid The titled compound was prepared according to the procedure described in step-3 of Example 3 from methyl 4-(N-(3-chloro-5-(trifluoromethyl)pyridin-2-yl)-N-((1-methyl-1H-indazol-6-yl)methyl)sulfamoyl)benzoate (step-2 of Example 17).

LC-MS (method-A) m/z: M+1 obs 525.00; tR=2.98 min.

The further purification was carried out by preparative LC-MS system in usual manner. HPLC-QC method, retention time and observed MS were summarized in Table 1.

Example 18

4-(N-(vvvvvvvv3-Chloro-5-(trifluoromethyl)pyridin-2-yl)-N-((2-methyl-2H-indazol-6-yl)methyl)sulfamoyl)benzoic acid Step-1: Methyl 4-(N-((2-methyl-2H-indazol-6-yl) methyl)sulfamoyl)benzoate The titled compound was prepared according to the procedure described in step-1 of Example 1 from methyl 4-(chlorosulfonyl)benzoate and (2-methyl-2H-indazol-6-yl)methanamine.

LC-MS (method-A) m/z: M+1 obs 360.16; tR=2.63 min.

Step-2: Methyl 4-(N-(3-chloro-5-(trifluoromethyl) pyridin-2-yl)-N-((2-methyl-2H-indazol-6-yl)methyl) sulfamoyl)benzoate The titled compound was prepared according to the procedure described in step-2 of Example 1 from 2,3-dichloro-5-(trifluoromethyl)pyridine and methyl 4-(N-((2-methyl-2H-indazol-6-yl)methyl)sulfamoyl)benzoate (step-1 of Example 18).

LC-MS (method-A) m/z: M+1 obs 539.2; tR=3.23 min.

Step-3: 4-(N-(3-Chloro-5-(trifluoromethyl)pyridin-2-yl)-N-((2-methyl-2H-indazol-6-yl)methyl)sulfamoyl)benzoic acid The titled compound was prepared according to the procedure described in step-3 of Example 3 from methyl 4-(N-(3-chloro-5-(trifluoromethyl)pyridin-2-yl)-N-((2-methyl-2H-indazol-6-yl)methyl)sulfamoyl)benzoate (step-2 of Example 18).

LC-MS (method-A) m/z: M+1 obs 525.00; tR=2.88 min.

The further purification was carried out by preparative LC-MS system in usual manner. HPLC-QC method, retention time and observed MS were summarized in Table 1.

Example 19

4-(N-(3,5-Dichloropyridin-2-yl)-N-((1-ethyl-1H-indazol-5-yl)methyl)sulfamoyl)benzoic acid Step-1: Methyl 4-(N-(3,5-dichloropyridin-2-yl)-N-((1-ethyl-1H-indazol-5-yl)methyl)sulfamoyl)benzoate The titled compound was prepared according to the procedure described in step-2 of Example 1 from 3,5-dichloro-2-fluoropyridine and methyl 4-(N-((1-ethyl-1H-indazol-5-yl)methyl)sulfamoyl)benzoate (step-1 of Example 15).

LC-MS (method-A) m/z: M+1 obs 519.0; tR=3.49 min.

Step-2: 4-(N-(3,5-Dichloropyridin-2-yl)-N-((1-ethyl-1H-indazol-5-yl)methyl)sulfamoyl)benzoic acid The titled compound was prepared according to the procedure described in step-3 of Example 3 from methyl 4-(N-(3,5-dichloropyridin-2-yl)-N-((1-ethyl-1H-indazol-5-yl)methyl)sulfamoyl)benzoate (step-1 of Example 19).

LC-MS (method-A) m/z: M+1 obs 504.91; tR=2.97 min.

The further purification was carried out by preparative LC-MS system in usual manner. HPLC-QC method, retention time and observed MS were summarized in Table 1.

Example 20

4-(N-(3-Chloro-5-(trifluoromethyl)pyridin-2-yl)-N-((1-(2-methoxyethyl)-1H-indazol-5-yl)methyl)sulfamoyl)benzoic acid Step-1: (1-(2-Methoxyethyl)-1H-indazol-5-yl)methanol The titled compound was prepared according to the procedure described in step-1 and step 2 of Example 13 from 1H-indazole-5-carboxylic acid and 1-bromo-2-methoxyethane.

$^1$H-NMR (300 MHz, CDCl$_3$) δ 7.99 (1H, s), 7.69 (1H, s), 7.48 (1H, d, J=8.1 Hz), 7.41 (1H, dd, J=8.8, 1.5 Hz), 4.79 (2H, d, J=5.9 Hz), 4.55 (2H, t, J=5.5 Hz), 3.83 (2H, t, J=5.5 Hz), 3.29 (3H, s), 1.79 (1H, t, J=5.9 Hz).

LC-MS (method-A) m/z: M+1 obs 207.2; tR=2.10 min.

Step-2: (1-(2-Methoxyethyl)-1H-indazol-5-yl)methanamine

The titled compound was prepared according to the procedure described in step-3 and step-4 of Example 13 from (1-(2-methoxyethyl)-1H-indazol-5-yl)methanol (step-1 of Example 20).

LC-MS (method-A) m/z: M+1 obs 207.22; tR=0.65 min.

Step-3: Methyl 4-(N-((1-(2-methoxyethyl)-1H-indazol-5-yl)methyl)sulfamoyl)benzoate The titled compound was prepared according to the procedure described in step-1 of Example 1 from methyl 4-(chlorosulfonyl)benzoate and (1-(2-methoxyethyl)-1H-indazol-5-yl)methanamine (step-2 of Example 20).

LC-MS (method-A) m/z: M+1 obs 404.15; tR=2.84 min.

Step-4: Methyl 4-(N-(3-chloro-5-(trifluoromethyl)pyridin-2-yl)-N-((1-(2-methoxyethyl)-1H-indazol-5-yl)methyl)sulfamoyl)benzoate The titled compound was prepared according to the procedure described in step-2 of Example 1 from 2,3-dichloro-5-(trifluoromethyl)pyridine and methyl 4-(N-((1-(2-methoxyethyl)-1H-indazol-5-yl)methyl)sulfamoyl)benzoate (step-3 of Example 20).

LC-MS (method-A) m/z: M+1 obs 583.1; tR=3.32 min.

Step-5: 4-(N-(3-Chloro-5-(trifluoromethyl)pyridin-2-yl)-N-((1-(2-methoxyethyl)-1H-indazol-5-yl)methyl)sulfamoyl)benzoic acid The titled compound was prepared according to the procedure described in step-3 of Example 3 from methyl 4-(N-(3-chloro-5-(trifluoromethyl)pyridin-2-yl)-N-((1-(2-methoxyethyl)-1H-indazol-5-yl)methyl)sulfamoyl)benzoate (step-4 of Example 20).

LC-MS (method-A) m/z: M+1 obs 569.07; tR=2.97 min.

The further purification was carried out by preparative LC-MS system in usual manner. HPLC-QC method, retention time and observed MS were summarized in Table 1.

Example 21

4-(N-(3-Chloro-5-(trifluoromethyl)pyridin-2-yl)-N-((1-(tetrahydro-2H-pyran-4-yl)-1H-indazol-5-yl)methyl)sulfamoyl)benzoic acid Step-1: (1-(Tetrahydro-2H-pyran-4-yl)-1H-indazol-5-yl)methanol A mixture of 1H-indazole-5-carboxylic acid (400 mg, 2.47 mmol), 4-chlorotetrahydro-2H-pyran (1.49 g, 12.33 mmol) and Cs$_2$CO$_3$ (2.41 g, 7.40 mmol) in NMP (5 mL) was irradiated with microwave (180° C., 80 min). The mixture was poured into H$_2$O, extracted with EtOAc, dried over Na$_2$SO$_4$, filtered and concentrated. The residual oil was purified by silica gel column chromatography (30-60% EtOAc in hexane), then the mixture was purified by amino gel column chromatography (0-35% EtOAc in hexane) to give tetrahydro-2H-pyran-4-yl 1-(tetrahydro-2H-pyran-4-yl)-1H-indazole-5-carboxylate (198 mg, 24% yield) as a white solid.

The resulting ester was reduced according to the procedure described in step-2 of Example 13 to give the titled compound as an orange oil.

$^1$H-NMR (300 MHz, CDCl$_3$) δ 8.00 (1H, s), 7.72 (1H, s), 7.48 (1H, d, J=8.8 Hz), 7.42 (1H, d, J=8.8 Hz), 4.79 (2H, d, J=5.1 Hz), 4.60-4.70 (1H, m), 4.18 (2H, dd, J=10.6, 3.3 Hz), 3.63 (2H, td, J=11.9, 2.0 Hz), 2.33-2.50 (2H, m), 1.85-2.00 (2H, m). Signal due to OH was not observed.

LC-MS (method-A) m/z: M+1 obs 233.24; tR=2.20 min.

Step-2: (1-(Tetrahydro-2H-pyran-4-yl)-1H-indazol-5-yl)methanamine

The titled compound was prepared according to the procedure described in step-3 and step-4 of Example 13 from (1-(tetrahydro-2H-pyran-4-yl)-1H-indazol-5-yl)methanol (step-1 of Example 21).

LC-MS (method-A) m/z: M+1 obs 233.24; tR=0.94 min.

Step-3: Methyl 4-(N-((1-(tetrahydro-2H-pyran-4-yl)-1H-indazol-5-yl)methyl)sulfamoyl)benzoate The titled compound was prepared according to the procedure described in step-1 of Example 1 from methyl 4-(chlorosulfonyl)benzoate and (1-(tetrahydro-2H-pyran-4-yl)-1H-indazol-5-yl)methanamine (step-2 of Example 21).

LC-MS (method-A) m/z: M+1 obs 430.16; tR=2.89 min.

Step-4: Methyl 4-(N-(3-chloro-5-(trifluoromethyl)pyridin-2-yl)-N-((1-(tetrahydro-2H-pyran-4-yl)-1H-indazol-5-yl)methyl)sulfamoyl)benzoate The titled compound was prepared according to the procedure described in step-2 of Example 1 from 2,3-dichloro-5-(trifluoromethyl)pyridine and methyl 4-(N-(3-chloro-5-(trifluoromethyl)pyridin-2-yl)-N-((1-(tetrahydro-2H-pyran-4-yl)-1H-indazol-5-yl)methyl)sulfamoyl)benzoate (step-3 of Example 21).

LC-MS (method-A) m/z: M+1 obs 609.1; tR=3.35 min

Step-5: 4-(N-(3-Chloro-5-(trifluoromethyl)pyridin-2-yl)-N-((1-(tetrahydro-2H-pyran-4-yl)-1H-indazol-5-yl)methyl)sulfamoyl)benzoic acid The titled compound was prepared according to the procedure described in step-3 of Example 3 from methyl 4-(N-(3-chloro-5-(trifluoromethyl)pyridin-2-yl)-N-((1-(tetrahydro-2H-pyran-4-yl)-1H-indazol-5-yl)methyl)sulfamoyl)benzoate (step-4 of Example 21).

LC-MS (method-A) m/z: M+1 obs 595.09; tR=3.00 min.

The further purification was carried out by preparative LC-MS system in usual manner. HPLC-QC method, retention time and observed MS were summarized in Table 1.

Example 22

4-(N-(3-Chloro-5-(trifluoromethyl)pyridin-2-yl)-N-((1-(2-hydroxy-2-methylpropyl)-1H-indazol-5-yl)methyl)sulfamoyl)benzoic acid

Step-1: 1-(5-(Hydroxymethyl)-1H-indazol-1-yl)-2-methylpropan-2-ol

A mixture of 1H-indazole-5-carboxylic acid (400 mg, 2.47 mmol), 2,2-dimethyloxirane (889 mg, 12.33 mmol) and K$_2$CO$_3$ (1.71 g, 12.33 mmol) in NMP (7 mL) was irradiated with microwave (180° C., 30 min). The mixture was poured into H$_2$O, extracted with EtOAc, dried over Na$_2$SO$_4$, filtered and concentrated. The residual oil was purified by amino gel column chromatography (0-35% EtOAc in hexane) to give 2-hydroxy-2-methylpropyl 1-(2-hydroxy-2-methylpropyl)-1H-indazole-5-carboxylate (468 mg, 62% yield) as a white solid.

The resulting ester was reduced according to the procedure described in step-2 of Example 13 to give the titled compound as a pale yellow solid.

$^1$H-NMR (300 MHz, CDCl$_3$) δ 8.02 (1H, s), 7.72 (1H, s), 7.44 (2H, s), 4.78 (2H, d, J=5.9 Hz), 4.32 (2H, s), 2.14 (1H, t, J=5.9 Hz), 1.21 (6H, s). Signal due to one of the OH was not observed.

LC-MS (method-A) m/z: M+1 obs 221.3; tR=1.95 min.

Step-2: 1-(5-(aminomethyl)-1H-indazol-1-yl)-2-methylpropan-2-ol

The titled compound was prepared according to the procedure described in step-3 and step-4 of Example 13 from 1-(5-(hydroxymethyl)-1H-indazol-1-yl)-2-methylpropan-2-ol (step-1 of Example 22).

Step-3: Methyl 4-(N-((1-(2-hydroxy-2-methylpropyl)-1H-indazol-5-yl)methyl)sulfamoyl)benzoate The titled compound was prepared according to the procedure described in step-1 of Example 1 from methyl 4-(chlorosulfonyl)benzoate and 1-(5-(aminomethyl)-1H-indazol-1-yl)-2-methylpropan-2-ol (step-2 of Example 22).

LC-MS (method-A) m/z: M+1 obs 418.21; tR=2.70 min.

Step-4: Methyl 4-(N-(3-chloro-5-(trifluoromethyl)pyridin-2-yl)-N-((1-(2-hydroxy-2-methylpropyl)-1H-indazol-5-yl)methyl)sulfamoyl)benzoate The titled compound was prepared according to the procedure described in step-2 of Example 1 from 2,3-dichloro-5-(trifluoromethyl)pyridine and methyl 4-(N-((1-(2-hydroxy-2-methylpropyl)-1H-indazol-5-yl)methyl)sulfamoyl)benzoate (step-3 of Example 22).

LC-MS (method-A) m/z: M+1 obs 597.2; tR=3.23 min.

Step-5: 4-(N-(3-Chloro-5-(trifluoromethyl)pyridin-2-yl)-N-((1-(2-hydroxy-2-methylpropyl)-1H-indazol-5-yl)methyl)sulfamoyl)benzoic acid The titled compound was prepared according to the procedure described in step-3 of Example 3 from methyl 4-(N-(3-chloro-5-(trifluoromethyl)pyridin-2-yl)-N-((1-(2-hydroxy-2-methylpropyl)-1H-indazol-5-yl)methyl)sulfamoyl)benzoate (step-4 of Example 22).

LC-MS (method-A) m/z: M+1 obs 583.14; tR=2.85 min.

The further purification was carried out by preparative LC-MS system in usual manner. HPLC-QC method, retention time and observed MS were summarized in Table 1.

Example 23

4-(N-(3,5-Dichloropyridin-2-yl)-N-((1-methyl-1H-indazol-5-yl)methyl)sulfamoyl)-3-ethylbenzoic acid

Step-1: Methyl 4-(N-(3,5-dichloropyridin-2-yl)-N-((1-methyl-1H-indazol-5-yl)methyl)sulfamoyl)-3-ethylbenzoate The titled compound was prepared according to the procedure described in step-2 of Example 1 from 3,5-dichloro-2-fluoropyridine and methyl 3-ethyl-4-(N-((1-methyl-1H-indazol-5-yl)methyl)sulfamoyl)benzoate (step-2 of Example 4).

LC-MS (method-A) m/z: M+1 obs 533.2; tR=3.43 min.

Step-2: 4-(N-(3,5-Dichloropyridin-2-yl)-N-((1-methyl-1H-indazol-5-yl)methyl)sulfamoyl)-3-ethylbenzoic acid The titled compound was prepared according to the procedure described in step-3 of Example 3 from methyl 4-(N-(3, 5-dichloropyridin-2-yl)-N-((1-methyl-1H-indazol-5-yl)methyl)sulfamoyl)-3-ethylbenzoate (step-1 of Example 23).
LC-MS (method-A) m/z: M+1 obs 519.13; tR=3.00 min.
The further purification was carried out by preparative LC-MS system in usual manner. HPLC-QC method, retention time and observed MS were summarized in Table 1.

Example 24

3-Chloro-4-(N-(3,5-dichloropyridin-2-yl)-N-((1-methyl-1H-indazol-5-yl)methyl)sulfamoyl)benzoic acid

Step-1: 4-Bromo-2-chloro-N-((1-methyl-1H-indazol-5-yl)methyl)benzenesulfonamide The titled compound was prepared according to the procedure described in step-1 of Example 1 from 4-bromo-2-chlorobenzene-1-sulfonyl chloride and (1-methyl-1H-indazol-5-yl)methanamine.
LC-MS (method-A) m/z: M+1 obs 415.86, M−1 obs 413.85; tR=2.88 min.

Step-2: Methyl 3-chloro-4-(N-((1-methyl-1H-indazol-5-yl)methyl)sulfamoyl)benzoate The titled compound was prepared according to the procedure described in step-2 of Example 4 from 4-Bromo-2-chloro-N-((1-methyl-1H-indazol-5-yl)methyl)benzenesulfonamide (step-1 of Example 24).
LC-MS (method-A) m/z: M+1 obs 394.02, M−1 obs 391.99; tR=2.77 min.

Step-3: Methyl 3-chloro-4-(N-(3,5-dichloropyridin-2-yl)-N-((1-methyl-1H-indazol-5-yl)methyl)sulfamoyl)benzoate The titled compound was prepared according to the procedure described in step-2 of Example 1 from 3,5-dichloro-2-fluoropyridine and methyl 3-chloro-4-(N-((1-methyl-1H-indazol-5-yl)methyl)sulfamoyl)benzoate (step-2 of Example 24).
LC-MS (method-A) m/z: M+1 obs 540.84; tR=3.35 min.

Step-4: 3-Chloro-4-(N-(3,5-dichloropyridin-2-yl)-N-((1-methyl-1H-indazol-5-yl)methyl)sulfamoyl)benzoic acid The titled compound was prepared according to the procedure described in step-3 of Example 3 from methyl 3-chloro-4-(N-(3,5-dichloropyridin-2-yl)-N-((1-methyl-1H-indazol-5-yl)methyl)sulfamoyl)benzoate (step-3 of Example 24).
LC-MS (method-A) m/z: M+1 obs 540.84; tR=3.35 min.
The further purification was carried out by preparative LC-MS system in usual manner. HPLC-QC method, retention time and observed MS were summarized in Table 1.

Example 25

3-Chloro-4-(N-(3-chloro-5-(trifluoromethyl)pyridin-2-yl)-N-((1-methyl-1H-indazol-5-yl)methyl)sulfamoyl)benzoic acid

Step-1: Methyl 3-chloro-4-(N-(3-chloro-5-(trifluoromethyl)pyridin-2-yl)-N-((1-methyl-1H-indazol-5-yl)methyl)sulfamoyl)benzoate The titled compound was prepared according to the procedure described in step-2 of Example 1 from 2,3-dichloro-5-(trifluoromethyl)pyridine and methyl 3-chloro-4-(N-((1-methyl-1H-indazol-5-yl)methyl)sulfamoyl)benzoate (step-2 of Example 24).
LC-MS (method-A) m/z: M+1 obs 572.90; tR=3.38 min.

Step-2: 3-Chloro-4-(N-(3-chloro-5-(trifluoromethyl)pyridin-2-yl)-N-((1-methyl-1H-indazol-5-yl)methyl)sulfamoyl)benzoic acid The titled compound was prepared according to the procedure described in step-3 of Example 3 from methyl 3-chloro-4-(N-(3-chloro-5-(trifluoromethyl)pyridin-2-yl)-N-((1-methyl-1H-indazol-5-yl)methyl)sulfamoyl)benzoate (step-1 of Example 25).
LC-MS (method-A) m/z: M+1 obs 572.90; tR=3.38 min.
The further purification was carried out by preparative LC-MS system in usual manner. HPLC-QC method, retention time and observed MS were summarized in Table 1.

Example 26

4-(N-(3-Chloro-5-(trifluoromethyl)pyridin-2-yl)-N-((1-methyl-1H-indazol-5-yl)methyl)sulfamoyl)-3-methylbenzoic acid

Step-1: 4-Bromo-2-methyl-N-((1-methyl-1H-indazol-5-yl)methyl)benzenesulfonamide The titled compound was prepared according to the procedure described in step-1 of Example 1 from 4-bromo-2-methylbenzene-1-sulfonyl chloride and (1-methyl-1H-indazol-5-yl)methanamine.
LC-MS (method-A) m/z: M+1 obs 396.03, M−1 393.95; tR=3.09 min.

Step-2: Methyl 3-methyl-4-(N-((1-methyl-1H-indazol-5-yl)methyl)sulfamoyl)benzoate The titled compound was prepared according to the procedure described in step-2 of Example 4 from 4-bromo-2-methyl-N-((1-methyl-1H-indazol-5-yl)methyl)benzenesulfonamide (step-1 of Example 26).
LC-MS (method-A) m/z: M+1 obs 374.11, M−1 372.14; tR=2.79 min.

Step-3: Methyl 4-(N-(3-chloro-5-(trifluoromethyl)pyridin-2-yl)-N-((1-methyl-1H-indazol-5-yl)methyl)sulfamoyl)-3-methylbenzoate The titled compound was prepared according to the procedure described in step-2 of Example 1 from 2,3-dichloro-5-(trifluoromethyl)pyridine and methyl 3-methyl-4-(N-((1-methyl-1H-indazol-5-yl)methyl)sulfamoyl)benzoate (step-2 of Example 26).
LC-MS (method-A) m/z: M+1 obs 553.16; tR=3.55 min.

Step-4: 4-(N-(3-Chloro-5-(trifluoromethyl)pyridin-2-yl)-N-((1-methyl-1H-indazol-5-yl)methyl)sulfamoyl)-3-methylbenzoic acid The titled compound was prepared according to the procedure described in step-3 of Example 3 from methyl 4-(N-(3-chloro-5-(trifluoromethyl)pyridin-2-yl)-N-((1-methyl-1H-indazol-5-yl)methyl)sulfamoyl)-3-methylbenzoate (step-3 of Example 26).
LC-MS (method-A) m/z: M+1 obs 539.03, M−1 obs 536.99; tR=3.02 min.

The further purification was carried out by preparative LC-MS system in usual manner. HPLC-QC method, retention time and observed MS were summarized in Table 1.

Example 27

4-(N-(3,5-Dichloropyridin-2-yl)-N-((1-methyl-1H-indazol-5-yl)methyl)sulfamoyl)-3-methylbenzoic acid Step-1: Methyl 4-(N-(3,5-dichloropyridin-2-yl)-N-((1-methyl-1H-indazol-5-yl)methyl)sulfamoyl)-3-methylbenzoate The titled compound was prepared according to the procedure described in step-2 of Example 1 from 2,3,5-trichloropyridine and methyl 3-methyl-4-(N-((1-methyl-1H-indazol-5-yl)methyl)sulfamoyl)benzoate (step-2 of Example 26).

LC-MS (method-A) m/z: M+1 obs 519.10; tR=3.49 min.

Step-2: 4-(N-(3,5-Dichloropyridin-2-yl)-N-((1-methyl-1H-indazol-5-yl)methyl)sulfamoyl)-3-methylbenzoic acid The titled compound was prepared according to the procedure described in step-3 of Example 3 from methyl 4-(N-(3,5-dichloropyridin-2-yl)-N-((1-methyl-1H-indazol-5-yl)methyl)sulfamoyl)-3-methylbenzoate (step-1 of Example 27).

LC-MS (method-A) m/z: M+1 obs 504.98, M−1 obs 502.94; tR=2.95 min.

The further purification was carried out by preparative LC-MS system in usual manner. HPLC-QC method, retention time and observed MS were summarized in Table 1.

Example 28

4-(N-(3-Chloro-5-(trifluoromethyl)pyridin-2-yl)-N-((1-cyclopropyl-1H-indazol-5-yl)methyl)sulfamoyl)benzoic acid Step-1: Methyl 1-cyclopropyl-1H-indazole-5-carboxylate A mixture of methyl 1H-indazole-5-carboxylate (970 mg, 5.5 mmol), cyclopropylboronic acid (946 mg, 11 mmol), cupper (II) acetate, [2,2']bipyridyl (860 mg, 5.5 mmol) in 1,2-dichloroethane (50 mL) was heated at 70° C. for 2 hrs. The mixture was added saturated aqueous NH$_4$Cl (70 mL) followed by the addition of DCM (30 mL) and water (30 mL), extracted with DCM (30 mL×2), dried over Na2SO4, filtered through a pad of Celite (registered trademark) the filtrate was concentrated to give a pale brown solid, which was purified by column chromatography on silica gel (hexane/EtOAc=8/1) to give 840 mg (71% yield) of the titled compound as a off-white solid.

$^1$H-NMR (300 MHz, CDCl$_3$) δ 8.49 (1H, s), 8.09-8.04 (2H, m), 7.61 (1H, d, J=8.8 Hz), 3.95 (3H, s), 3.70-3.59 (1H, m), 1.30-1.18 (4H, m).

LC-MS (method-A) m/z: M+1 obs 217.27; tR=2.77 min.

Step-2: (1-Cyclopropyl-1H-indazol-5-yl) methanol

To a stirred solution of methyl 1-cyclopropyl-1H-indazole-5-carboxylate (400 mg, 1.8 mmol, step-1 of Example 28) in THF (15 mL) was added LiAlH$_4$ (70 mg, 1.8 mmol) at 0° C. The reaction mixture was stirred for 1 hr at room temperature, and quenched with saturated aqueous NH$_4$Cl (20 mL). The mixture was diluted with DCM (80 mL), dried over Na$_2$SO$_4$, filtered through a pad of Celite (registered trademark) the filtrate was concentrated to give 386 mg (quant.) of the titled compound as pale yellow oil.

$^1$H-NMR (300 MHz, CDCl$_3$) δ 7.91 (1H, s), 7.68 (1H, s), 7.60 (1H, d, J=8.8 Hz), 7.42 (1H, d, J=8.8 Hz), 4.78 (2H, d, J=5.9 Hz), 3.62-3.55 (1H, m), 1.85 (1H, t, J=5.9 Hz), 1.26-1.12 (4H, m).

LC-MS (method-A) m/z: M+1 obs 189.27; tR=2.25 min.

Step-3: 2-((1-Cyclopropyl-1H-indazol-5-yl)methyl)isoindoline-1,3-dione

The titled compound was prepared according to the procedure described in step-3 of Example 13 from isoindoline-1,3-dione and (1-cyclopropyl-1H-indazol-5-yl)methanol (step-2 of Example 28).

LC-MS (method-A) m/z: M+1 obs 318.11; tR=3.00 min.

Step-4: (1-Cyclopropyl-1H-indazol-5-yl)methanamine

The titled compound was prepared according to the procedure described in step-4 of Example 13 from 2-((1-cyclopropyl-1H-indazol-5-yl)methyl)isoindoline-1,3-dione (step-3 of Example 28).

$^1$H-NMR (300 MHz, CDCl$_3$) δ 7.90 (1H, s), 7.62 (1H, s), 7.58 (1H, d, J=8.8 Hz), 7.37 (1H, d, J=8.8 Hz), 3.97 (2H, s), 3.63-3.54 (1H, m), 1.28-1.12 (4H, m). Signal due to NH$_2$ was not observed.

LC-MS (method-A) m/z: M+1 obs 189.21; tR=0.97 min.

Step-5: Methyl 4-(N-((1-cyclopropyl-1H-indazol-5-yl)methyl)sulfamoyl)benzoate

The titled compound was prepared according to the procedure described in step-1 of Example 1 from methyl 4-(chlorosulfonyl)benzoate and (1-cyclopropyl-1H-indazol-5-yl)methanamine (step-4 of Example 28).

$^1$H-NMR (300 MHz, CDCl$_3$) δ 8.13 (2H, d, J=9.5 Hz), 7.92 (2H, d, J=9.5 Hz), 7.85 (1H, s), 7.52-7.48 (2H, m), 7.26-7.19 (1H, m), 4.75-4.74 (1H, m), 4.28 (2H, d, J=6.6 Hz), 3.97 (3H, s), 3.60-3.50 (1H, m), 1.20-1.10 (4H, m).

LC-MS (method-A) m/z: M+1 obs 386.03, M−1 obs 384.05; tR=2.87 min.

Step-6: Methyl 4-(N-(3-chloro-5-(trifluoromethyl)pyridin-2-yl)-N-((1-cyclopropyl-1H-indazol-5-yl)methyl)sulfamoyl)benzoate The titled compound was prepared according to the procedure described in step-2 of Example 1 from 2,3-dichloro-5-(trifluoromethyl)pyridine and methyl 4-(N-((1-cyclopropyl-1H-indazol-5-yl)methyl)sulfamoyl)benzoate (step-5 of Example 28).

LC-MS (method-A) m/z: M+1 obs 565.00; tR=3.57 min.

Step-7: Methyl 4-(N-(3-chloro-5-(trifluoromethyl)pyridin-2-yl)-N-((1-cyclopropyl-1H-indazol-5-yl)methyl)sulfamoyl)benzoate The titled compound was prepared according to the procedure described in step-3 of Example 3 from methyl 4-(N-(3-chloro-5-(trifluoromethyl)pyridin-2-yl)-N-((1-cyclopropyl-1H-indazol-5-yl)$_m$ ethyl)sulfamoyl)benzoate (step-6 of Example 28).

LC-MS (method-A) m/z: M+1 obs 550.99, M−1 obs 549.01; tR=3.14 min.

The further purification was carried out by preparative LC-MS system in usual manner. HPLC-QC method, retention time and observed MS were summarized in Table 1.

Example 29

4-(N-((1-Cyclopropyl-1H-indazol-5-yl)methyl)-N-(3,5-dichloropyridin-2-yl)sulfamoyl)benzoic acid Step-1: Methyl 4-(N-((1-cyclopropyl-1H-indazol-5-yl)methyl)-N-(3,5-dichloropyridin-2-yl)sulfamoyl)benzoate The titled compound was prepared according to the procedure described in step-2 of Example 1 from 3,5-dichloro-2-fluoropyridine and methyl 4-(N-((1-cyclopropyl-1H-indazol-5-yl)methyl)sulfamoyl)benzoate (step-5 of Example 28).

LC-MS (method-A) m/z: M+1 obs 530.93; tR=3.40 min.

Step-2: 4-(N-((1-Cyclopropyl-1H-indazol-5-yl)methyl)-N-(3,5-dichloropyridin-2-yl)sulfamoyl)benzoic acid The titled compound was prepared according to the procedure described in step-3 of Example 3 from methyl 4-(N-((1-cyclopropyl-1H-indazol-5-yl)methyl)-N-(3,5-dichloropyridin-2-yl)sulfamoyl)benzoate (step-1 of Example 29).

LC-MS (method-A) m/z: M+1 obs 516.96, M−1 obs 514.99; tR=2.98 min.

The further purification was carried out by preparative LC-MS system in usual manner. HPLC-QC method, retention time and observed MS were summarized in Table 1.

Example 30

4-(N-(3-Chloro-5-(trifluoromethyl)pyridin-2-yl)-N-((1-methyl-1H-benzo[d][1,2,3]triazol-5-yl)methyl)sulfamoyl)benzoic acid Step-1: Methyl 4-(N-((1-methyl-1H-benzo[d][1,2,3]triazol-5-yl)methyl)sulfamoyl)benzoate The titled compound was prepared according to the procedure described in step-1 of Example 1 from methyl 4-(chlorosulfonyl)benzoate and (1-methyl-1H-benzo[d][1,2,3]triazol-5-yl)methanamine.

LC-MS (method-A) m/z: M+1 obs 361.11, M−1 obs 359.10; tR=2.55 min.

Step-2: Methyl 4-(N-(3-chloro-5-(trifluoromethyl)pyridin-2-yl)-N-((1-methyl-1H-benzo[d][1,2,3]triazol-5-yl)methyl)sulfamoyl)benzoate The titled compound was prepared according to the procedure described in step-2 of Example 1 from 2,3-dichloro-5-(trifluoromethyl)pyridine and methyl 4-(N-((1-methyl-1H-benzo[d][1,2,3]triazol-5-yl)methyl)sulfamoyl)benzoate (step-1 of Example 30).

LC-MS (method-A) m/z: M+1 obs 540.11; tR=3.18 min.

Step-3: 4-(N-(3-Chloro-5-(trifluoromethyl)pyridin-2-yl)-N-((1-methyl-1H-benzo[d][1,2,3]-triazol-5-yl)methyl)sulfamoyl)benzoic acid The titled compound was prepared according to the procedure described in step-3 of Example 3 from methyl 4-(N-(3-chloro-5-(trifluoromethyl)pyridin-2-yl)-N-((1-methyl-1H-benzo[d][1,2,3]triazol-5-yl)methyl)sulfamoyl)benzoate (step-2 of Example 30).

LC-MS (method-A) m/z: M+1 obs 526.08, M−1 obs 524.11; tR=2.80 min.

The further purification was carried out by preparative LC-MS system in usual manner. HPLC-QC method, retention time and observed MS were summarized in Table 1.

Example 31

3-Chloro-4-(N-(3-chloro-5-(trifluoromethyl)pyridin-2-yl)-N-((1-cyclopropyl-1H-indazol-5-yl)methyl)sulfamoyl)benzoic acid Step-1: Ethyl 3-chloro-4-(N-((1-cyclopropyl-1H-indazol-5-yl)methyl)sulfamoyl)benzoate The titled compound was prepared according to the procedure described in step-1 of Example 1 from ethyl 3-chloro-4-(chlorosulfonyl)benzoate and (1-cyclopropyl-1H-indazol-5-yl)methanamine (step-4 of Example 28).

LC-MS (method-A) m/z: M+1 obs 434.08, M−1 obs 432.11; tR=3.07 min.

Step-2: Ethyl 3-chloro-4-(N-(3-chloro-5-(trifluoromethyl)pyridin-2-yl)-N-((1-cyclopropyl-1H-indazol-5-yl)methyl)sulfamoyl)benzoate The titled compound was prepared according to the procedure described in step-2 of Example 1 from 2,3-dichloro-5-(trifluoromethyl)pyridine and ethyl 3-chloro-4-(N-((1-cyclopropyl-1H-indazol-5-yl)methyl)sulfamoyl)benzoate (step-1 of Example 31).

LC-MS (method-A) m/z: M+1 obs 613.14; tR=3.65 min.

Step-3: 3-Chloro-4-(N-(3-chloro-5-(trifluoromethyl)pyridin-2-yl)-N-((1-cyclopropyl-1H-indazol-5-yl)methyl)sulfamoyl)benzoic acid The titled compound was prepared according to the procedure described in step-3 of Example 3 from ethyl 3-chloro-4-(N-(3-chloro-5-(trifluoromethyl)pyridin-2-yl)-N-((1-cyclopropyl-1H-indazol-5-yl)methyl)sulfamoyl)benzoate (step-2 of Example 31).

LC-MS (method-A) m/z: M+1 obs 585.14, M−1 obs 583.16; tR=2.98 min.

The further purification was carried out by preparative LC-MS system in usual manner. HPLC-QC method, retention time and observed MS were summarized in Table 1.

Example 32

3-Chloro-4-(N-((1-cyclopropyl-1H-indazol-5-yl)methyl)-N-(3,5-dichloropyridin-2-yl)sulfamoyl)benzoic acid Step-1: Ethyl 3-chloro-4-(N-((1-cyclopropyl-1H-indazol-5-yl)methyl)-N-(3,5-dichloropyridin-2-yl)sulfamoyl)benzoate The titled compound was prepared according to the procedure described in step-2 of Example 1 from 3,5-dichloro-2-fluoropyridine and ethyl 3-chloro-4-(N-((1-cyclopropyl-1H-indazol-5-yl)methyl)sulfamoyl)benzoate (step-1 of Example 31).

LC-MS (method-A) m/z: M+1 obs 581.12; tR=3.62 min.

Step-2: 3-Chloro-4-(N-((1-cyclopropyl-1H-indazol-5-yl)methyl)-N-(3,5-dichloropyridin-2-yl)sulfamoyl)benzoic acid The titled compound was prepared according to the procedure described in step-3 of Example 3 from ethyl 3-chloro-4-(N-((1-cyclopropyl-1H-indazol-5-yl)methyl)-N-(3,5-dichloropyridin-2-yl)sulfamoyl)benzoate (step-1 of Example 32).

LC-MS (method-A) m/z: M+1 obs 553.12, M−1 obs 551.13; tR=2.93 min.

The further purification was carried out by preparative LC-MS system in usual manner. HPLC-QC method, retention time and observed MS were summarized in Table 1.

Example 33

4-(N-(3-Chloro-5-(trifluoromethyl)pyridin-2-yl)-N-((1-cyclopropyl-1H-indazol-5-yl)methyl)sulfamoyl)-3-methylbenzoic acid

Step-1: 4-Bromo-N-((1-cyclopropyl-1H-indazol-5-yl)methyl)-2-methylbenzenesulfonamide The titled compound was prepared according to the procedure described in step-1 of Example 1 from 4-bromo-2-methylbenzene-1-sulfonyl chloride and (1-cyclopropyl-1H-indazol-5-yl)methanamine (step-4 of Example 28).

LC-MS (method-A) m/z: M+1 obs 422.12, M−1 obs 420.09; tR=3.22 min.

Step-2: Methyl 4-(N-((1-cyclopropyl-1H-indazol-5-yl)methyl)sulfamoyl)-3-methylbenzoate The titled compound was prepared according to the procedure described in step-2 of Example 4 from 4-bromo-N-((1-cyclopropyl-1H-indazol-5-yl)methyl)-2-methylbenzenesulfonamide (step-1 of Example 33).

LC-MS (method-A) m/z: M+1 obs 400.18, M−1 obs 398.20; tR=2.93 min.

Step-3: Methyl 4-(N-(3-chloro-5-(trifluoromethyl)pyridin-2-yl)-N-((1-cyclopropyl-1H-indazol-5-yl)methyl)sulfamoyl)-3-methylbenzoate The titled compound was prepared according to the procedure described in step-2 of Example 1 from 2,3-dichloro-5-(trifluoromethyl)pyridine and methyl 4-(N-((1-cyclopropyl-1H-indazol-5-yl)methyl)sulfamoyl)-3-methylbenzoate (step-2 of Example 33).

LC-MS (method-A) m/z: M+1 obs 579.21; tR=3.52 min.

Step-4: 4-(N-(3-Chloro-5-(trifluoromethyl)pyridin-2-yl)-N-((1-cyclopropyl-1H-indazol-5-yl)methyl)sulfamoyl)-3-methylbenzoic acid The titled compound was prepared according to the procedure described in step-3 of Example 3 from methyl 4-(N-(3-chloro-5-(trifluoromethyl)pyridin-2-yl)-N-((1-cyclopropyl-1H-indazol-5-yl)methyl)sulfamoyl)-3-methylbenzoate (step-3 of Example 33).

LC-MS (method-A) m/z: M+1 obs 565.24, M−1 obs 563.26; tR=3.09 min.

The further purification was carried out by preparative LC-MS system in usual manner. HPLC-QC method, retention time and observed MS were summarized in Table 1.

Example 34

4-(N-((1-Cyclopropyl-1H-indazol-5-yl)methyl)-N-(3,5-dichloropyridin-2-yl)sulfamoyl)-3-methylbenzoic acid

Step-1: Methyl 4-(N-((1-cyclopropyl-1H-indazol-5-yl)methyl)-N-(3,5-dichloropyridin-2-yl)sulfamoyl)-3-methylbenzoate The titled compound was prepared according to the procedure described in step-2 of Example 1 from 3,5-dichloro-2-fluoropyridine and methyl 4-(N-((1-cyclopropyl-1H-indazol-5-yl)methyl)sulfamoyl)-3-methylbenzoate (step-2 of Example 33).

LC-MS (method-A) m/z: M+1 obs 545.21; tR=3.48 min.

Step-2: 4-(N-((1-Cyclopropyl-1H-indazol-5-yl)methyl)-N-(3,5-dichloropyridin-2-yl)sulfamoyl)-3-methylbenzoic acid The titled compound was prepared according to the procedure described in step-3 of Example 3 from methyl 4-(N-((1-cyclopropyl-1H-indazol-5-yl)methyl)-N-(3,5-dichloropyridin-2-yl)sulfamoyl)-3-methylbenzoate (step-1 of Example 34).

LC-MS (method-A) m/z: M+1 obs 531.18, M−1 obs 529.20; tR=3.02 min.

The further purification was carried out by preparative LC-MS system in usual manner. HPLC-QC method, retention time and observed MS were summarized in Table 1.

Example 35

3-Chloro-4-(N-(3-chloro-5-(trifluoromethyl)pyridin-2-yl)-N-((1-methyl-1H-pyrrolo[2,3-b]pyridin-5-yl)methyl)sulfamoyl)benzoic acid

Step-1: (1-Methyl-1H-pyrrolo[2,3-b]pyridin-5-yl)methanamine

To a stirred solution of 1-methyl-1H-pyrrolo[2,3-b]pyridine-5-carbonitrile (210 mg, 1.3 mmol) in 10% NH$_3$-MeOH (10 mL) was added Raney Nickel (0.5 mL, Raney (registered trademark) 2800 slurry in water), and the mixture was stirred at room temperature under hydrogen atmosphere for 4 hrs. The mixture was filtered through a pad of Celite (registered trademark), washed with MeOH, the filtrate was concentrated to give 200 mg (93% yield) of the titled compound as a white solid.

LC-MS (method-A) m/z: M+1 obs 162.28; tR=0.57 min.

Step-2: Ethyl 3-chloro-4-(N-((1-methyl-1H-pyrrolo[2,3-b]pyridin-5-yl)methyl)sulfamoyl)benzoate The titled compound was prepared according to the procedure described in step-1 of Example 1 from ethyl 3-chloro-4-(chlorosulfonyl)benzoate and (1-methyl-1H-pyrrolo[2,3-b]pyridin-5-yl)methanamine (step-1 of Example 35).

LC-MS (method-A) m/z: M+1 obs 408.18, M−1 obs 406.17; tR=2.85 min.

Step-3: Ethyl 3-chloro-4-(N-(3-chloro-5-(trifluoromethyl)pyridin-2-yl)-N-((1-methyl-1H-pyrrolo[2,3-b]pyridin-5-yl)methyl)sulfamoyl)benzoate The titled compound was prepared according to the procedure described in step-2 of Example 1 from 2,3-dichloro-5-(trifluoromethyl)pyridine and ethyl 3-chloro-4-(N-((1-methyl-1H-pyrrolo[2,3-b]pyridin-5-yl)methyl)sulfamoyl)benzoate (step-2 of Example 35).
LC-MS (method-A) m/z: M+1 obs 587.24; tR=3.52 min.

Step-4: 3-Chloro-4-(N-(3-chloro-5-(trifluoromethyl)pyridin-2-yl)-N-((1-methyl-1H-pyrrolo[2, 3-b]pyridin-5-yl)methyl)sulfamoyl)benzoic acid The titled compound was prepared according to the procedure described in step-3 of Example 3 from ethyl 3-chloro-4-(N-(3-chloro-5-(trifluoromethyl)pyridin-2-yl)-N-((1-methyl-1H-pyrrolo[2,3-b]pyridin-5-yl)methyl)sulfamoyl)benzoate (step-3 of Example 35).
LC-MS (method-A) m/z: M+1 obs 559.18, M−1 obs 557.21; tR=3.00 min.
The further purification was carried out by preparative LC-MS system in usual manner. HPLC-QC method, retention time and observed MS were summarized in Table 1.

Example 36

3-Chloro-4-(N-(3,5-dichloropyridin-2-yl)-N-((1-methyl-1H-pyrrolo[2,3-b]pyridin-5-yl)methyl)sulfamoyl)benzoic acid

Step-1: Ethyl 3-chloro-4-(N-(3,5-dichloropyridin-2-yl)-N-((1-methyl-1H-pyrrolo[2,3-b]pyridin-5-yl)methyl)sulfamoyl)benzoate The titled compound was prepared according to the procedure described in step-2 of Example 1 from 3,5-dichloro-2-fluoropyridine and ethyl 3-chloro-4-(N-((1-methyl-1H-pyrrolo[2,3-b]pyridin-5-yl)methyl)sulfamoyl)benzoate (step-2 of Example 35).
LC-MS (method-A) m/z: M+1 obs 555.16; tR=3.48 min.

Step-2: 3-Chloro-4-(N-(3,5-dichloropyridin-2-yl)-N-((1-methyl-1H-pyrrolo[2,3-b]pyridin-5-yl)methyl)sulfamoyl)benzoic acid The titled compound was prepared according to the procedure described in step-3 of Example 3 from ethyl 3-chloro-4-(N-(3,5-dichloropyridin-2-yl)-N-((1-methyl-1H-pyrrolo[2,3-b]pyridin-5-yl)methyl)sulfamoyl)benzoate (step-1 of Example 36).
LC-MS (method-A) m/z: M+1 obs 527.14, M−1 obs 525.16; tR=2.90 min.
The further purification was carried out by preparative LC-MS system in usual manner. HPLC-QC method, retention time and observed MS were summarized in Table 1.

Example 37

4-(N-(3-Chloro-5-(trifluoromethyl)pyridin-2-yl)-N-((1-methyl-1H-pyrrolo[2,3-b]pyridin-5-yl)methyl)sulfamoyl)benzoic acid

Step-1: Methyl 4-(N-((1-methyl-1H-pyrrolo[2,3-b]pyridin-5-yl)methyl)sulfamoyl)benzoate The titled compound was prepared according to the procedure described in step-1 of Example 1 from methyl 4-(chlorosulfonyl)benzoate and (1-methyl-1H-pyrrolo[2,3-b]pyridin-5-yl)methanamine (step-1 of Example 35).
LC-MS (method-A) m/z: M+1 obs 360.22, M−1 obs 358.22; tR=2.68 min.

Step-2: Methyl 4-(N-(3-chloro-5-(trifluoromethyl)pyridin-2-yl)-N-((1-methyl-1H-pyrrolo[2,3-b]pyridin-5-yl)methyl)sulfamoyl)benzoate The titled compound was prepared according to the procedure described in step-2 of Example 1 from 2,3-dichloro-5-(trifluoromethyl)pyridine and methyl 4-(N-((1-methyl-1H-pyrrolo[2,3-b]pyridin-5-yl)methyl)sulfamoyl)benzoate (step-1 of Example 37).
LC-MS (method-A) m/z: M+1 obs 539.22; tR=3.34 min.

Step-3: 4-(N-(3-Chloro-5-(trifluoromethyl)pyridin-2-yl)-N-((1-methyl-1H-pyrrolo[2,3-b]pyridin-5-yl)methyl)sulfamoyl)benzoic acid The titled compound was prepared according to the procedure described in step-3 of Example 3 from ethyl 4-(N-(3-chloro-5-(trifluoromethyl)pyridin-2-yl)-N-((1-methyl-1H-pyrrolo[2,3-b]pyridin-5-yl)methyl)sulfamoyl)benzoate (step-2 of Example 37).
LC-MS (method-A) m/z: M+1 obs 525.13, M−1 obs 523.15; tR=2.92 min.
The further purification was carried out by preparative LC-MS system in usual manner. HPLC-QC method, retention time and observed MS were summarized in Table 1.

Example 38

4-(N-(3-Chloro-5-(trifluoromethyl)pyridin-2-yl)-N-(quinolin-3-ylmethyl)sulfamoyl)benzoic acid

Step-1: Methyl 4-(N-(quinolin-3-ylmethyl)sulfamoyl)benzoate

The titled compound was prepared according to the procedure described in step-1 of Example 1 from methyl 4-(chlorosulfonyl)benzoate and quinolin-3-ylmethanamine.
$^1$H-NMR (270 MHz, DMSOd$_6$) δ 9.06 (1H, s), 8.78 (1H, t, J=6.0 Hz), 8.67 (1H, s), 8.21 (1H, d, J=8.6 Hz), 8.14 (1H, d, J=8.6 Hz), 7.99 (2H, t, J=8.6 Hz), 7.91 (2H, d, J=8.6 Hz), 7.81 (1H, t, J=2.7 Hz), 4.39 (2H, d, J=6.6 Hz), 3.87 (3H, s). Signal due to NH was not observed.
LC-MS (method-A) m/z: M+1 obs 357.05; tR=2.71 min.

Step-2: Methyl 4-(N-(3-chloro-5-(trifluoromethyl)pyridin-2-yl)-N-(quinolin-3-ylmethyl)sulfamoyl)benzoate The titled compound was prepared according to the procedure described in step-2 of Example 1 from 2,3-dichloro-5-(trifluoromethyl)pyridine and methyl 4-(N-(quinolin-3-ylmethyl)sulfamoyl)benzoate (step-1 of Example 38).
LC-MS (method-A) m/z: M+1 obs 535.95; tR=3.35 min.

Step-3: 4-(N-(3-Chloro-5-(trifluoromethyl)pyridin-2-yl)-N-(quinolin-3-ylmethyl)sulfamoyl)benzoic acid The titled compound was prepared according to the procedure described in step-3 of Example 3 from methyl 4-(N-(3-chloro-5-(trifluoromethyl)pyridin-2-yl)-N-(quinolin-3-ylmethyl)sulfamoyl)benzoate (step-2 of Example 38).
LC-MS (method-A) m/z: M+1 obs 521.93; tR=2.95 min.

The further purification was carried out by preparative LC-MS system in usual manner. HPLC-QC method, retention time and observed MS were summarized in Table 1.

Example 39

4-(N-(3-Chloro-5-(trifluoromethyl)pyridin-2-yl)-N-(quinolin-6-ylmethyl)sulfamoyl)benzoic acid

Step-1: Methyl 4-(N-(quinolin-6-ylmethyl)sulfamoyl)benzoate

The titled compound was prepared according to the procedure described in step-1 of Example 1 from methyl 4-(chlorosulfonyl)benzoate and quinolin-6-ylmethanamine.

LC-MS (method-A) m/z: M+1 obs 357.05; tR=2.61 min.

Step-2: Methyl 4-(N-(3-chloro-5-(trifluoromethyl)pyridin-2-yl)-N-(quinolin-6-ylmethyl)sulfamoyl)benzoate The titled compound was prepared according to the procedure described in step-2 of Example 1 from 2,3-dichloro-5-(trifluoromethyl)pyridine and methyl 4-(N-(quinolin-6-ylmethyl)sulfamoyl)benzoate (step-1 of Example 39).

LC-MS (method-A) m/z: M+1 obs 535.95; tR=3.32 min.

Step-3: 4-(N-(3-chloro-5-(trifluoromethyl)pyridin-2-yl)-N-(quinolin-6-ylmethyl)sulfamoyl)benzoic acid The titled compound was prepared according to the procedure described in step-3 of Example 3 from methyl 4-(N-(3-chloro-5-(trifluoromethyl)pyridin-2-yl)-N-(quinolin-6-ylmethyl)sulfamoyl)benzoate (step-2 of Example 39).

LC-MS (method-A) m/z: M+1 obs 521.93; tR=2.88 min.

The further purification was carried out by preparative LC-MS system in usual manner. HPLC-QC method, retention time and observed MS were summarized in Table 1.

All examples were identified as the described compounds with the chemical purity of greater than 90% by preparative LC-MS and HPLC-QC method. In Table 1, HPLC retention time and observed MS were measured by HPLC-QC method.

Conditions for Determining HPLC-OC Retention Time for Example Compounds:

Apparatus: Waters Acquity Ultra Performance LC on TUV Detector and ZQ mass spectrometer Column: Waters ACQUITY C18, 2.1×100 mm, 1.7 micrometer particle Column Temperature: 60° C.

Solvents:
A1: 10 mM ammonium acetate aqueous solution
B1: Acetonitrile

| Time(min) | A1(%) | B1(%) |
|---|---|---|
| 0 | 95 | 5 |
| 0.1 | 95 | 5 |
| 1.8 | 5 | 95 |
| 2.3 | 95 | 5 | run time 3.0 min
flow 0.7 mL/min

TABLE 1

| Example | Name | Structure | HPLC Retention Time | MS (ESI): m/z (M − H)+ |
|---|---|---|---|---|
| Example 1 | 4-(N-(Benzofuran-5-ylmethyl)-N-(3-chloro-5-(trifluoromethyl)pyridin-2-yl)sulfamoyl)benzoic acid | 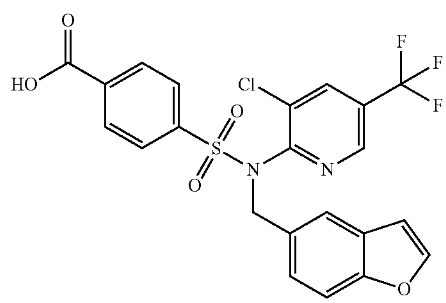 [SMILES: O=C(O)c1ccc(S(=O)(=O)N(Cc2ccc3occc3c2)c2ncc(C(F)(F)F)cc2Cl)cc1] | 1.47 min | 508.8 |
| Example 2 | 4-(N-(Benzofuran-6-ylmethyl)-N-(3-chloro-5-(trifluoromethyl)pyridin-2-yl)sulfamoyl)benzoic acid | 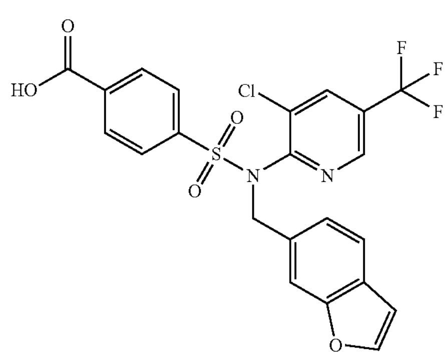 [SMILES: O=C(O)c1ccc(S(=O)(=O)N(Cc2ccc3ccoc3c2)c2ncc(C(F)(F)F)cc2Cl)cc1] | 1.46 min | 508.9 |

TABLE 1-continued

| Example | Name | Structure | HPLC Retention Time | MS (ESI): m/z (M − H)+ |
|---|---|---|---|---|
| Example 3 | 4-(N-(3-Chloro-5-(tri-fluoromethyl)pyridin-2-yl)-N-((1-methyl-1H-indazol-5-yl)methyl)sulfamoyl)benzoic acid | 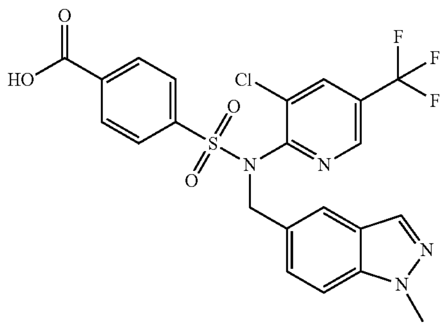 [SMILES: Cn1ncc2cc(CN(c3ncc(C(F)(F)F)cc3Cl)S(=O)(=O)c3ccc(C(=O)O)cc3)ccc21] | 1.32 min | 522.9 |
| Example 4 | 4-(N-(3-Chloro-5-(tri-fluoromethyl)pyridin-2-yl)-N-((1-methyl-1H-indazol-5-yl)methyl)sulfamoyl)-3-ethyl-benzoic acid | 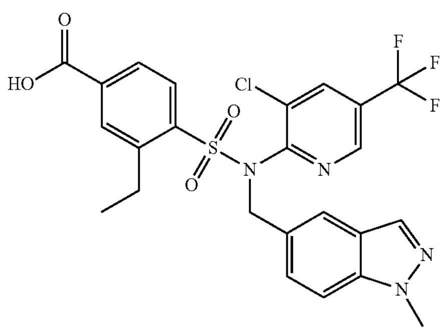 [SMILES: CCc1cc(C(=O)O)ccc1S(=O)(=O)N(Cc1ccc2c(cnn2C)c1)c1ncc(C(F)(F)F)cc1Cl] | 1.38 min | 551.3 |
| Example 5 | 4-(N-(Benzofuran-5-ylmethyl)-N-(3,5-di-chloropyridin-2-yl)sulfamoyl)benzoic acid | 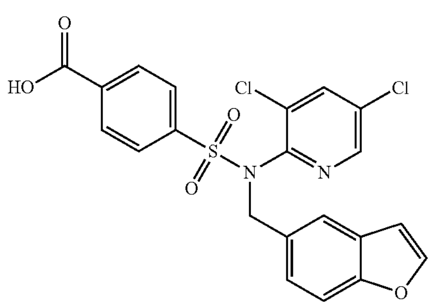 [SMILES: O=C(O)c1ccc(S(=O)(=O)N(Cc2ccc3occc3c2)c2ncc(Cl)cc2Cl)cc1] | 1.43 min | 475.0 |
| Example 6 | 4-(N-(3-Chloro-5-(tri-fluoromethyl)pyridin-2-yl)-N-((1-methyl-1H-indol-5-yl)methyl)sulfamoyl)benzoic acid | 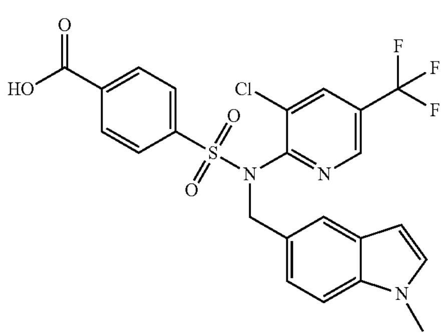 [SMILES: Cn1ccc2cc(CN(c3ncc(C(F)(F)F)cc3Cl)S(=O)(=O)c3ccc(C(=O)O)cc3)ccc21] | 1.46 min | 521.9 |

TABLE 1-continued

| Example | Name | Structure | HPLC Retention Time | MS (ESI): m/z (M − H)+ |
|---|---|---|---|---|
| Example 7 | 4-(N-(3,5-Dichloro-pyridin-2-yl)-N-((1-methyl-1H-indol-5-yl)methyl)sulfamoyl)benzoic acid | 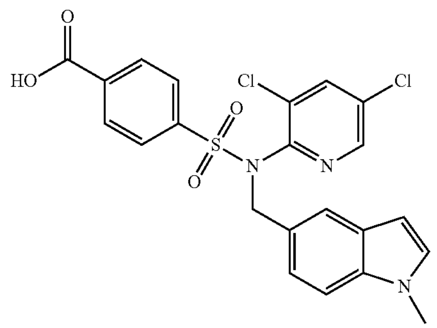 [SMILES: Cn1ccc2cc(CN(c3ncc(Cl)cc3Cl)S(=O)(=O)c3ccc(C(=O)O)cc3)ccc21] | 1.28 min | 489.0 |
| Example 8 | 3-Chloro-4-(N-(3-chloro-5-(trifluoromethyl)pyridin-2-yl)-N-((1-methyl-1H-indol-5-yl)methyl)sulfamoyl)benzoic acid | 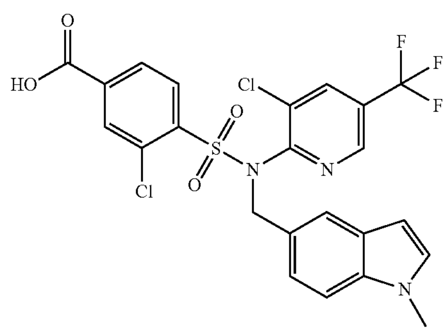 | 1.48 min | 555.9 |
| Example 9 | 3-Chloro-4-(N-(3,5-dichloropyridin-2-yl)-N-((1-methyl-1H-indol-5-yl)methyl)sulfamoyl)benzoic acid | 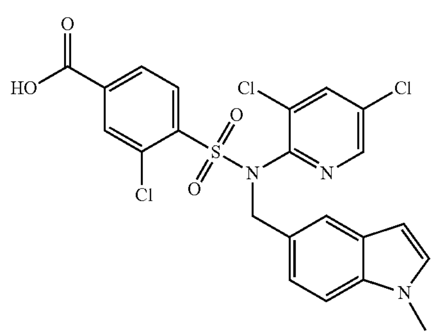 | 1.45 min | 522.0 |
| Example 10 | 4-(N-(Benzofuran-6-ylmethyl)-N-(3,5-dichloropyridin-2-yl)sulfamoyl)benzoic acid | 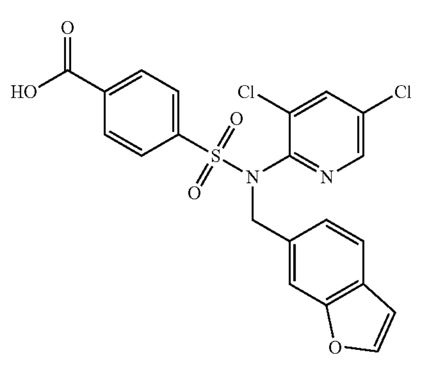 [SMILES: O=C(O)c1ccc(S(=O)(=O)N(Cc2ccc3ccoc3c2)c2ncc(Cl)cc2Cl)cc1] | 1.42 min | 475.0 |

TABLE 1-continued

| Example | Name | Structure | HPLC Retention Time | MS (ESI): m/z (M − H)+ |
| --- | --- | --- | --- | --- |
| Example 11 | 4-(N-(3-Chloro-5-(tri-fluoromethyl)pyridin-2-yl)-N-((1-methyl-1H-indol-5-yl)methyl)sulfamoyl)-3-methylbenzoic acid | 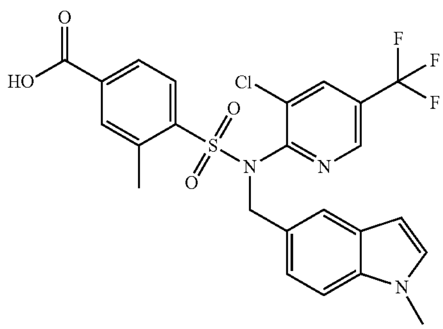 [SMILES: Cc1cc(C(=O)O)ccc1S(=O)(=O)N(Cc1ccc2c(ccn2C)c1)c1ncc(C(F)(F)F)cc1Cl] | 1.48 min | 535.9 |
| Example 12 | 4-(N-(3,5-Dichloro-pyridin-2-yl)-N-((1-methyl-1H-indol-5-yl)methyl)sulfamoyl)-3-methylbenzoic acid | 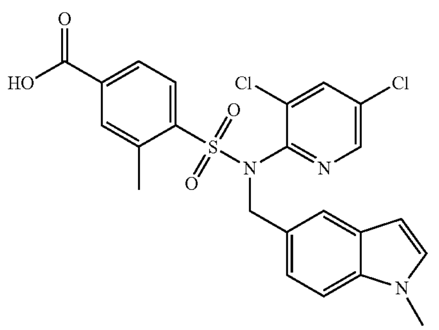 [SMILES: Cc1cc(C(=O)O)ccc1S(=O)(=O)N(Cc1ccc2c(ccn2C)c1)c1ncc(Cl)cc1Cl] | 1.43 min | 502.0 |
| Example 13 | 4-(N-(3-Chloro-5-(tri-fluoromethyl)pyridin-2-yl)-N-((2-ethyl-2H-indazol-5-yl)methyl)sulfamoyl)benzoic acid | 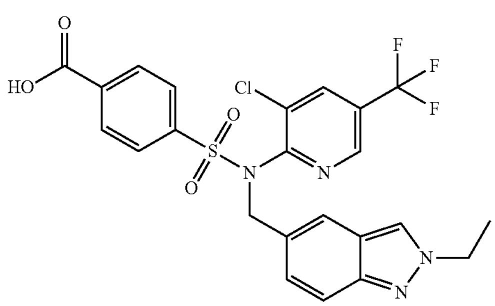 [SMILES: CCn1cc2cc(CN(c3ncc(C(F)(F)F)cc3Cl)S(=O)(=O)c3ccc(C(=O)O)cc3)ccc2n1] | 1.33 min | 537.1 |
| Example 14 | 3-Chloro-4-(N-(3-chloro-5-(trifluoromethyl)pyridin-2-yl)-N-((1-ethyl-1H-indazol-5-yl)methyl)sulfamoyl)benzoic acid | 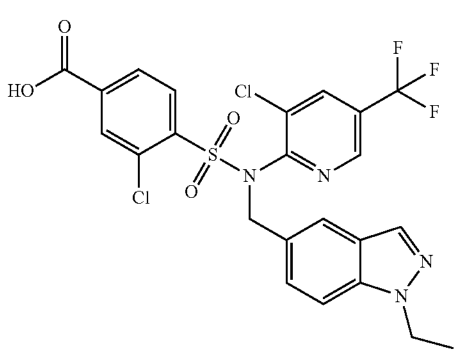 [SMILES: CCn1ncc2cc(CN(c3ncc(C(F)(F)F)cc3Cl)S(=O)(=O)c3ccc(C(=O)O)cc3Cl)ccc21] | 1.44 min | 571.1 |

TABLE 1-continued

| Example | Name | Structure | HPLC Retention Time | MS (ESI): m/z (M − H)+ |
|---|---|---|---|---|
| Example 15 | 4-(N-(3-Chloro-5-(trifluoromethyl)pyridin-2-yl)-N-((1-ethyl-1H-indazol-5-yl)methyl)sulfamoyl)benzoic acid | 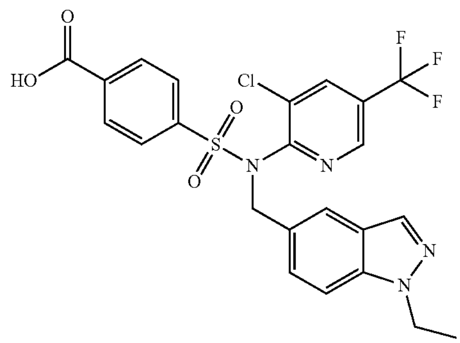 [SMILES: CCn1ncc2cc(CN(c3ncc(C(F)(F)F)cc3Cl)S(=O)(=O)c3ccc(C(=O)O)cc3)ccc21] | 1.40 min | 537.1 |
| Example 16 | 4-(N-(3-Chloro-5-(trifluoromethyl)pyridin-2-yl)-N-((2-methyl-2H-indazol-5-yl)methyl)sulfamoyl)benzoic acid | 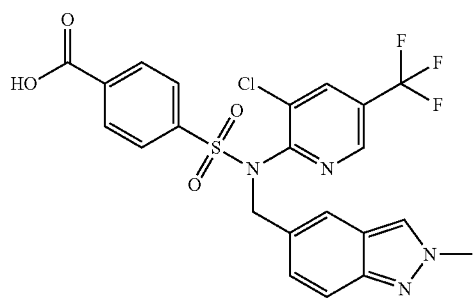 [SMILES: Cn1cc2cc(CN(c3ncc(C(F)(F)F)cc3Cl)S(=O)(=O)c3ccc(C(=O)O)cc3)ccc2n1] | 1.27 min | |
| Example 17 | 4-(N-(3-Chloro-5-(trifluoromethyl)pyridin-2-yl)-N-((1-methyl-1H-indazol-6-yl)methyl)sulfamoyl)benzoic acid | 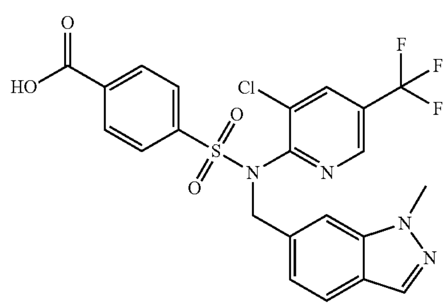 [SMILES: Cn1ncc2ccc(CN(c3ncc(C(F)(F)F)cc3Cl)S(=O)(=O)c3ccc(C(=O)O)cc3)cc21] | 1.34 min | 523.1 |
| Example 18 | 4-(N-(3-Chloro-5-(trifluoromethyl)pyridin-2-yl)-N-((2-methyl-2H-indazol-6-yl)methyl)sulfamoyl)benzoic acid | 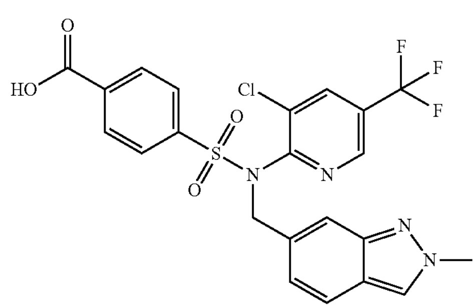 [SMILES: Cn1cc2ccc(CN(c3ncc(C(F)(F)F)cc3Cl)S(=O)(=O)c3ccc(C(=O)O)cc3)cc2n1] | 1.28 min | 523.1 |

TABLE 1-continued

| Example | Name | Structure | HPLC Retention Time | MS (ESI): m/z (M − H)+ |
|---------|------|-----------|---------------------|------------------------|
| Example 19 | 4-(N-(3,5-Dichloro-pyridin-2-yl)-N-((1-ethyl-1H-indazol-5-yl)methyl)sulfamoyl)benzoic acid | 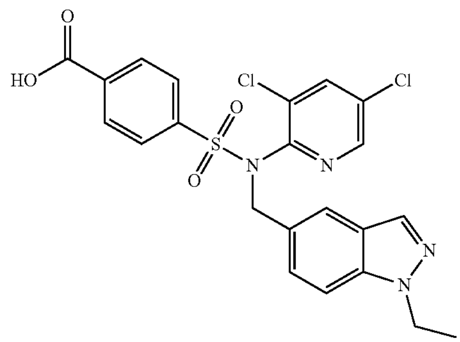 [SMILES: CCn1ncc2cc(CN(c3ncc(Cl)cc3Cl)S(=O)(=O)c3ccc(C(=O)O)cc3)ccc21] | 1.34 min | 503.2 |
| Example 20 | 4-(N-(3-Chloro-5-(trifluoromethyl)pyridin-2-yl)-N-((1-(2-methoxyethyl)-1H-indazol-5-yl)methyl)sulfamoyl)benzoic acid | 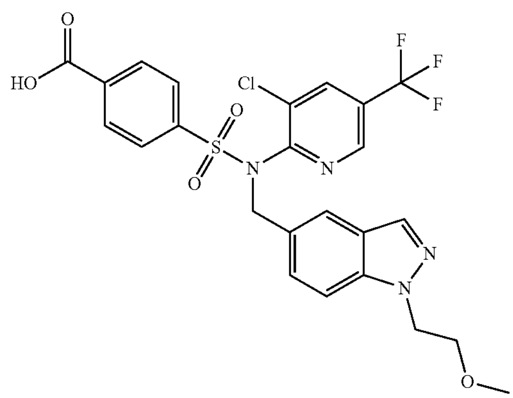 [SMILES: COCCn1ncc2cc(CN(c3ncc(C(F)(F)F)cc3Cl)S(=O)(=O)c3ccc(C(=O)O)cc3)ccc21] | 1.35 min | 567.2 |
| Example 21 | 4-(N-(3-Chloro-5-(trifluoromethyl)pyridin-2-yl)-N-((1-(tetrahydro-2H-pyran-4-yl)-1H-indazol-5-yl)methyl)sulfamoyl)benzoic acid | 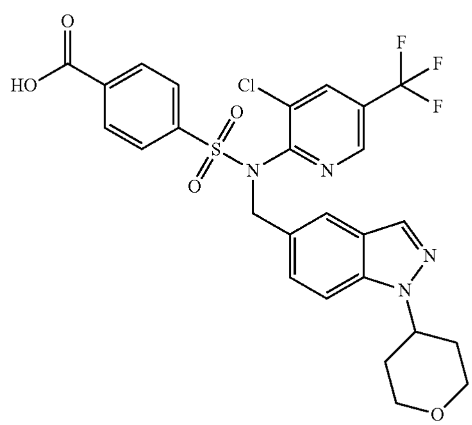 [SMILES: O=C(O)c1ccc(S(=O)(=O)N(Cc2ccc3c(cnn3C3CCOCC3)c2)c2ncc(C(F)(F)F)cc2Cl)cc1] | 1.37 min | 593.2 |
| Example 22 | 4-(N-(3-Chloro-5-(trifluoromethyl)pyridin-2-yl)-N-((1-(2-hydroxy-2-methylpropyl)-1H-indazol-5-yl)methyl)sulfamoyl)benzoic acid | 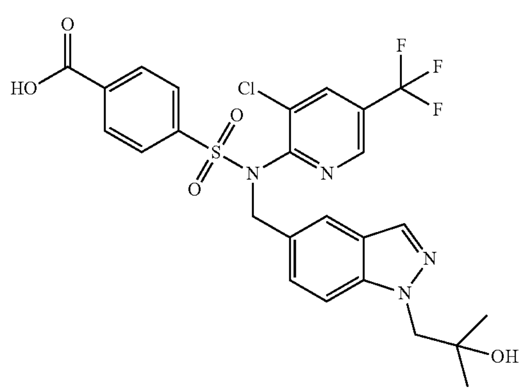 [SMILES: CC(C)(O)Cn1ncc2cc(CN(c3ncc(C(F)(F)F)cc3Cl)S(=O)(=O)c3ccc(C(=O)O)cc3)ccc21] | 1.32 min | 581.3 |

TABLE 1-continued

| Example | Name | Structure | HPLC Retention Time | MS (ESI): m/z (M − H)+ |
|---|---|---|---|---|
| Example 23 | 4-(N-(3,5-Dichloro-pyridin-2-yl)-N-((1-methyl-1H-indazol-5-yl)methyl)sulfamoyl)-3-ethylbenzoic acid | 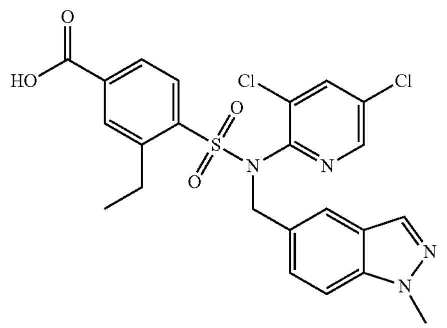 [SMILES: CCc1cc(C(=O)O)ccc1S(=O)(=O)N(Cc1ccc2c(cnn2C)c1)c1ncc(Cl)cc1Cl] | 1.33 min | 517.3 |
| Example 24 | 3-Chloro-4-(N-(3,5-dichloropyridin-2-yl)-N-((1-methyl-1H-indazol-5-yl)methyl)sulfamoyl)benzoic acid | 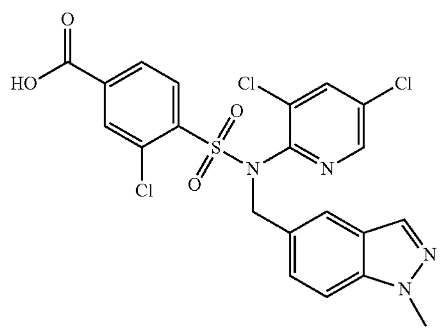 [SMILES: Cn1ncc2cc(CN(c3ncc(Cl)cc3Cl)S(=O)(=O)c3ccc(C(=O)O)cc3Cl)ccc21] | 1.32 min | 523.0 |
| Example 25 | 3-Chloro-4-(N-(3-chloro-5-(trifluoromethyl)pyridin-2-yl)-N-((1-methyl-1H-indazol-5-yl)methyl)sulfamoyl)benzoic acid | 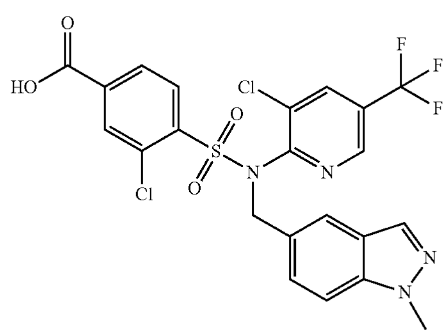 [SMILES: Cn1ncc2cc(CN(c3ncc(C(F)(F)F)cc3Cl)S(=O)(=O)c3ccc(C(=O)O)cc3Cl)ccc21] | 1.37 min | 557.0 |
| Example 26 | 4-(N-(3-Chloro-5-(trifluoromethyl)pyridin-2-yl)-N-((1-methyl-1H-indazol-5-yl)methyl)sulfamoyl)-3-methylbenzoic acid | 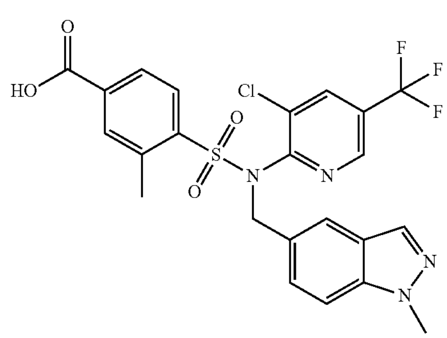 | 1.35 min | 537.1 |

TABLE 1-continued

| Example | Name | Structure | HPLC Retention Time | MS (ESI): m/z (M − H)+ |
| --- | --- | --- | --- | --- |
| Example 27 | 4-(N-(3,5-Dichloro-pyridin-2-yl)-N-((1-methyl-1H-indazol-5-yl)methyl)sulfamoyl)-3-methylbenzoic acid | 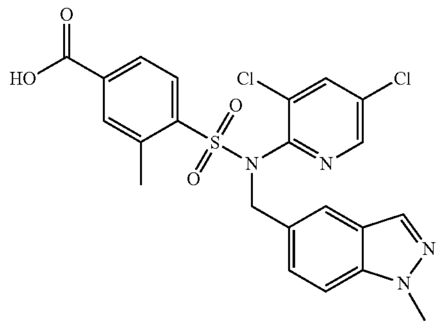 [SMILES: Cc1cc(C(=O)O)ccc1S(=O)(=O)N(Cc1ccc2c(cnn2C)c1)c1ncc(Cl)cc1Cl] | 1.29 min | 503.1 |
| Example 28 | 4-(N-(3-Chloro-5-(tri-fluoromethyl)pyridin-2-yl)-N-((1-cycloprop-yl-1H-indazol-5-yl)methyl)sulfamoyl)benzoic acid | 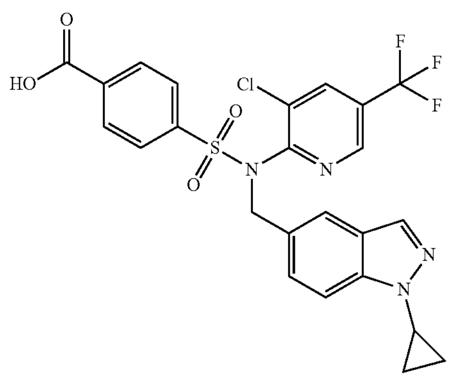 [SMILES: O=C(O)c1ccc(S(=O)(=O)N(Cc2ccc3c(cnn3C3CC3)c2)c2ncc(C(F)(F)F)cc2Cl)cc1] | 1.42 min | 549.2 |
| Example 29 | 4-(N-((1-Cyclopropyl-1H-indazol-5-yl)methyl)-N-(3,5-dichloro-pyridin-2-yl)sulfamoyl)benzoic acid | 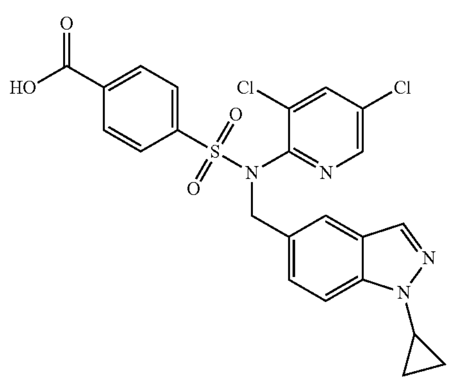 [SMILES: O=C(O)c1ccc(S(=O)(=O)N(Cc2ccc3c(cnn3C3CC3)c2)c2ncc(Cl)cc2Cl)cc1] | 1.37 min | 515.2 |
| Example 30 | 4-(N-(3-Chloro-5-(tri-fluoromethyl)pyridin-2-yl)-N-((1-methyl-1H-benzo[d][1,2,3]tri-azol-5-yl)methyl)sulfamoyl)benzoic acid | 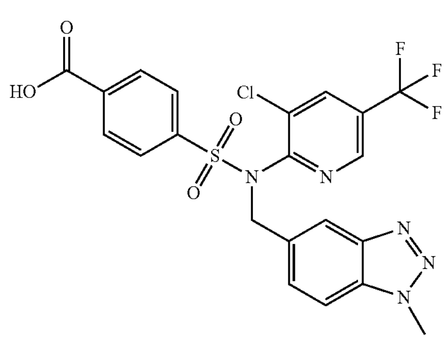 [SMILES: Cn1nnc2cc(CN(c3ncc(C(F)(F)F)cc3Cl)S(=O)(=O)c3ccc(C(=O)O)cc3)ccc21] | 1.28 min | 524.3 |

TABLE 1-continued

| Example | Name | Structure | HPLC Retention Time | MS (ESI): m/z (M − H)+ |
|---|---|---|---|---|
| Example 31 | 3-Chloro-4-(N-(3-chloro-5-(trifluoromethyl)pyridin-2-yl)-N-((1-cyclopropyl-1H-indazol-5-yl)methyl)sulfamoyl)benzoic acid | 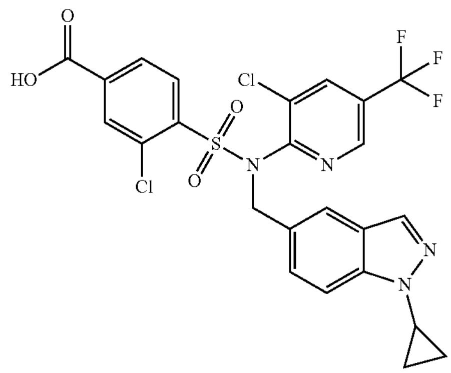 | 1.40 min | 583.3 |
| Example 32 | 3-Chloro-4-(N-((1-cyclopropyl-1H-indazol-5-yl)methyl)-N-(3,5-dichloropyridin-2-yl)sulfamoyl)benzoic acid | 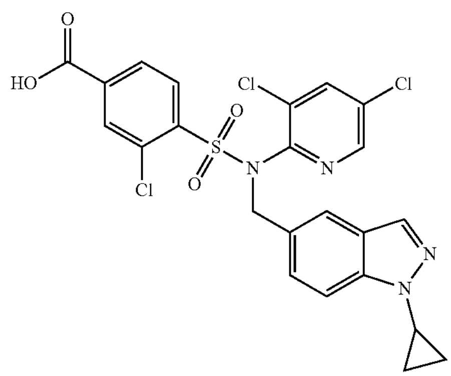 | 1.40 min | 549.2 |
| Example 33 | 4-(N-(3-Chloro-5-(trifluoromethyl)pyridin-2-yl)-N-((1-cyclopropyl-1H-indazol-5-yl)methyl)sulfamoyl)-3-methylbenzoic acid | 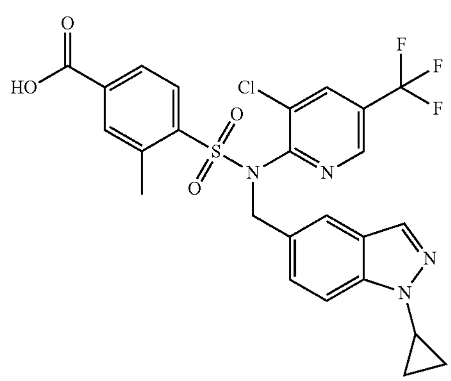 [SMILES: Cc1cc(C(=O)O)ccc1S(=O)(=O)N(Cc1ccc2c(cnn2C2CC2)c1)c1ncc(C(F)(F)F)cc1Cl] | 1.43 min | 563.3 |
| Example 34 | 4-(N-((1-Cyclopropyl-1H-indazol-5-yl)methyl)-N-(3,5-dichloropyridin-2-yl)sulfamoyl)-3-methylbenzoic acid | 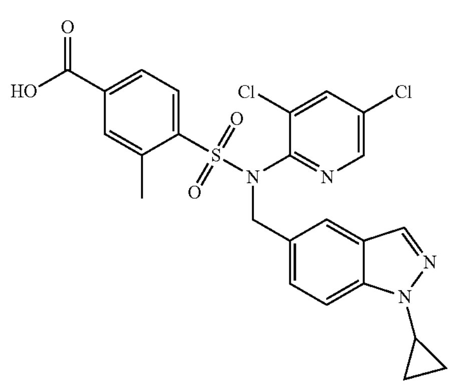 [SMILES: Cc1cc(C(=O)O)ccc1S(=O)(=O)N(Cc1ccc2c(cnn2C2CC2)c1)c1ncc(Cl)cc1Cl] | 1.38 min | 529.3 |

TABLE 1-continued

| Example | Name | Structure | HPLC Retention Time | MS (ESI): m/z (M − H)+ |
|---|---|---|---|---|
| Example 35 | 3-Chloro-4-(N-(3-chloro-5-(trifluoromethyl)pyridin-2-yl)-N-((1-methyl-1H-pyrrolo[2,3-b]pyridin-5-yl)methyl)sulfamoyl)benzoic acid | 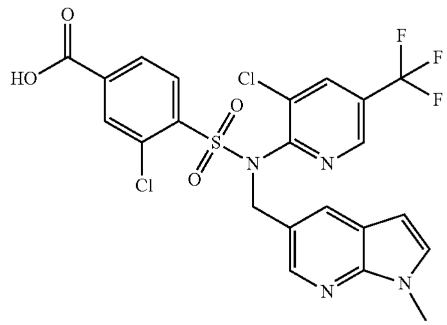 [SMILES: Cn1ccc2cc(CN(c3ncc(C(F)(F)F)cc3Cl)S(=O)(=O)c3ccc(C(=O)O)cc3Cl)cnc21] | 1.37 min | 557.3 |
| Example 36 | 3-Chloro-4-(N-(3,5-dichloropyridin-2-yl)-N-((1-methyl-1H-pyrrolo[2,3-b]pyridin-5-yl)methyl)sulfamoyl)benzoic acid | 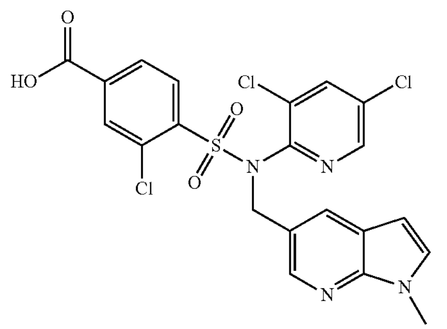 [SMILES: Cn1ccc2cc(CN(c3ncc(Cl)cc3Cl)S(=O)(=O)c3ccc(C(=O)O)cc3Cl)cnc21] | 1.32 min | 523.2 |
| Example 37 | 4-(N-(3-Chloro-5-(trifluoromethyl)pyridin-2-yl)-N-((1-methyl-1H-pyrrolo[2,3-b]pyridin-5-yl)methyl)sulfamoyl)benzoic acid | 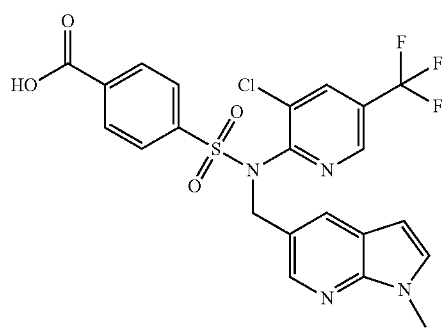 | 1.33 min | 523.3 |
| Example 38 | 4-(N-(3-Chloro-5-(trifluoromethyl)pyridin-2-yl)-N-(quinolin-3-ylmethyl)sulfamoyl)benzoic acid | 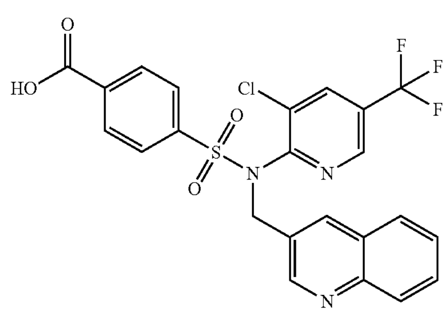 [SMILES: O=C(O)c1ccc(S(=O)(=O)N(Cc2cnc3ccccc3c2)c2ncc(C(F)(F)F)cc2Cl)cc1] | 1.35 min | 519.9 |

TABLE 1-continued

| Example | Name | Structure | HPLC Retention Time | MS (ESI): m/z (M − H)+ |
|---|---|---|---|---|
| Example 39 | 4-(N-(3-Chloro-5-(tri-fluoromethyl)pyridin-2-yl)-N-(quinolin-6-ylmethyl)sulfamoyl)benzoic acid | 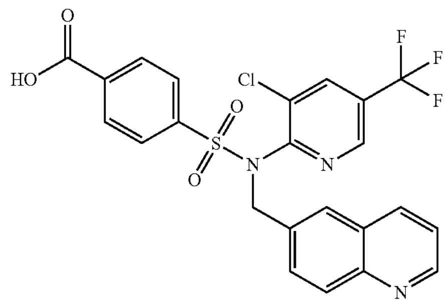 [SMILES: O=C(O)c1ccc(S(=O)(=O)N(Cc2ccc3ncccc3c2)c2ncc(C(F)(F)F)cc2Cl)cc1] | 1.31 min | 520.0 |

Intermediates in the Step A-b (N-arylation) described in the general synthesis for the preparation of Example compounds are shown in the Table 2.

TABLE 2

| Example | Intermediate |
|---|---|
| Example 1 Example 5 | 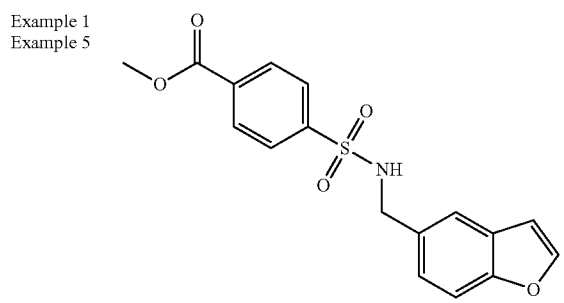 |
| Example 2 Example 10 | 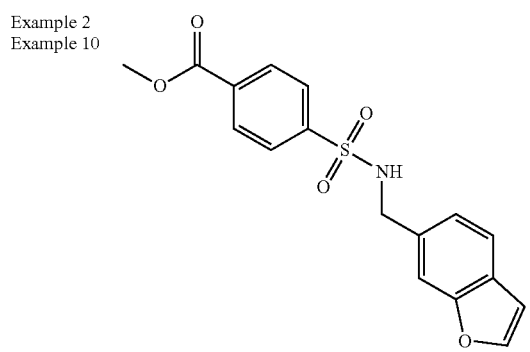 |
| Example 3 | 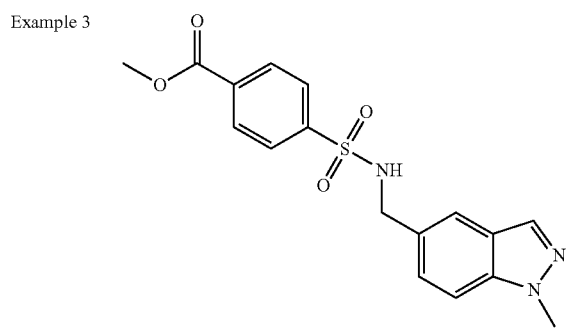 |

TABLE 2-continued

| Example | Intermediate |
|---|---|
| Example 4 Example 23 | 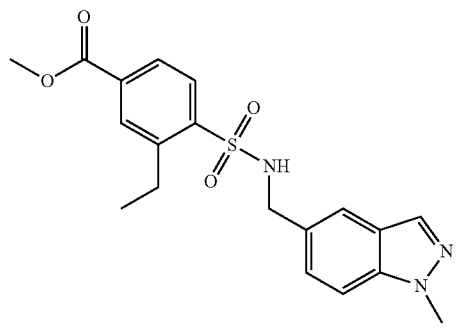 [SMILES: CCc1cc(C(=O)OC)ccc1S(=O)(=O)NCc1ccc2c(cnn2C)c1] |
| Example 6 Example 7 | 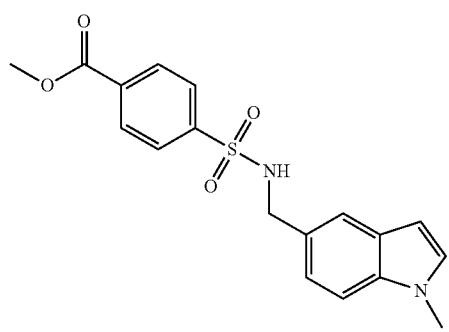 [SMILES: COC(=O)c1ccc(S(=O)(=O)NCc2ccc3c(ccn3C)c2)cc1] |
| Example 8 Example 9 | 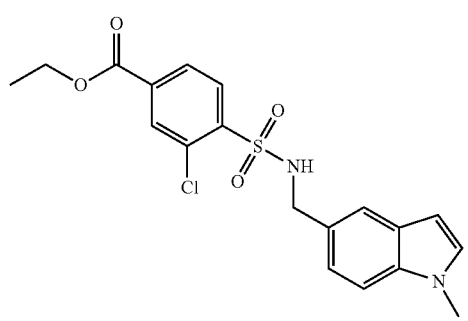 [SMILES: CCOC(=O)c1ccc(S(=O)(=O)NCc2ccc3c(ccn3C)c2)c(Cl)c1] |

TABLE 2-continued

| Example | Intermediate |
|---|---|
| Example 11 Example 12 | methyl 3-methyl-4-(N-((1-methyl-1H-indol-5-yl)methyl)sulfamoyl)benzoate |
| Example 13 | methyl 4-(N-((2-ethyl-2H-indazol-5-yl)methyl)sulfamoyl)benzoate |
| Example 14 | ethyl 3-chloro-4-(N-((1-ethyl-1H-indazol-5-yl)methyl)sulfamoyl)benzoate |
| Example 15 Example 19 | methyl 4-(N-((1-ethyl-1H-indazol-5-yl)methyl)sulfamoyl)benzoate |
| Example 16 | methyl 4-(N-((2-methyl-2H-indazol-5-yl)methyl)sulfamoyl)benzoate |
| Example 17 | methyl 4-(N-((1-methyl-1H-indazol-6-yl)methyl)sulfamoyl)benzoate |
| Example 18 | methyl 4-(N-((2-methyl-2H-indazol-6-yl)methyl)sulfamoyl)benzoate |
| Example 20 | methyl 4-(N-((1-(2-methoxyethyl)-1H-indazol-5-yl)methyl)sulfamoyl)benzoate |
| Example 21 | methyl 4-(N-((1-(tetrahydro-2H-pyran-4-yl)-1H-indazol-5-yl)methyl)sulfamoyl)benzoate |

TABLE 2-continued
| Example | Intermediate |
|---|---|
| Example 22 | 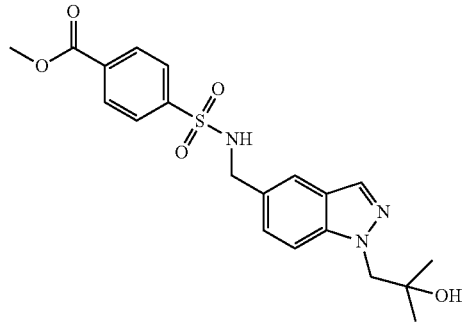 [SMILES: COC(=O)c1ccc(S(=O)(=O)NCc2ccc3c(cnn3CC(C)(C)O)c2)cc1] |
| Example 24
Example 25 | 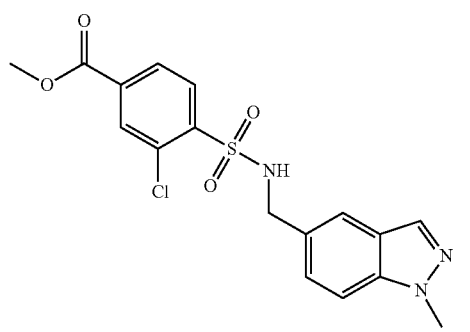 [SMILES: COC(=O)c1ccc(S(=O)(=O)NCc2ccc3c(cnn3C)c2)c(Cl)c1] |
| Example 26
Example 27 | 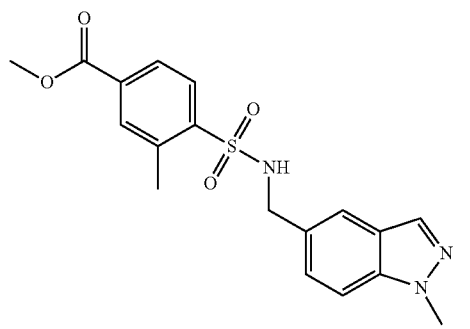 [SMILES: COC(=O)c1ccc(S(=O)(=O)NCc2ccc3c(cnn3C)c2)c(C)c1] |
| Example 28
Example 29 | 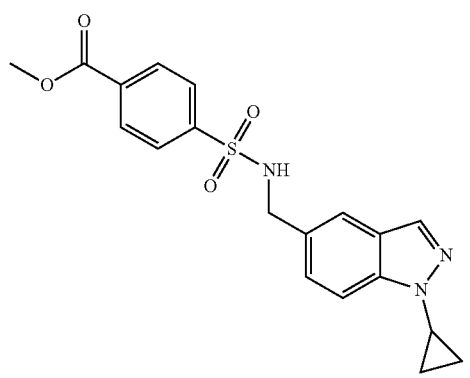 [SMILES: COC(=O)c1ccc(S(=O)(=O)NCc2ccc3c(cnn3C3CC3)c2)cc1] |
| Example 30 | 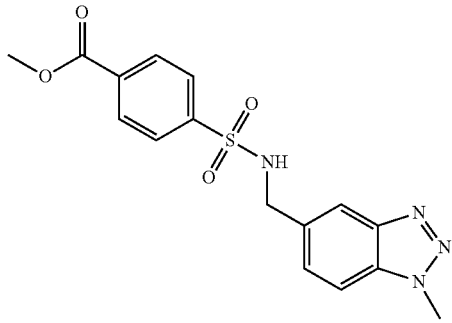 [SMILES: COC(=O)c1ccc(S(=O)(=O)NCc2ccc3c(c2)nnn3C)cc1] |
| Example 31
Example 32 | 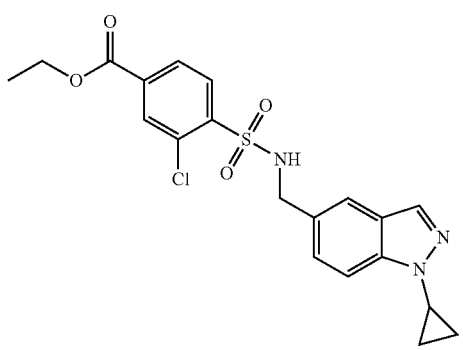 [SMILES: CCOC(=O)c1ccc(S(=O)(=O)NCc2ccc3c(cnn3C3CC3)c2)c(Cl)c1] |
| Example 33
Example 34 | 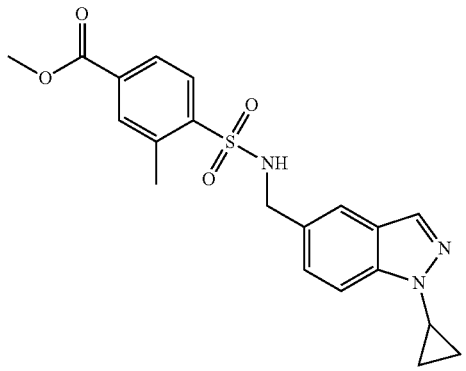 [SMILES: COC(=O)c1ccc(S(=O)(=O)NCc2ccc3c(cnn3C3CC3)c2)c(C)c1] |
| Example 35
Example 36 | 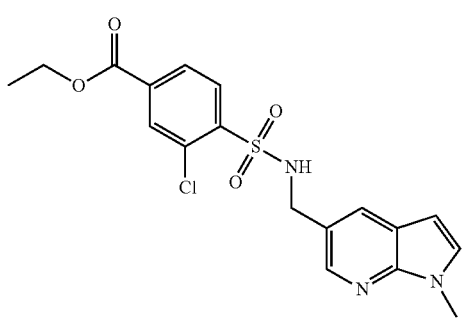 [SMILES: CCOC(=O)c1ccc(S(=O)(=O)NCc2cnc3c(ccn3C)c2)c(Cl)c1] |

TABLE 2-continued

| Example | Intermediate |
|---|---|
| Example 37 | (structure: methyl 4-[(1-methyl-1H-pyrrolo[2,3-b]pyridin-5-yl)methylsulfamoyl]benzoate) |
| Example 38 | (structure: methyl 4-[(quinolin-3-yl)methylsulfamoyl]benzoate) |
| Example 39 | (structure: methyl 4-[(quinolin-6-yl)methylsulfamoyl]benzoate) |

Measurement of the Menthol-Induced $Ca^{2+}$ Influx in HEK293 Cells Stably Expressing Human TRPM8

A cell-based $Ca^{2+}$ influx assay using HEK293 cells stably expressing human TRPM8 was used to identify the activity of compounds.

HEK293 cells stably expressing human TRPM8 were grown in T175 flasks at 37° C. in a 5% $CO_2$ humidified incubator to about 80% confluence. Media composition consisted of Dulbecco's Modified Eagle Medium (high glucose), 10% fetal calf serum (FCS), 100 units/ml Penicillin, 100 microg/ml Streptomycin and 600 microg/ml Geneticine. At 24 hours prior to assay, cells were seeded in poly-D-lysine coated 384-well plates (BD FALCON) at a density of 30,000 cells per well in culture medium and grown overnight in 5% $CO_2$ at 37° C. On the assay day, growth media was removed and cells were loaded with 0.5 microM Fluo4-AM (Molecular Probes) and 0.005% Pluronic F-127 dissolved in assay buffer (Hank's balanced salt solution (HBSS), 19.4 mM HEPES pH7.4, 2.5 mM Probenecid) for 1 hour at room temperature. After washing with assay buffer, the cells were preincubated with various concentrations of the compounds for 5 min. The changes in intracellular calcium concentration by addition of 30 microM menthol were monitored by the cell imaging technology by Hamamatsu Photonics's Functional Drug Screening System (FDSS).

The $IC_{50}$ values for compounds of the present invention were determined from 11-point dose-response studies. Curves were generated using the average of duplicate wells for each data point. Finally, the $IC_{50}$ values are calculated with the best-fit dose curve determined by XLfit (ID Business Solutions Ltd.). The resultant data are displayed in Table 3.

TABLE 3

Summary of the assay. $IC_{50}$: **; <1 microM, *; 1 to 10 microM

| Example | $IC_{50}$ | Example | $IC_{50}$ | Example | $IC_{50}$ |
|---|---|---|---|---|---|
| Example 1 | ** | Example 2 | ** | Example 3 | ** |
| Example 4 | ** | Example 5 | ** | Example 6 | ** |
| Example 7 | ** | Example 8 | ** | Example 9 | ** |
| Example 10 | ** | Example 11 | ** | Example 12 | ** |
| Example 13 | ** | Example 14 | ** | Example 15 | ** |
| Example 16 | * | Example 17 | ** | Example 18 | * |
| Example 19 | ** | Example 20 | ** | Example 21 | ** |
| Example 22 | * | Example 23 | ** | Example 24 | ** |
| Example 25 | ** | Example 26 | ** | Example 27 | ** |
| Example 28 | ** | Example 29 | ** | Example 30 | * |
| Example 31 | ** | Example 32 | ** | Example 33 | ** |
| Example 34 | ** | Example 35 | ** | Example 36 | * |
| Example 37 | ** | Example 38 | ** | Example 39 | ** |

Measurement of the Menthol-Induced $Ca^+$ Influx in a Human Malignant Melanoma Cell Lines Since TRPM8 is expressed in a human malignant melanoma cell lines, G-361 (Health Science Research Resources Bank, Osaka, Japan), the G-361 cells were used for in vitro functional assay.

G-361 cells were grown in T175 flasks at 37° C. in a 5% $CO_2$ humidified incubator to about 80% confluence. Media composition consisted of McCoy's 5A medium and 10% FCS. At 48 hours prior to assay, cells were seeded in poly-D-lysine coated 96-well plates (Corning) at a density of 12,000 cells per well in culture medium and grown in 5% $CO_2$ at 37° C. On the assay day, growth media was removed and cells were loaded with 5 microM Fluo4-AM (Molecular Probes) and 0.005% Pluronic F-127 dissolved in assay buffer (HBSS, 19.4 mM HEPES pH7.4, 2.5 mM Probenecid) for 1 hour at room temperature. After washing with assay buffer, the cells were preincubated with various concentrations of the compounds for 5 min. The changes in intracellular calcium concentration by addition of 300 microM menthol were monitored by FDSS.

The $IC_{50}$ values for compounds of the present invention were determined from dose-response studies. Curves were generated using the average of duplicate wells for each data point. Finally, the $IC_{50}$ values are calculated with the best-fit dose curve determined by XLfit (ID Business Solutions Ltd.).

Compounds of this invention showed good $IC_{50}$ values, which show the above-mentioned practical use.

Chronic Constriction Injury (CCI)-Induced Model of Neuropathic Pain: Cold Allodynia Male Sprague Dawley rats (7 weeks old at the start of experiment, n=7-10/treatment) purchased from Charles River Japan, Inc. were used. The CCI was made according to the method of Bennett G J and Xie Y K (Pain 1988, 33: 87-107). Rats were anesthetized with intraperitoneal injection of sodium pentobarbital. The left common sciatic nerve was exposed at the level of the middle of the thigh and four ligatures were loosely tided around it by using 4-0 silk thread (Ethicon Inc.) with about 1 mm space. Sham operation was performed in the same manner except of sciatic nerve ligation. One to two weeks following CCI surgery, cold allodynia was assessed using a cold plate (LHP-1700CP, TECA) with a temperature controller (Mode 13300-0, CAL Controls Inc.)

as described by Tanimoto-Mori S et al. (Behav Pharmacol. 2008, 19: 85-90). The animals were habituated to the apparatus which consists of a transparent acrylic box (10×12×12 cm) on a stainless-steel plate (15×33 cm). The surface of the cold plate held on 10° C. and the temperature of the plate was monitored continuously with a precision of 0.1° C. For testing, the rat was placed on the cold plate and the paw withdrawal latency (PWL) was measured before and after the compound administration, with a cut-off value of 120 seconds. The compounds of the invention or their vehicles were administered perorally, subcutaneously or intraperitoneally. The percentages of inhibition were calculated as follows;

$$\text{Inhibition (\%)} = \frac{PWL_{drug} - PWL_{vehicle}}{PWL_{sham} - PWL_{vehicle}} \times 100. \quad [\text{Math. 1}]$$

Compounds of this invention showed potent activities in this model, which show the above-mentioned practical use.

Chronic Constriction Injury (CCD-Induced Model of Neuropathic Pain: Static Allodynia Male Sprague Dawley rats (7 weeks old at the start of experiment, n=7-10/treatment) purchased from Charles River Japan, Inc. were used. The CCI was made according to the method of Bennett G J and Xie Y K (Pain 1988, 33: 87-107). Rats were anesthetized with intraperitoneal injection of sodium pentobarbital. The left common sciatic nerve was exposed at the level of the middle of the thigh and four ligatures were loosely tided around it by using 4-0 silk thread (Ethicon Inc.) with about 1 mm space. Sham operation was performed in the same manner except of sciatic nerve ligation. Static allodynia was assessed using von Frey hairs (VFHs) at two to three weeks following CCI surgery as described by Field M J et al. (Pain 1999, 83: 303-311). The animals were habituated to grid bottom cages prior to the start of experiment. VFHs in ascending order of force (0.16, 0.4, 0.6, 1, 1.4, 2, 4, 6, 8, 10, 15 and 26 gram) were applied to the plantar surface of the hind paw. Each VFH was applied to the ipsilateral paw for 6 seconds or until a withdrawal response was occurred. Once a withdrawal response was happened, the paw was re-tested, starting with the next descending VFH until no response was occurred. The lowest amount of force required to elicit a response was recorded as paw withdrawal threshold (PWT). Static allodynia was defined as present if animals responded to or below the innocuous 1.4 gram VFH. The compounds of the invention or their vehicles were administered perorally, subcutaneously or intraperitonealy. The percentages of inhibition were calculated as follows;

$$\text{Inhibition (\%)} = \frac{\log_{10}(PWT_{drug}) - \log_{10}(PWT_{vehicle})}{\log_{10}(PWT_{sham}) - \log_{10}(PWT_{vehicle})} \times 100. \quad [\text{Math. 2}]$$

Compounds of this invention showed potent activities in this model, which show the above-mentioned practical use.

Oxaliplatin-induced model of neuropathic pain: cold and static allodynia Male Sprague Dawley rats (7 weeks old at the start of experiment, n=7-10/treatment) purchased from Charles River Japan, Inc. were used. The study was conducted according to the method of Gauchan P et al. (NeuroSci Lett, 2009, 458, 93-95). Oxaliplatin (Yakult Co., Ltd.) was dissolved in 5% glucose. Oxaliplatin (4 mg/kg) was injected intraperitoneally twice a week for two-week. Cold allodynia was assessed using a cold plate (LHP-1700CP, TECA) with a temperature controller (Mode 13300-0, CAL Controls Inc.) as described by Tanimoto-Mori S et al. (Behav Pharmacol. 2008, 19: 85-90). The animals were habituated to the apparatus which consists of a transparent acrylic box (10×12×12 cm) on a stainless-steel plate (15×33 cm). The surface of the cold plate held on 10° C. and the temperature of the plate was monitored continuously with a precision of 0.1° C. For testing, the animal was placed on the cold plate and PWL was measured before and after the compound administration, with a cut-off value of 120 seconds. Static allodynia was assessed using VFHs. The animals were habituated to grid or mesh bottom cages prior to the start of experiment. VFHs in ascending order of force (0.16, 0.4, 0.6, 1, 1.4, 2, 4, 6, 8, 10, 15 and 26 gram) were applied to the plantar surface of the hind paw. Once a withdrawal response was happened, the paw was re-tested, starting with the next descending VFH until no response was occurred. The lowest amount of force required to elicit a response was recorded as paw withdrawal threshold (PWT). For testing, PWT was measured before and after the compound administration. The compounds of the invention or their vehicles were administered perorally, subcutaneously or intraperitonealy. Compounds of this invention showed potent activities in this model, which show the above-mentioned practical use.

Icilin-Induced Wet-Dog Shakes in Rats

Male Sprague Dawley rats (6-7 weeks old, Charles River Japan, Inc., n=5-8/treatment) were used to evaluate the ability of the compounds of the invention to block the spontaneous wet-dog shakes (WDS) behavior induced by icilin. Rats were acclimated in observation boxes (21.5×26.5×25.0 cm) for at least 20 minutes before icilin injection. Icilin (Sigma) dissolved in PEG400 was administered intraperitoneally at 0.5, 1.0 or 2.5 mg/kg and spontaneous WDS were counted over 30 min post-icilin. The compounds of the invention or their vehicles were administered perorally, subcutaneously or intraperitonealy before icilin injection. The percentages of inhibition were calculated as follows;

% inhibition=[1−(compound WDS count/vehicle WDS count)]×100.

Compounds of this invention showed potent activities in this model, which show the above-mentioned practical use.

Measurement of the Micturition Frequency in Guinea Pigs In vivo

Female Guinea Pigs (300-450 g) were anaesthetized with urethane. A midline abdominal incision was performed, both ureters were exposed and ligated, a catheter was implanted in the bladder pole and the abdomen was closed. For administration of the compounds the vena jugularis was exposed and canulated with a catheter. After this surgery the bladder catheter was connected via a t-shaped tube to an infusion pump and to a pressure transducer. Saline was infused and intrabladder pressure was registered. After 1 h of equilibration period and the establishment of constant voiding cycles, menthol (0.2-0.6 mM) was added to the infused saline. At this point also vehicle (control group) or TRPM8 antagonists were administered i.v. as bolus injection. The effect of treatment on the micturition interval (corresponding to bladder capacity) and micturition pressure was calculated and compared between vehicle-treated and compound-treated groups.

Compounds of this invention showed potent activities in this model, which show the above-mentioned practical use.

Measurement of Over Active Bladder in Anesthetized Cystitis Rats

Female Sprague-Dawley rats (7-8 weeks/Japan SLC) were used. Cyclophosphamide (Wako) dissolved in saline (Otsuka) was administered intraperitoneally at 200 mg/kg. On the next day, rats were anesthetized by administration of urethane at 0.9 mg/kg, s.c. The abdomen was opened through a midline incision, and a polyethylene catheter was implanted into the bladder through the dome. The bladder catheter was connected via T-tube to a pressure transducer and a microinjection pump. Saline was infused at room temperature into the bladder at a rate of 3 mL/hour. Intravesical pressure was recorded continuously on a chart pen recorder for about 1 hour before a test compound administration.

A testing compound dissolved in PBS containing Wellsolve (Celeste) was administered intravenously at 1 mg/kg, 3 mg/kg, 5 mg/kg or 10 mg/kg.

The micturition frequency calculated from micturition interval during 60 min after administration of testing compound was analyzed from the cystometry data. The testing compounds mediated inhibition of the frequency was evaluated using Dunnett' method vs vehicle. A probability levels less than 5% was accepted as significant difference. Data were analyzed as the mean±SEM from 8-12 rats.

All tested compounds showed significant effect on over active bladder in anesthetized cystitis rats.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A compound of the formula (I)

[Chem. 1]

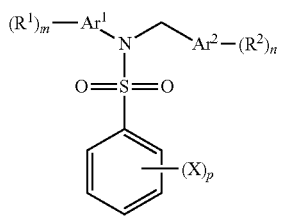

(I)

wherein $Ar^1$ is monocyclic heteroaryl;

$Ar^2$ is bicyclic heteroaryl;

$R^1$ is hydrogen, halogen, $C_1$-$C_4$ alkyl, $C_1$-$C_4$ haloalkyl, hydroxy, $C_1$-$C_4$ alkoxy, $C_1$-$C_4$ haloalkoxy, $C_1$-$C_4$ alkylthio, nitro, amino, $C_1$-$C_4$ alkylamino, di($C_1$-$C_4$ alkyl)amino, cyano, hydroxy $C_1$-$C_4$ alkyl, $C_1$-$C_4$ alkoxy $C_1$-$C_4$ alkyl, $C_1$-$C_4$ alkylsulfonyl, aminosulfonyl, $C_1$-$C_4$ alkyl C(=O)—, HO(O=)C—, $C_1$-$C_4$ alkyl-O(O=)C—, $R^3N(R^4)C(=O)$—, $C_1$-$C_4$ alkylsulfonylamino, $C_3$-$C_7$ cycloalkyl, or $R^3C(=O)N(R^4)$—;

$R^2$ is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, nitro, $C_1$-$C_4$ alkylsilyl, di($C_1$-$C_4$ alkyl)silyl, tri($C_1$-$C_4$ alkyl) silyl, amino, $C_1$-$C_4$ alkylamino, di($C_1$-$C_4$ alkyl)amino, cyano, hydroxy $C_1$-$C_4$ alkyl, $C_1$-$C_4$ alkoxy $C_1$-$C_4$ alkyl, $C_1$-$C_4$ alkylsulfonyl, aminosulfonyl, $C_1$-$C_4$ alkyl C(=O)—, HO(O=)C—, $C_1$-$C_4$ alkyl-O(O=)C—, $R^5N(R^6)C(=O)$—, $C_1$-$C_4$ alkylsulfonylamino, $C_3$-$C_7$ cycloalkyl, 3 to 7 membered heterocyclyl, or $R^5C(=O)N(R^6)$—;

said $C_3$-$C_7$ cycloalkyl and 3 to 7 membered heterocyclyl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl, cyano, amino, $C_1$-$C_4$ alkylamino, di($C_1$-$C_4$ alkyl)amino, $C_1$-$C_4$ alkylthio, $R^5N(R^6)C(=O)$—and nitro;

X is independently selected from HO(O=)C—$C_0$-$C_4$alkyl, hydrogen, hydroxy, halogen, $C_1$-$C_4$ alkyl, $C_1$-$C_4$ alkoxy, hydroxy $C_1$-$C_4$ alkyl, $C_1$-$C_4$ haloalkyl, $C_1$-$C_4$ haloalkoxy, $C_3$-$C_7$ cycloalkyl, cyano, alkylsulfonyl, $C_1$-$C_4$ alkyl C(=O)—, $C_1$-$C_4$ alkyl-O(O=)C—, and R7N(R8)C(=O)—;

said alkyl may have independently 1 to 4 substituents independently selected from $C_1$-$C_4$ alkyl and halogen;

m is 1, 2 or 3; when m is two or more than two, $R^1$ may be same or different;

n is 1, 2 or 3; when n is two or more than two, $R^2$ may be same or different;

p is 1, 2, 3, 4 or 5; when p is two or more than two, X may be same or different;

$R^3$, $R^4$, $R^5$, $R^6$, $R^7$ and $R^8$ are independently selected from hydrogen, $C_1$-$C_4$ alkyl, hydroxy $C_1$-$C_4$ alkyl, $C_1$-$C_4$ alkoxy $C_1$-$C_4$ alkyl, amino $C_1$-$C_4$ alkyl, $C_1$-$C_4$ alkylamino $C_1$-$C_4$ alkyl, di($C_1$-$C_4$ alkyl)amino $C_1$-$C_4$ alkyl, 5 to 10 membered aryl, 5 to 10 membered aryl $C_0$-$C_4$ alkyl;

said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_8$ cycloalkyl, amino, $C_1$-$C_4$ alkylamino, di($C_1$-$C_4$ alkyl)amino, $C_1$-$C_4$ alkylthio, and nitro;

$C_3$-$C_8$ cycloalkyl, and 3 to 8 membered heterocyclyl $C_1$-$C_4$ alkyl;

said heterocyclyl and alkyl may have independently 1 to 4 substituents independently selected from $C_1$-$C_4$ alkyl and halogen;

or alternatively $R^3$ and $R^4$, $R^5$ and $R^6$ or $R^7$ and $R^8$ together with nitrogen atom to which they are attached may independently form a 4 to 8 membered ring which may contain nitrogen, oxygen or sulfur, wherein the 4 to 8 membered ring is optionally substituted with 1 to 6 substituents independently selected from the group consisting of hydroxy, $C_1$-$C_4$ alkyl, $C_1$-$C_4$ alkoxy, $C_3$-$C_7$ cycloalkyl, amino, oxo, $C_1$-$C_4$ alkylamino, and di($C_1$-$C_4$ alkyl)amino;

or a pharmaceutically acceptable salt thereof or a prodrug thereof.

2. A compound of the formula (II)

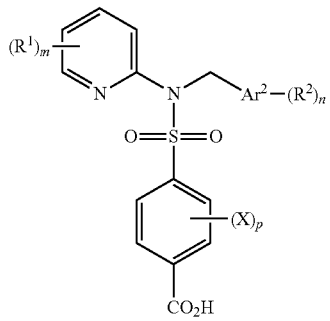

wherein
$R^1$, $R^2$, $Ar^e$, X, m and n are the same as in the definition described in claim 1;
p is 1, 2, 3 or 4; and when p is two or more than two, X may be same or different;
or a pharmaceutically acceptable salt thereof or a prodrug thereof.

3. A compound of the formula (III)

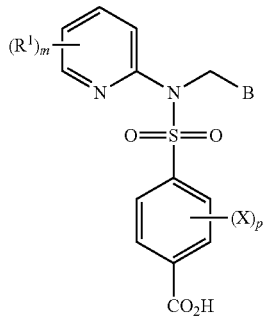

wherein

B is

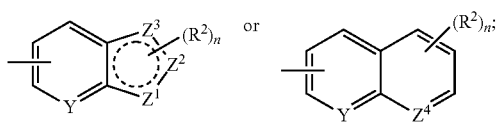

wherein
$R^1$, $R^2$, X, m and n are the same as in the definition described in claim 2;
p is 1 or 2; when p is two, X may be same or different;
Y is carbon or nitrogen;
$Z^1$, $Z^2$, $Z^3$, and $Z^4$ are independently selected from nitrogen, oxygen, and carbon;
m is 2; and
n is 0 or 1;
or a pharmaceutically acceptable salt thereof or a prodrug thereof.

4. The compound as claimed in claim 1 which is selected from:

4-(N-(Benzofuran-5-ylmethyl)-N-(3,5-dichloropyridin-2-yl)sulfamoyl)benzoic acid;
4-(N-(Benzofuran-6-ylmethyl)-N-(3,5-dichloropyridin-2-yl)sulfamoyl)benzoic acid;
4-(N-(3,5-Dichloropyridin-2-yl)-N-((1-methyl-1H-indol-5-yl)methyl)sulfamoyl)-3-methylbenzoic acid;
3-Chloro-4-(N-(3-chloro-5-(trifluoromethyl)pyridin-2-yl)-N-((1-ethyl-1H-indazol-5-yl)methyl)sulfamoyl)benzoic acid;
4-(N-(3-Chloro-5-(trifluoromethyl)pyridin-2-yl)-N-((1-ethyl-1H-indazol-5-yl)methyl)sulfamoyl)benzoic acid;
4-(N-(3,5-Dichloropyridin-2-yl)-N-((1-ethyl-1H-indazol-5-yl)methyl)sulfamoyl)benzoic acid;
4-(N-(Benzofuran-5-ylmethyl)-N-(3-chloro-5-(trifluoromethyl)pyridine -2-yl)sulfamoyl)benzoic acid;
4-(N-(Benzofuran-6-ylmethyl)-N-(3-chloro-5-(trifluoromethyl)pyridine -2-yl)sulfamoyl)benzoic acid;
4-(N-(3-Chloro-5-(trifluoromethyl)pyridin-2-yl)-N-((1-methyl - 1H-indazol-5-yl) methyl)sulfamoyl)-3-methylbenzoic acid;
4-(N-(3,5-Dichloropyridin-2-yl)-N-((1-methyl-1H-indazol-5-yl)methyl)sulfamoyl)-3-methylbenzoic acid;
4-(N-(3-Chloro-5-(trifluoromethyl)pyridin-2-yl)-N-((1-cyclopropyl-1H-indazol-5-yl)methyl)sulfamoyl)benzoic acid;
4-(N-((1-Cyclopropyl-1H-indazol-5-yl)methyl)-N-(3,5-dichloropyridin-2-yl)sulfamoyl)benzoic acid;
3-Chloro-4-(N-(3-chloro-5-(trifluoromethyl)pyridin-2-yl)-N-((1-cyclopropyl-1H-indazol-5-yl)methyl)sulfamoyl)benzoic acid;
3-Chloro-4-(N-((1-cyclopropyl-1H-indazol-5-yl)methyl)-N-(3,5-dichloropyridin-2-yl)sulfamoyl)benzoic acid;
4-(N-(3-Chloro-5-(trifluoromethyl)pyridin-2-yl)-N-((1-cyclopropyl-1H-indazol-5-yl)methyl)sulfamoyl)-3-methylbenzoic acid;
4-(N-((1-Cyclopropyl-1H-indazol-5-yl)methyl)-N-(3,5-dichloropyridin-2-yl)sulfamoyl)-3-methylbenzoic acid;
4-(N-(3-Chloro-5-(trifluoromethyl)pyridin-2-yl)-N-((methyl-1H -indol-5-yl)methyl)sulfamoyl)benzoic acid;
3-Chloro-4-(N-(3-chloro-5-(trifluoromethyl)pyridin-2-yl)-N -((1-methyl-1H-indol-5-yl)methyl)sulfamoyl)benzoic acid;
and 4-(N-(3-Chloro-5-(trifluoromethyl)pyridin-2-yl)-N-((1-methyl-1H-indol-5-yl)methyl)sulfamoyl)-3-methylbenzoic acid;
or a pharmaceutically acceptable salt thereof or a prodrug thereof.

5. A compound of the formula (IV),

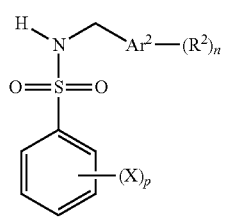

wherein
$Ar^2$ is bicyclic heteroaryl;
$R^2$ is hydrogen, halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, nitro, $C_1$-$C_4$ alkylsilyl, di($C_1$-$C_4$ alkyl)silyl, tri($C_1$-$C_4$ alkyl)

silyl, amino, $C_1$-$C_4$ alkylamino, di($C_1$-$C_4$ alkyl)amino, cyano, hydroxy $C_1$-$C_4$ alkyl, $C_1$-$C_4$ alkoxy $C_1$-$C_4$ alkyl, $C_1$-$C_4$ alkylsulfonyl, aminosulfonyl, $C_1$-$C_4$ alkyl C(=O)—, HO(O=)C—, $C_1$-$C_4$ alkyl-O(O=)C—, $R^5N(R^6)C(=O)$—, $C_1$-$C_4$ alkylsulfonylamino, $C_3$-$C_7$ cycloalkyl, 3 to 7 membered heterocyclyl, or $R^5C(=O)N(R^6)$- ;

said $C_3$-$C_7$ cycloalkyl and 3 to 7 membered heterocyclyl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_7$ cycloalkyl, cyano, amino, $C_1$-$C_4$ alkylamino, di($C_1$-$C_4$ alkyl)amino, $C_1$-$C_4$ alkylthio, $R^5N(R^6)C(=O)$— and nitro;

X is independently selected from HO(O=)C—$C_0$-$C_4$alkyl, hydrogen, hydroxy, halogen $C_1$-$C_4$alkoxy, hydroxy $C_1$-$C_4$ alkyl, $C_1$-$C_4$ haloalkyl, $C_1$-$C_4$ haloalkoxy, $C_3$-$C_7$ cycloalkyl, cyano, alkylsulfonyl, $C_1$-$C_4$ alkyl C(=O)—, $C_1$-$C_4$ alkyl-O(O=)C—, and $R^7N(R^8)C(=O)$—;

said alkyl may have independently 1 to 4 substituents independently selected from $C_1$-$C_4$ alkyl and halogen;

n is 1, 2 or 3; when n is two or more than two, $R^2$ may be same or different;

p is 1, 2, 3, 4 or 5; when p is two or more than two, X may be same or different;

$R^5$, $R^6$, $R^7$ and $R^8$ are independently selected from hydrogen, $C_1$-$C_4$ alkyl, hydroxy $C_1$-$C_4$ alkyl, $C_1$-$C_4$ alkoxy $C_1$-$C_4$ alkyl, amino $C_1$-$C_4$ alkyl, $C_1$-$C_4$ alkylamino $C_1$-$C_4$ alkyl, di($C_1$-$C_4$ alkyl)amino $C_1$-$C_4$ alkyl, 5 to 10 membered aryl, 5 to 10 membered aryl $C_0$-$C_4$ alkyl;

said aryl may be optionally substituted with 1 to 5 substituents independently selected from the group consisting of hydroxy, halogen, $C_1$-$C_4$ alkyl, $C_1$-$C_4$ alkoxy, hydroxy $C_1$-$C_4$ alkyl, amino $C_1$-$C_4$ alkyl, $C_1$-$C_4$ haloalkyl, $C_1$-$C_4$ haloalkoxy, $C_3$-$C_8$ cycloalkyl, amino, $C_1$-$C_4$ alkylamino, di($C_1$-$C_4$ alkyl)amino, $C_1$-$C_4$ alkylthio, and nitro;

$C_3$-$C_8$ cycloalkyl, and 3 to 8 membered heterocyclyl $C_1$-$C_4$ alkyl;

said heterocyclyl and alkyl may have independently 1 to 4 substituents independently selected from $C_1$-$C_4$ alkyl and halogen;

or alternatively $R^5$ and $R^6$ or $R^7$ and $R^8$ together with nitrogen atom to which they are attached may independently form a 4 to 8 membered ring which may contain nitrogen, oxygen or sulfur, wherein the 4 to 8 membered ring is optionally substituted with 1 to 6 substituents independently selected from the group consisting of hydroxy, $C_1$-$C_4$ alkyl, $C_1$-$C_4$ alkoxy, $C_3$-$C_7$ cycloalkyl, amino, oxo, $C_1$-$C_4$ alkylamino, and di($C_1$-$C_4$ alkyl) amino;

or a pharmaceutically acceptable salt thereof or a prodrug thereof.

6. A method for the treatment of a condition or disorder mediated by TRPM8 receptor antagonistic activity, in a mammalian subject, including a human, which comprises administering to a mammal in need of such treatment a therapeutically effective amount of a compound described in claim 1 or a pharmaceutically acceptable salt thereof or a prodrug thereof, wherein said condition or disorder is one or more of inflammatory, pain and urological diseases or disorders, including chronic pain, neuropathic pain including cold allodynia and diabetic neuropathy, postoperative pain, osteoarthritis, rheumatoid arthritic pain, cancer pain, neuralgia, neuropathies, algesia, nerve injury, migraine, cluster and tension headaches, ischaemia, irritable bowel syndrome, neurodegeneration, fibromyalgia, stroke, itch, psychiatric disorders including anxiety and depression and inflammatory disorders such as asthma and chronic obstructive pulmonary or airways, disease i.e., COPD, pulmonary hypertension, anxiety, including other stress-related disorders, urological diseases or disorders such as detrusor overactivity or overactive bladder, urinary incontinence, neurogenic detrusor overactivity or detrusor hyperflexia, idiopathic detrusor overactivity or detrusor instability, benign prostatic hyperplasia, and lower urinary tract symptoms, and combinations thereof.

7. A pharmaceutical composition comprising a compound or a pharmaceutically acceptable salt thereof or a prodrug thereof, as claimed in claim 1, and a pharmaceutically acceptable carrier.

8. A pharmaceutical composition as claimed in claim 7, further comprising another pharmacologically active agent.

9. A process for preparing a pharmaceutical composition comprising mixing the compound according to claim 1 or a pharmaceutically acceptable salt thereof or a prodrug thereof with a pharmaceutically acceptable carrier or excipient.

* * * * *